United States Patent
Long et al.

(10) Patent No.: US 11,694,418 B2
(45) Date of Patent: **\*Jul. 4, 2023**

(54) SYSTEMS AND METHODS FOR CONSTRUCTING A THREE-DIMENSIONAL MODEL FROM TWO-DIMENSIONAL IMAGES

(71) Applicant: SDC U.S. SmilePay SPV, Nashville, TN (US)

(72) Inventors: Josh Long, Nashville, TN (US); Jordan Katzman, Nashville, TN (US); Tim Wucher, Windhoek (NA); John Dargis, Nashville, TN (US); Christopher Yancey, Nashville, TN (US); Andrew Wright, Nashville, TN (US)

(73) Assignee: SDC U.S. SmilePay SPV, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/687,859

(22) Filed: Mar. 7, 2022

(65) Prior Publication Data

US 2022/0189130 A1 Jun. 16, 2022

Related U.S. Application Data

(60) Division of application No. 17/247,310, filed on Dec. 7, 2020, now Pat. No. 11,270,523, which is a
(Continued)

(51) Int. Cl.
*G06T 19/20* (2011.01)

(52) U.S. Cl.
CPC .......... *G06T 19/20* (2013.01); *G06T 2210/41* (2013.01); *G06T 2219/2004* (2013.01)

(58) Field of Classification Search
CPC .................. G06T 19/20; G06T 2210/41; G06T 2219/2004; A61C 9/0006; A61C 9/0053;
(Continued)

(56) References Cited

U.S. PATENT DOCUMENTS

| 5,886,702 A | 3/1999 | Migdal et al. |
| 5,945,996 A | 8/1999 | Migdal et al. |

(Continued)

FOREIGN PATENT DOCUMENTS

| CN | 106504331 | 3/2017 |
| CN | 107862738 | 10/2019 |

(Continued)

OTHER PUBLICATIONS

Georgia Gkioxari et al., Mesh R-CNN, Facebook AI Research (FAIR), Jun. 6, 2019, 15 Pages.

(Continued)

*Primary Examiner* — Abderrahim Merouan
(74) *Attorney, Agent, or Firm* — Foley & Lardner LLP

(57) ABSTRACT

Systems and methods for generating a three-dimensional (3D) model of a user's dental arch based on two-dimensional (2D) images of dental impressions include a model training system that provides a machine learning model using training image(s) of a dental impression of a respective dental arch and a 3D training model of the respective dental arch. A model generation system receives first image(s) of a first dental impression of a user's dental arch and second image(s), which may be of the first dental impression or a second dental impression of the dental arch. The model generation system generates a first and second 3D model of the dental arch by applying the first image(s) and second image(s) to the machine learning model.

20 Claims, 31 Drawing Sheets

Related U.S. Application Data continuation-in-part of application No. 17/247,055, filed on Nov. 25, 2020, now Pat. No. 11,403,813, which is a continuation-in-part of application No. 16/696,468, filed on Nov. 26, 2019, now Pat. No. 10,916,053, said application No. 17/247,310 is a continuation-in-part of application No. 16/548,712, filed on Aug. 22, 2019, now Pat. No. 10,861,250, which is a continuation-in-part of application No. 16/257,692, filed on Jan. 25, 2019, now Pat. No. 10,410,435, which is a continuation-in-part of application No. 16/165,439, filed on Oct. 19, 2018, now Pat. No. 10,964,121, which is a continuation of application No. 15/825,760, filed on Nov. 29, 2017, now Pat. No. 10,109,114.

(58) Field of Classification Search
CPC ....... A61C 7/002; A61C 9/0046; A61C 9/002; A61C 7/08; A61C 11/00; A61B 5/4547
See application file for complete search history.

(56) References Cited

U.S. PATENT DOCUMENTS

| | | |
|---|---|---|
| 6,208,347 B1 | 3/2001 | Migdal et al. |
| 6,971,873 B2 | 12/2005 | Sachdeva et al. |
| 7,077,647 B2 | 7/2006 | Choi et al. |
| 7,084,868 B2 | 8/2006 | Farag et al. |
| 7,698,014 B2 | 4/2010 | Dunne et al. |
| 7,702,492 B2 | 4/2010 | Marshall |
| 7,831,322 B2 | 11/2010 | Liu et al. |
| 8,113,829 B2 | 2/2012 | Sachdeva et al. |
| 8,152,523 B2 | 4/2012 | Sporbert et al. |
| 8,234,000 B2 | 7/2012 | Andersson et al. |
| 8,417,366 B2 | 4/2013 | Getto et al. |
| 8,478,698 B1 | 7/2013 | Mah |
| 8,896,592 B2 | 11/2014 | Boltunov et al. |
| 8,995,732 B2 | 3/2015 | Kaza et al. |
| 9,299,192 B2 | 3/2016 | Kopelman |
| 9,301,814 B2 | 4/2016 | Kaza et al. |
| 9,566,132 B2 | 2/2017 | Stone-Collonge et al. |
| 9,626,462 B2 | 4/2017 | Somasundaram et al. |
| 9,684,952 B2 | 6/2017 | Carlson et al. |
| 9,770,217 B2 | 9/2017 | Sandholm et al. |
| 9,829,710 B1 | 11/2017 | Newell et al. |
| 9,838,670 B2 | 12/2017 | Glinec et al. |
| 9,839,494 B2 | 12/2017 | Kaza et al. |
| 10,074,178 B2 | 9/2018 | Cocco et al. |
| 10,109,114 B1 | 10/2018 | Yancey et al. |
| 10,143,537 B2 | 12/2018 | Kaza et al. |
| 10,162,908 B1 | 12/2018 | Bhaskara et al. |
| 10,248,883 B2 | 4/2019 | Borovinskih et al. |
| 10,335,252 B2 | 7/2019 | Kaza et al. |
| 10,398,539 B2 | 9/2019 | Nilsson |
| 10,405,947 B1 | 9/2019 | Kaza et al. |
| 10,441,395 B2 | 10/2019 | Mah |
| 10,485,638 B2 | 11/2019 | Salah et al. |
| 10,485,639 B2 | 11/2019 | Levin |
| 10,517,696 B2 | 12/2019 | Kitching et al. |
| 10,624,716 B2 | 4/2020 | Kitching et al. |
| 10,977,818 B2* | 4/2021 | Clark .................. G06T 7/77 |
| 11,043,026 B1 | 6/2021 | Fathi et al. |
| 2002/0028418 A1 | 3/2002 | Farag et al. |
| 2006/0040236 A1 | 2/2006 | Schmitt |
| 2006/0127855 A1* | 6/2006 | Wen .................... A61C 7/04 |
| | | 433/213 |
| 2006/0204078 A1 | 9/2006 | Orth et al. |
| 2006/0263738 A1 | 11/2006 | Kuo |
| 2006/0275736 A1 | 12/2006 | Wen et al. |
| 2007/0207437 A1 | 9/2007 | Sachdeva et al. |
| 2008/0206705 A1 | 8/2008 | Kaza et al. |
| 2009/0148816 A1 | 6/2009 | Marshall et al. |
| 2009/0160855 A1 | 6/2009 | Wu |
| 2009/0220134 A1 | 9/2009 | Cahill et al. |
| 2009/0316966 A1 | 12/2009 | Marshall et al. |
| 2010/0324875 A1 | 12/2010 | Kalili |
| 2011/0196653 A1 | 8/2011 | Lajoie et al. |
| 2011/0200248 A1 | 8/2011 | Matabosch I Gerones et al. |
| 2012/0015316 A1 | 1/2012 | Sachdeva et al. |
| 2012/0191421 A1 | 7/2012 | Greenberg |
| 2012/0330447 A1 | 12/2012 | Gerlach et al. |
| 2013/0051516 A1* | 2/2013 | Yang .................. G06T 11/005 |
| | | 378/4 |
| 2013/0218530 A1 | 8/2013 | Deichmann et al. |
| 2014/0026419 A1 | 1/2014 | Haber |
| 2014/0037194 A1 | 2/2014 | Kitamura et al. |
| 2014/0051037 A1 | 2/2014 | Fisker |
| 2014/0203463 A1 | 7/2014 | Haber |
| 2014/0254919 A1 | 9/2014 | Sun et al. |
| 2015/0182316 A1 | 7/2015 | Morales et al. |
| 2015/0199839 A1 | 7/2015 | Chon |
| 2015/0264299 A1 | 9/2015 | Leech et al. |
| 2015/0348320 A1 | 12/2015 | Pesach et al. |
| 2016/0125651 A1 | 5/2016 | Lior et al. |
| 2016/0148375 A1 | 5/2016 | Oh et al. |
| 2016/0175068 A1* | 6/2016 | Cai .................... A61C 7/002 |
| | | 700/98 |
| 2016/0210602 A1 | 7/2016 | Siddique et al. |
| 2016/0220173 A1* | 8/2016 | Ribnick ............. A61B 5/7278 |
| 2016/0220200 A1 | 8/2016 | Sandholm et al. |
| 2016/0228212 A1 | 8/2016 | Salah et al. |
| 2016/0324597 A1 | 11/2016 | Colby |
| 2017/0061588 A1 | 3/2017 | Lee et al. |
| 2017/0085863 A1* | 3/2017 | Lopez .................. H04N 13/261 |
| 2017/0161640 A1* | 6/2017 | Shamir ................. G06N 20/00 |
| 2017/0304950 A1 | 10/2017 | Moore |
| 2017/0312060 A1 | 11/2017 | Morales et al. |
| 2017/0340390 A1 | 11/2017 | Harbison et al. |
| 2017/0345147 A1 | 11/2017 | Ohtake et al. |
| 2018/0025496 A1 | 1/2018 | Lindner et al. |
| 2018/0028294 A1* | 2/2018 | Azernikov .......... G06K 9/6274 |
| 2018/0085201 A1 | 3/2018 | Wu et al. |
| 2018/0091169 A1 | 3/2018 | Colby |
| 2018/0168780 A1 | 6/2018 | Kopelman et al. |
| 2018/0168781 A1* | 6/2018 | Kopelman .......... G09B 23/283 |
| 2018/0206940 A1* | 7/2018 | Kopelman ............ G06T 7/0012 |
| 2018/0263731 A1 | 9/2018 | Pokotilov et al. |
| 2018/0263732 A1 | 9/2018 | Pokotilov et al. |
| 2018/0303581 A1 | 10/2018 | Martz et al. |
| 2018/0344430 A1 | 12/2018 | Salah et al. |
| 2018/0350134 A1 | 12/2018 | Lodato et al. |
| 2018/0352150 A1 | 12/2018 | Purwar et al. |
| 2018/0368943 A1 | 12/2018 | Katzman et al. |
| 2019/0026598 A1 | 1/2019 | Salah et al. |
| 2019/0026599 A1 | 1/2019 | Salah et al. |
| 2019/0026942 A1 | 1/2019 | Zhang |
| 2019/0090982 A1 | 3/2019 | Kuo |
| 2019/0090984 A1* | 3/2019 | Martz .................. B29C 64/124 |
| 2019/0125493 A1 | 5/2019 | Salah et al. |
| 2019/0139300 A1 | 5/2019 | Kirchberg et al. |
| 2019/0148005 A1 | 5/2019 | Domracheva et al. |
| 2019/0164353 A1 | 5/2019 | Yancey et al. |
| 2019/0175303 A1* | 6/2019 | Akopov ............. A61C 9/0053 |
| 2019/0246000 A1 | 8/2019 | Cheng et al. |
| 2019/0269483 A1* | 9/2019 | Kaza ................. A61C 9/0053 |
| 2019/0282344 A1 | 9/2019 | Azernikov et al. |
| 2019/0295223 A1* | 9/2019 | Shen .................... G06T 7/0002 |
| 2019/0313963 A1* | 10/2019 | Hillen ................. A61B 5/7475 |
| 2019/0332875 A1 | 10/2019 | Vallespi-Gonzalez et al. |
| 2019/0333622 A1* | 10/2019 | Levin .................. A61C 7/10 |
| 2019/0388188 A1 | 12/2019 | Kaza et al. |
| 2020/0000552 A1 | 1/2020 | Mednikov et al. |
| 2020/0031934 A1 | 1/2020 | Gu et al. |
| 2020/0100871 A1* | 4/2020 | Wang .................. G06F 17/18 |
| 2020/0404243 A1 | 12/2020 | Saphier et al. |
| 2020/0405464 A1* | 12/2020 | Nikolskiy .............. G06T 7/11 |
| 2021/0153986 A1* | 5/2021 | Wirjadi ................ G06T 17/10 |
| 2021/0174604 A1 | 6/2021 | Long et al. |

(56) References Cited

U.S. PATENT DOCUMENTS

2021/0186659 A1   6/2021  Li et al.
2022/0110723 A1\*  4/2022  Raby ........................ G06T 19/20

FOREIGN PATENT DOCUMENTS

| EP | 3 462 373 | 4/2019 |
| EP | 3 620 130 | 3/2020 |
| WO | WO-2019/002631 | 1/2019 |

OTHER PUBLICATIONS

International Search Report and Written Opinion regarding Appl. No. PCT PCT/US2021/061997, dated Mar. 8, 2022, 15 pp.
U.S. Appl. No. 15/825,760, filed Nov. 29, 2017.
U.S. Appl. No. 16/165,439, filed Oct. 19, 2018.
U.S. Appl. No. 16/257,692, filed Jan. 25, 2019.
U.S. Appl. No. 16/548,712, filed Aug. 22, 2019.
U.S. Appl. No. 16/696,468, filed Nov. 26, 2019.
U.S. Appl. No. 17/247,055, filed Nov. 25, 2020.
U.S. Appl. No. 17/247,310, filed Dec. 7, 2020.
Charrier et al., "Comparison of No-Reference Image Quality Assessment Machine Learning-based Algorithms on Compressed Images", Feb. 2015, San Francisco, California, 10 pages.
Chen et al., "Learning to Predict 3D Objects with an Interpolation-based Differentiable Renderer", https://arxiv.org/pdf/1908.01210.pdf, Nov. 21, 2019, 11 Pages.
Fan et al., "A Point Set Generation Network for 3D Object Reconstruction From a Single Image", Stanford University, Dec. 7, 2016, 12 pages.
Gregor et al., "DRAW: A Recurrent Neural Network For Image Generation", Google DeepMind, May 20, 2015, 10 pages.
Hochreiter et al., "Long Short-Term Memory", Neural Computation: 9(8), Dec. 1997, 33 pages.
Howard et al., "MobileNets: Efficient Convolutional Neural Networks for Mobile Vision Applications", Apr. 17, 2017, 9 pages.
International Search Report and Written Opinion for International Application No. PCT/US2018/062824, dated Jan. 2, 2019, 8 pages.
International Search Report and Written Opinion for International Application No. PCT/US2020/014989, dated May 13, 2020, 12 pages.
International Search Report and Written Opinion on International Application No. PCT/US2020/070820, dated Mar. 12, 2021, 12 pages.
Kurenkov et al., "DeformNet: Free-Form Deformation Network for 3D Shape Reconstruction from a Single Image", Stanford Vision and Learning Lab, Aug. 11, 2017, 12 pages.
Li et al., "Point Cloud GAN", Carnegie Mellon University, Oct. 13, 2018, 19 pages.
Murtagh, Fionn, "Multilayer perceptrons for classification and regression", Jul. 1991, pp. 183-197.
Qi et al., "PointNet: Deep Hierarchical Feature Learning on Point Sets in a Metric Space", Stanford University, Jun. 7, 2017, 14 pages.
Rankred, "15 Tools To Instantly Convert 2d Images to 3d Ones", Jan. 1, 2020, http://www.rankred.com/convert-2d-images-to-3d, 23 pages.
Russakovsky et al., "ImageNet Large Scale Visual Recognition Challenge" Jan. 30, 2015, 43 pages.
Tatarchenko et al., "Octree Generating Networks: Efficient Convolutional Architectures for High-resolution 3D Outputs", University of Freiburg, Intel Labs, Aug. 7, 2017, 15 pages.
Wang et al., "MVPNet: Multi-View Point Regression Networks for 3D Object Reconstruction from A Single Image", Nov. 23, 2018, 8 pages.

\* cited by examiner

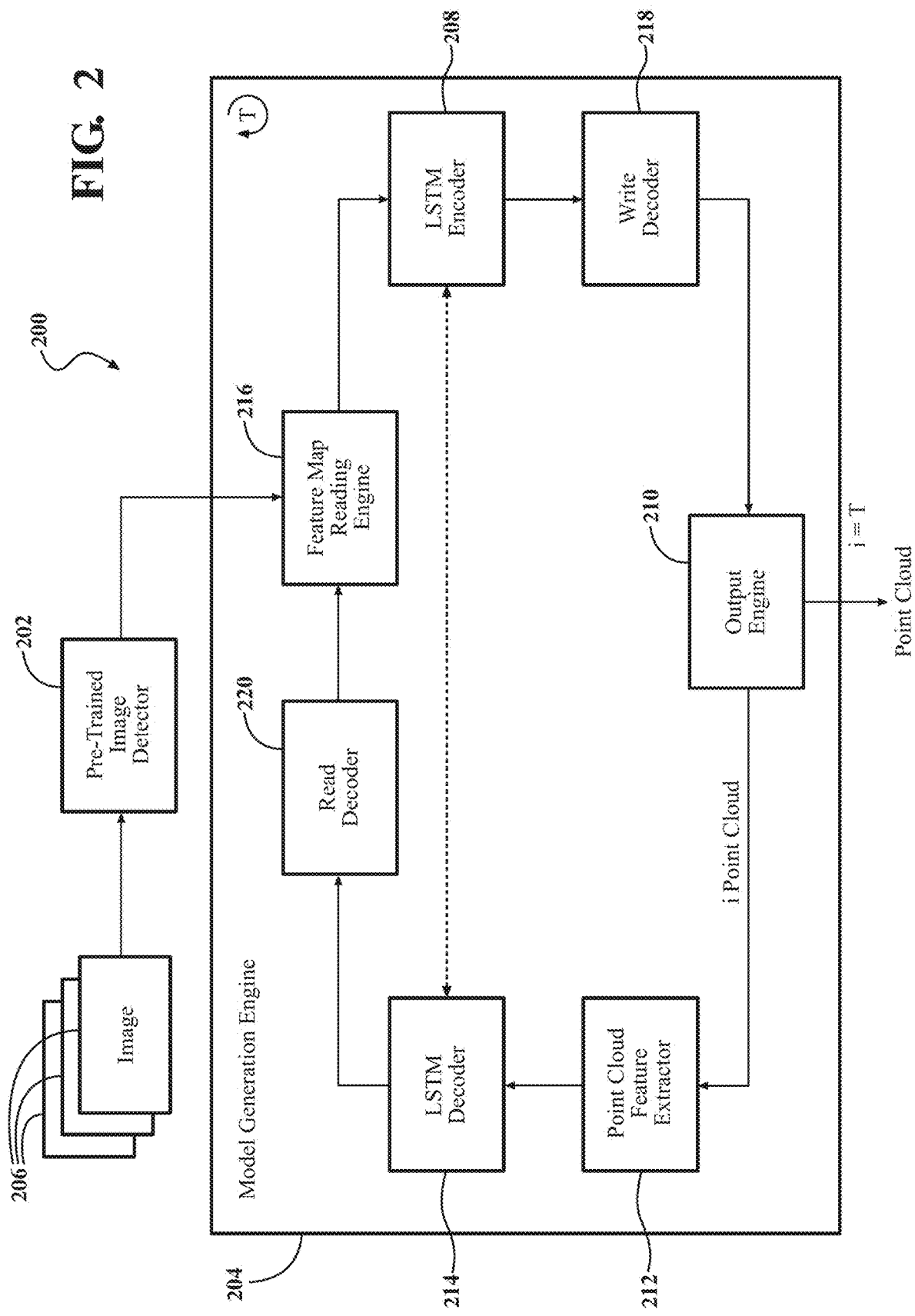

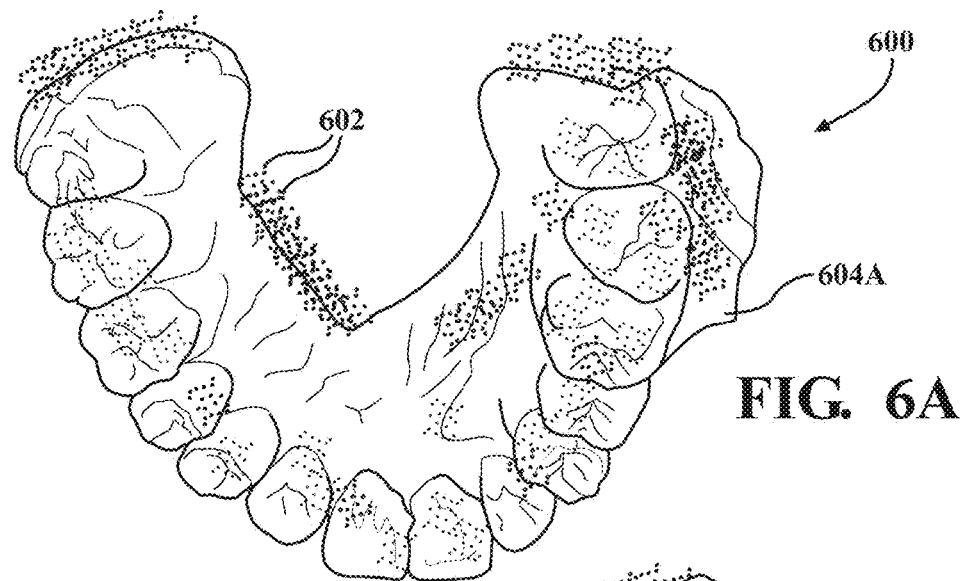
FIG. 6A
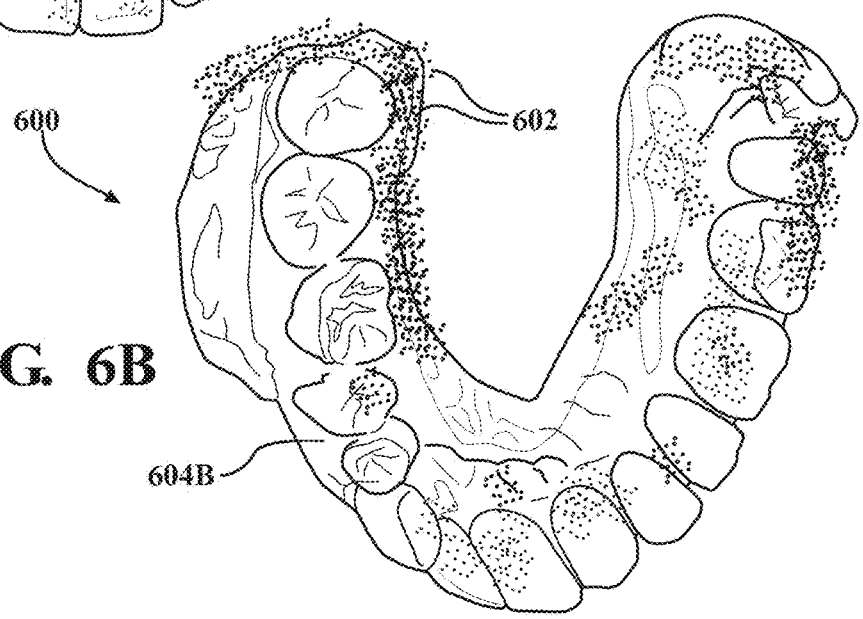
FIG. 6B
FIG. 6C
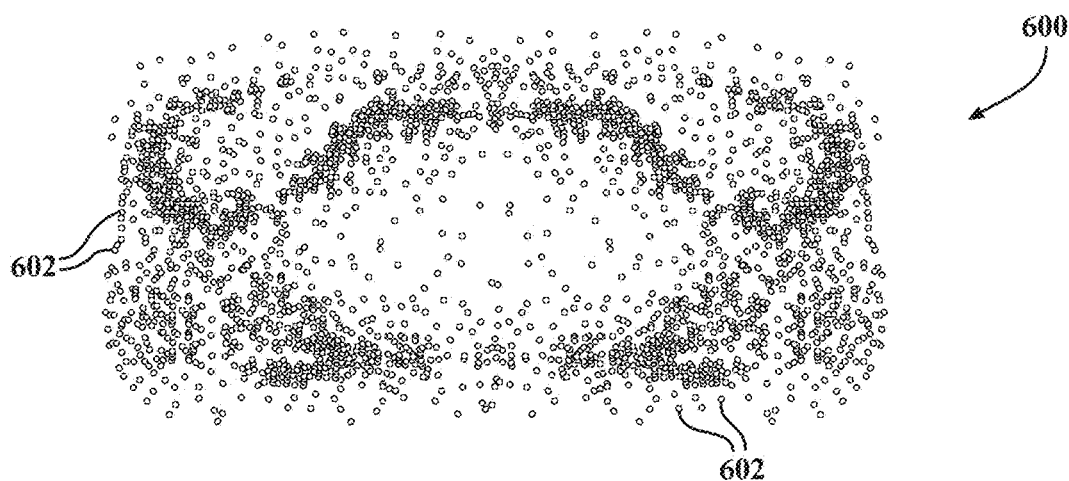

SYSTEMS AND METHODS FOR CONSTRUCTING A THREE-DIMENSIONAL MODEL FROM TWO-DIMENSIONAL IMAGES

CROSS-REFERENCE TO RELATED APPLICATIONS

This application is a divisional of U.S. patent application Ser. No. 17/247,310, filed Dec. 7, 2020, which is continuation-in-part of U.S. patent application Ser. No. 17/247,055, filed Nov. 25, 2020, which is a continuation-in-part of U.S. patent application Ser. No. 16/696,468, filed Nov. 26, 2019, now U.S. Pat. No. 10,916,053. U.S. patent application Ser. No. 17/247,310 is also a continuation-in-part of U.S. patent application Ser. No. 16/548,712, filed Aug. 22, 2019, now U.S. Pat. No. 10,861,250, which is a is a continuation-in-part of U.S. patent application Ser. No. 16/257,692, filed Jan. 25, 2019, now U.S. Pat. No. 10,410,435, which is a continuation-in-part of U.S. patent application Ser. No. 16/165,439, filed Oct. 19, 2018, now U.S. Pat. No. 10,964,121, which is a continuation of U.S. patent application Ser. No. 15/825,760, filed Nov. 29, 2017, now U.S. Pat. No. 10,109,114. The contents of each of which are hereby incorporated by reference in their entirety and for all purposes.

BACKGROUND

The present disclosure relates generally to constructing three-dimensional models for use in dental treatment. More specifically, the present disclosure relates to constructing three-dimensional models of a user's dental arch from two-dimensional images of dental impressions of the user's dental arch.

SUMMARY

An embodiment relates to a system. The system includes a model training system and a model generation system. The model training system is configured to receive a plurality of data packets of a training set. Each data packet of the plurality of data packets includes data corresponding to one or more training images of a dental impression of a respective dental arch and a three-dimensional (3D) training model of the respective dental arch. The model training system is configured to identify, for each data packet of the plurality of data packets of the training set, a plurality of correlation points between the one or more training images and the 3D training model of the respective dental arch. The model training system is configured to generate a machine learning model using the one or more training images, the 3D training model, and the plurality of correlation points between the one or more training images and the 3D training model of each data packet of the plurality of data packets of the training set. The model generation system is configured to receive one or more images of a dental impression of a dental arch of a user. The model generation system is configured to generate a 3D model of the dental arch of the user by applying the one or more images of the dental impression to the machine learning model.

Another embodiment relates to a system. The system includes a model generation system and a model merging system. The model generation system is configured to receive one or more first images of a first dental impression of a dental arch of a user. The model generation system is configured to generate a first three-dimensional (3D) model of the dental arch of the user by applying the one or more first images to a machine learning model trained to generate 3D models of dental arches from two-dimensional (2D) images of dental impressions of the dental arches. The model generation system is configured to receive one or more second images. The one or more second images are of one of the first dental impression of the dental arch or a second dental impression of the dental arch. The model generation system is configured to generate a second 3D model of the dental arch of the user by applying the one or more second images to the machine learning model. The model merging system is configured to merge the first 3D model and the second 3D model to generate a merged model.

Another embodiment relates to a method. The method includes providing, by a model training system, a machine learning model using one or more training images of a dental impression of a respective dental arch and a three-dimensional (3D) training model of the respective dental arch. The method includes receiving, by a model generation system, one or more first images of a first dental impression of a dental arch of a user. The method includes generating, by the model generation system, a first 3D model of the dental arch of the user by applying the one or more first images to the machine learning model. The method includes receiving, by the model generation system, one or more second images. The one or more second images are of one of the first dental impression of the dental arch or a second dental impression of the dental arch. The method includes generating, by the model generation system, a second 3D model of the dental arch of the user by applying the one or more second images to the machine learning model. The method includes merging, by a model merging system, the first 3D model and the second 3D model to generate a merged model of the dental arch of the user.

Another embodiment relates to a system. The system includes a model training system and a model generation system. The model training system is configured to receive a plurality of data packets of a training set. Each data packet of the plurality of data packets includes data corresponding to one or more training images of a dental impression of a respective dental arch and a three-dimensional (3D) training model of the respective dental arch. The model training system is configured to identify, for each data packet of the plurality of data packets of the training set, a plurality of correlation points between the one or more training images and the 3D training model of the respective dental arch. The model training system is configured to generate a machine learning model using the one or more training images, the 3D training model, and the plurality of correlation points between the one or more training images and the 3D training model of each data packet of the plurality of data packets of the training set. The model generation system is configured to receive one or more images of a dental impression of a dental arch of a user. The model generation system is configured to generate a 3D model of the dental impression of the dental arch by applying the one or more images of the dental impression to the machine learning model.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE DRAWINGS

FIG. 2 is a block diagram of a system for generating a 3D model from one or more two-dimensional (2D) images, according to an illustrative embodiment.

FIG. 6A is an illustration of an example point cloud overlaid on a digital model of upper dental arch, according to an illustrative embodiment.

FIG. 6B is an illustration of an example point cloud overlaid on a digital model of a lower dental arch, according to an illustrative embodiment.

FIG. 6C is an illustration of a point cloud including the point clouds shown in FIG. 6A and FIG. 6B, according to an illustrative embodiment.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, described herein are systems and methods for generating a three-dimensional (3D) model of a user's dental arch from two-dimensional (2D) images of a dental impression of the user's dental arch. A model generation system receives images of a dental impression of the user's dental arch, and generates a 3D model of the user's dental arch from the images. The systems and methods described herein have many advantages over other implementations. For instance, the systems and methods described herein expedite the manufacturing and delivery of dental aligners to a user by more efficiently generating 3D models of the user's dentition without requiring the user to conduct a scan of their dentition, or attend an appointment with a dentist or orthodontist. By not requiring an appointment with a dentist or orthodontist, such systems and methods may make users more comfortable and confident with receiving orthodontic treatment, and avoid delays in receiving orthodontic treatment due to schedule an appointment with a dentist or orthodontist to scan of the user's teeth.

Figure 1:
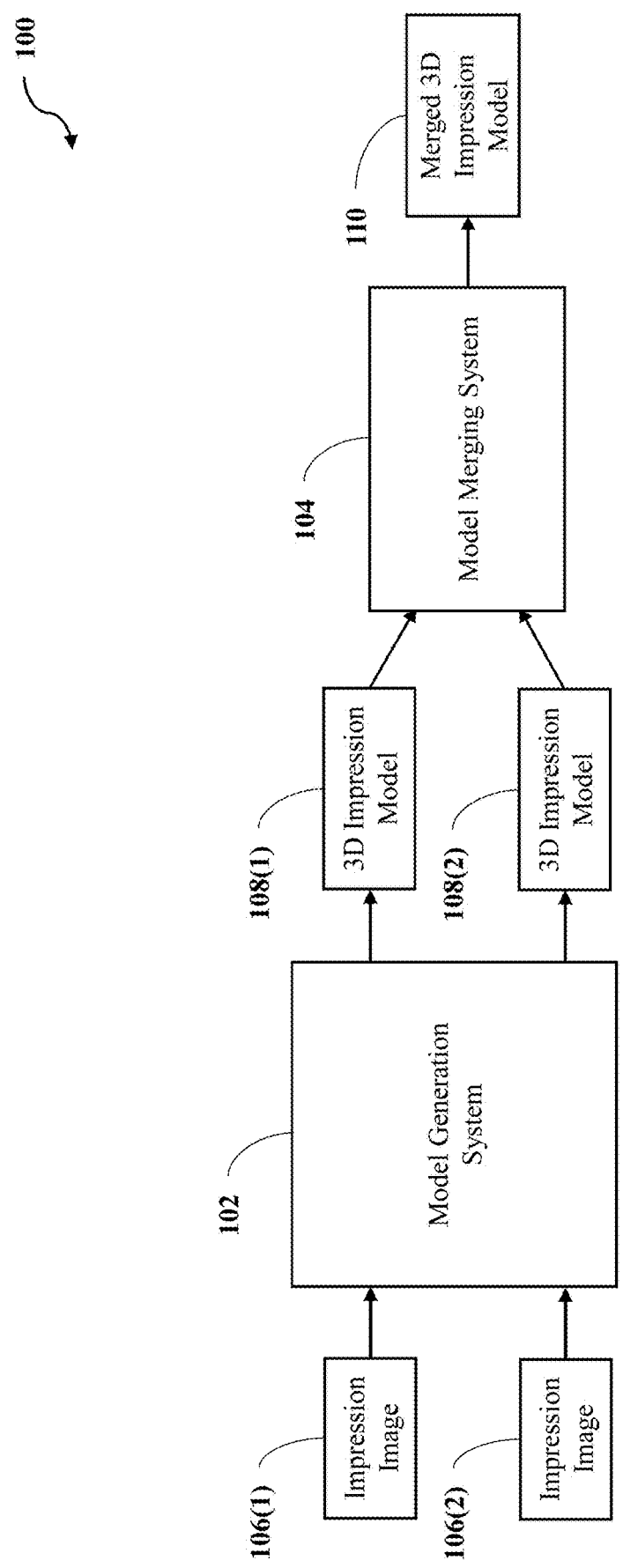
FIG. 1 is a block diagram of a system for generating a three dimensional (3D) model, according to an illustrative embodiment.

Referring now to FIG. 1, a system 100 for generating a three dimensional (3D) model is shown according to an illustrative embodiment. The system 100 is shown to include a model generation system 102 and a model merging system 104. The model generation system 102 (including the components, elements, and aspects thereof) is described in greater detail below with respect to FIG. 2-FIG. 19. The model merging system 104 (including the components, elements, and aspects thereof) is described in greater detail below with respect to FIG. 20-FIG. 30. As a brief overview, the model generation system 102 may be configured to receive an image (e.g., a 2D image) 106, and produce, determine, output, provide, or otherwise generate a 3D model 108 based on the image 106. As shown in FIG. 1, the model generation system 102 may be configured to receive a plurality of images 106 (e.g., a first image 106(1) and a second image 106(2)). The images 106 may be images 106 of a dental impression. In some embodiments, the first and second images 106 may be images 106 of the same dental impression (e.g., a single dental impression of a dental arch). In some embodiments, the first and second images 106 may be images 106 of separate dental impressions of the same dental arch (e.g., a first image 106(1) of a first dental impression of a dental arch, and a second image 106(2) of a second dental impression of the dental arch). The images 106 can include any number or combination of a 2D photograph of a dental impression, a 2D photograph of teeth of the user, a 3D scan of a dental impression, or a 3D scan of teeth of the user. As described in greater detail below, the model generation system 102 may be configured to generate a first 3D impression model 108(1) based on the first image 106(1) and a second 3D impression model 108(2) based on the second image 106(2). The model merging system 104 may be configured to merge the first and second 3D impression models 108(1), 108(2) to form a merged (or composite) 3D impression model 110.

Referring now to FIG. 2, a system 200 for generating a three dimensional (3D) model is shown according to an illustrative embodiment. The system 200 (also referred to herein as a model generation system 200) is shown to include a pre-trained image detector 202 and a model generation engine 204. As described in greater detail below, the pre-trained image detector 202 is configured to generate an image feature map from one or more images 206 of a dental impression of a dental arch of a user. The model generation engine 204 is configured to generate a 3D model using the one or more images 206. The model generation engine 204 includes a long short-term memory (LSTM) encoder 208 configured to compute a probability of each feature of the image feature map using one or more weights. The model generation engine 204 includes an output engine 210 configured to generate a point cloud using data from the LSTM encoder 208. The model generation engine 204 includes a point cloud feature extractor 212 configured to determine features from the point cloud generated by the output engine 210. The model generation engine 204 includes an LSTM decoder 214 configured to determine a difference between features from the point cloud and corresponding probabilities of features of the image feature map. The LSTM encoder 208 trains the one or more weights for computing the probability based on the difference determined by the LSTM decoder 214. The model generation engine 204 iteratively cycles between the LSTM encoder 208, output engine 210, point cloud feature extractor 112, and LSTM decoder 214 to generate and refine point clouds corresponding to the images 206. At the final iteration, an output engine 210 is configured to generate the 3D model using the final iteration of the point cloud.

The model generation system 200 is shown to include a pre-trained image detector 202. The pre-trained image detector 202 may be any device(s), component(s), application(s), element(s), script(s), circuit(s), or other combination of software and/or hardware designed or implemented to generate an image feature map from one or more images 206. The pre-trained image detector 202 may be embodied on a server or computing device, embodied on a mobile device communicably coupled to a server, and so forth. In some implementations, the pre-trained image detector 202 may be embodied on a server which is designed or implemented to generate a 3D model using two dimensional (2D) images. The server may be communicably coupled to a mobile device (e.g., via various network connections).

In some embodiments, the pre-trained image detector 202 may be configured to receive one or more images of a dental impression of a dental arch of a user. For example, a user may administer a dental impression kit (e.g., an at-home dental impression kit) to form a plurality of dental impressions of the user's dental arches (e.g., one or more upper dental impressions of the user's upper dental arch, one or more lower dental impressions of the user's lower dental arch). In some embodiments, another person such as a dentist, orthodontist, other dental professional, or someone that is not a dentist, orthodontist, or dental professional may administer a plurality of dental impressions to the user. In these and other embodiments, the user or the other person may capture one or more images of the dental impressions (e.g. using a camera). In some embodiments, the user or the other person may capture a plurality of images of a single dental impression (such as, for instance, images from different perspectives or images having the same perspective). The user or other person may send, transmit, upload, or otherwise provide the images to the pre-trained image detector 202.

Figure 3A:
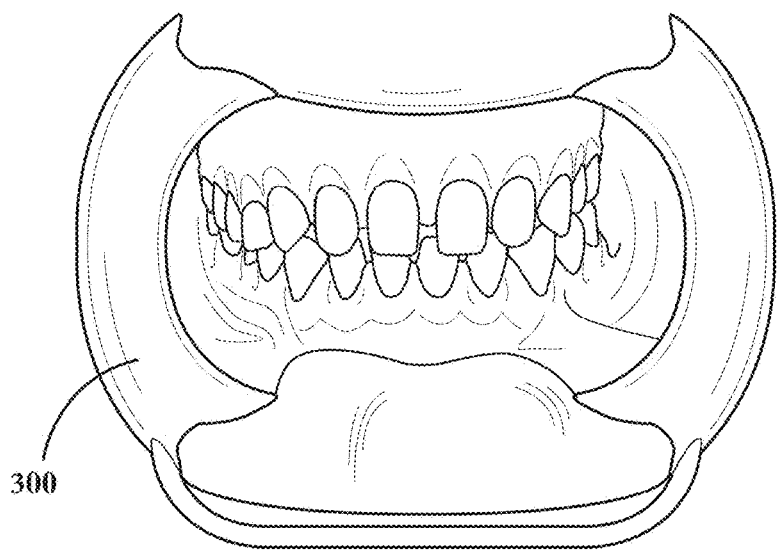
FIG. 3A is an illustration of a first example image of a patient's mouth, according to an illustrative embodiment.
Figure 3B:
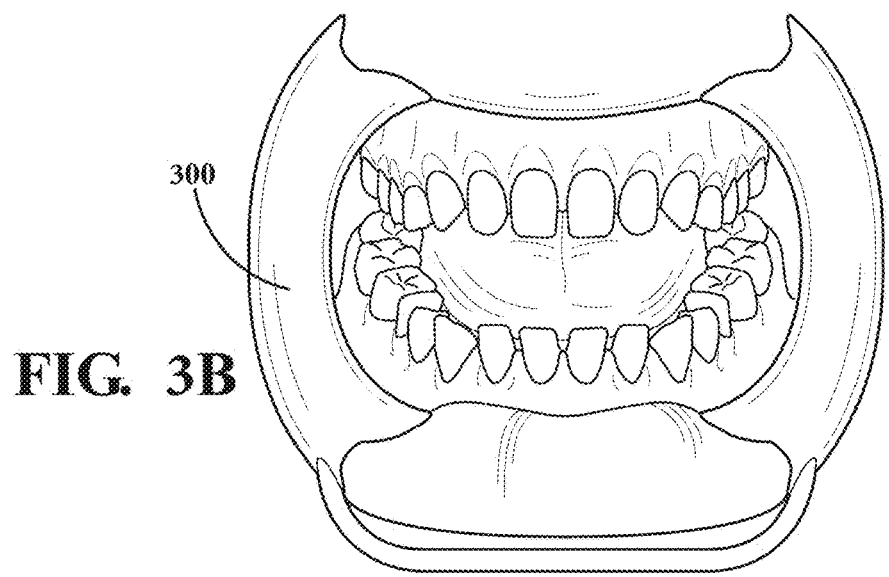
FIG. 3B is an illustration of a second example image of a patient's mouth, according to an illustrative embodiment.
Figure 3C:
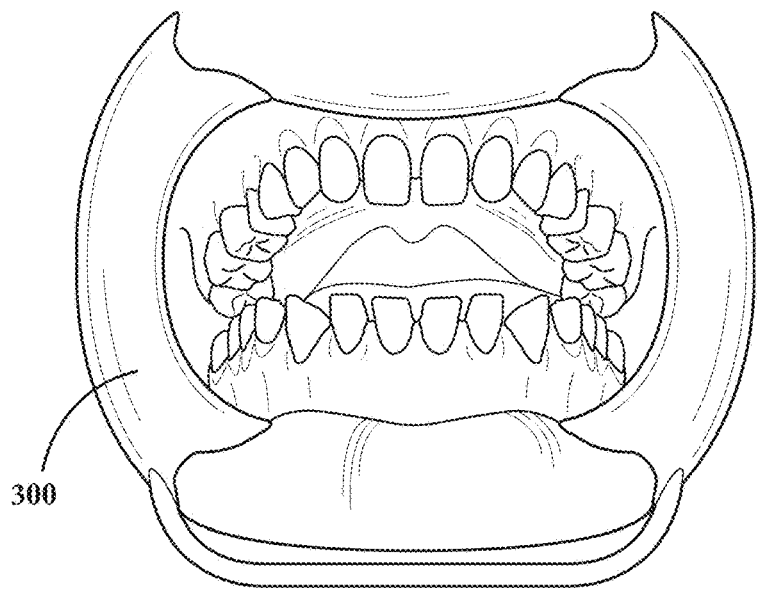
FIG. 3C is an illustration of a third example image of a patient's mouth, according to an illustrative embodiment.

In some embodiments, rather than images of a dental impression, the pre-trained image detector 202 may be configured to receive images of a mouth of a user. Referring now to FIG. 2 and FIG. 3A-FIG. 3C, the pre-trained image detector 202 may be configured to receive one or more images 206 of a mouth of a user, such as one or more 2D images. Specifically, FIG. 3A-FIG. 3C are illustrations of example images 206 of a user's mouth. The user may capture a first image 206 of a straight on, closed view of the user's mouth by aiming a camera in a straight-on manner perpendicular to the labial surface of the teeth (shown in FIG. 3A), a second image 206 of a lower, open view of the user's mouth by aiming a camera from an upper angle down toward the lower teeth (shown in FIG. 3B), and a third image 206 of an upper, open view of the user's mouth by aiming a camera from a lower angle up toward the upper teeth (shown in FIG. 3C). The user may capture images 206 with a dental appliance 300 positioned at least partially within the user's mouth. The dental appliance 300 is configured to hold open the user's lips to expose the user's teeth and gingiva. The user may capture various image(s) 206 of the user's mouth (e.g., with the dental appliance 300 positioned therein). In some embodiments, the user takes two images of their teeth from substantially the same viewpoint (e.g., both from a straight-on viewpoint), or from substantially the same viewpoint but offset slightly.

After capturing the images 106 of a dental impression of the dental arch of the user, the user may upload the images 206 to the pre-trained image detector 202 (e.g., to a website or internet-based portal associated with the pre-trained image detector 202 or model generation system 102, by emailing or sending a message of the images 206 to an email address or phone number or other account associated with the pre-trained image detector 202, and so forth).

The pre-trained image detector 202 is configured to receive the images 206 from the mobile device of the user. The pre-trained image detector 202 may receive the images 206 directly from the mobile device (e.g., by the mobile device transmitting the images 206 via a network connection to a server which hosts the pre-trained image detector 202). The pre-trained image detector 202 may retrieve the images 206 from a storage device (e.g., where the mobile device stored the images 206 on the storage device, such as a database or a cloud storage system). In some embodiments, the pre-trained image detector 202 is configured to score the images 206. The pre-trained image detector 202 may generate a metric which identifies the overall quality of the image. The pre-trained image detector 202 may include a Blind/Referenceless Image Spatial Quality Evaluator (BRISQUE). The BRISQUE is configured to generate an image score between a range (e.g., between 0-100, for instance, with lower scores being generated for images having higher quality). The BRISQUE may be configured to generate the image score based on, for example, the measured pixel noise, image distortion, and so forth, to objectively evaluate the image quality. Where the image score does not satisfy a threshold, the pre-trained image detector 202 may be configured to generate a prompt for the user which directs the user to re-take one or more of the images 206.

Figure 4:
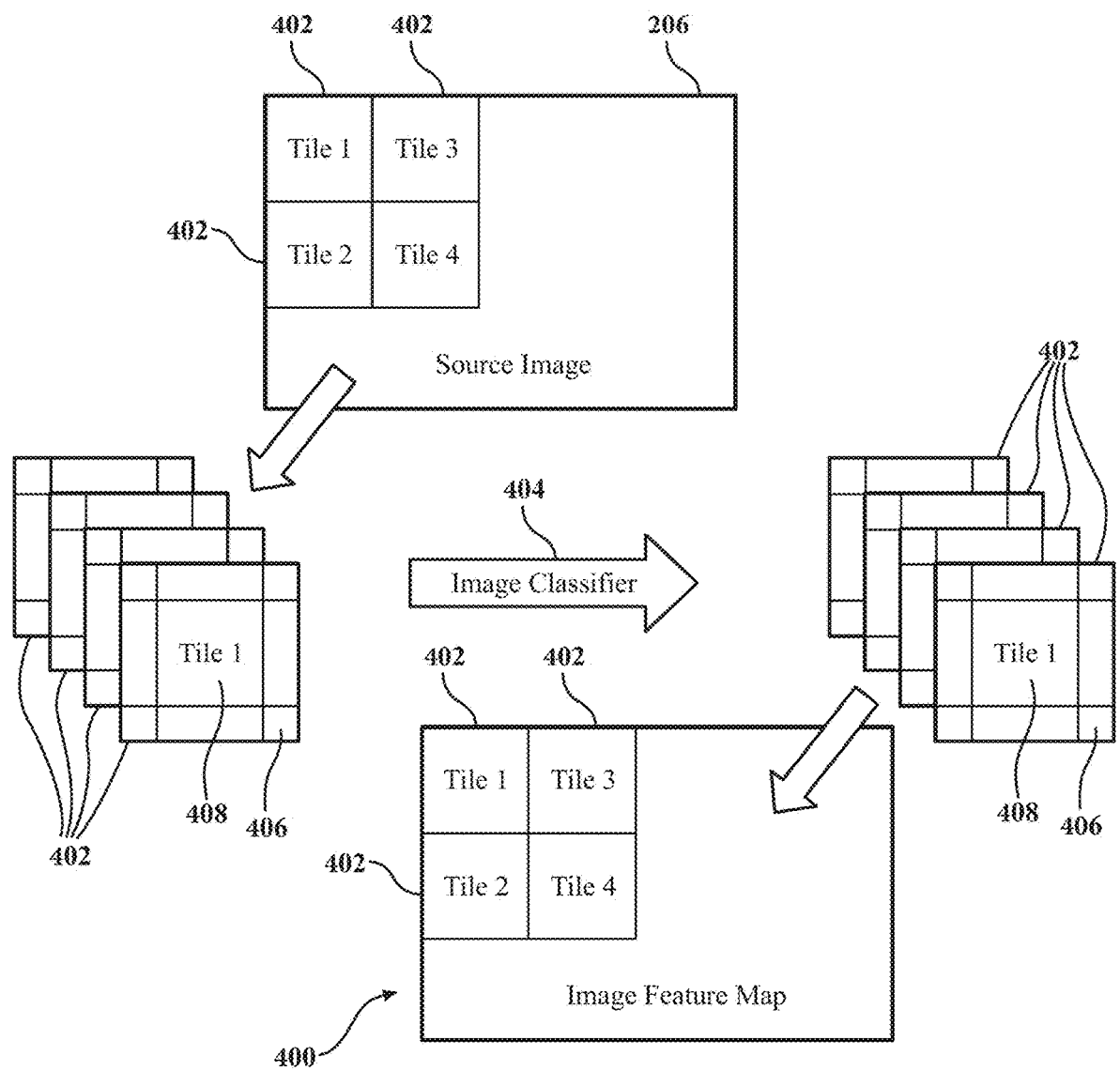
FIG. 4 is a block diagram of an image feature map generated by the system of FIG. 2, according to an illustrative embodiment.

Referring now to FIG. 2 and FIG. 4, the pre-trained image detector 202 is configured to process the image(s) 206 to generate an image feature map 400. Specifically, FIG. 4 is a block diagram of an image feature map 400 corresponding to one of the image(s) 206 received by the pre-trained image detector 202. The pre-trained image detector 202 may be configured to process images 206 received from the mobile device of the user to generate the image feature map 400. In some implementations, the pre-trained image detector 202 is configured to break down, parse, or otherwise segment the images 206 into a plurality of portions. In some implementations, the pre-trained image detector 202 is configured to segment the images 206 into a plurality of tiles 402. Each tile 402 corresponds to a particular portion, section, or region of a respective image 206. In some instances, the tiles 402 may have a predetermined size or resolution. For instance, the tiles 402 may have a resolution of 512 pixels×512 pixels (though the tiles 402 may have different sizes or resolutions). The tiles 402 may each be the same size, or some tiles 402 may have a different size than other tiles 402. In some embodiments, the tiles 402 may include a main portion 406 (e.g., located at or towards the middle of the tile 402) and an overlapping portion 408 (e.g., located along the perimeter of the tile 402). The main portion 406 of each tile 402 may be unique to each respective tile 402. The overlapping portion 408 may be a common portion shared with one or more neighboring tiles 402. The overlapping portion 408 may be used by the pre-trained image detector 202 for context in extracting features within the dental impressions (e.g., tooth size, tooth shape, tooth location, tooth orientation, crown size, crown shape, gingiva location, gingiva shape or contours, tooth-to-gingiva interface location, interproximal region location, and so forth) from the main portion of the tile 402.

The pre-trained image detector 202 is configured to determine, identify, or otherwise extract one or more features from the tiles 402. In some implementations, the pre-trained image detector 202 includes an image classifier neural network 304 (also referred to herein as an image classifier 404). The image classifier 404 may be implemented using a neural network similar to the neural network 500 shown in FIG. 5 and subsequently described. For instance, the image classifier 404 may include an input layer (e.g., configured to receive the tiles 402), one or more hidden layers including various pre-trained weights (e.g., corresponding to probabilities of particular classifications for tiles 402), and an output layer. Each of these layers are described below. The image classifier neural network 304 of the pre-trained image detector 202 is configured to classify each of the tiles 402. The pre-trained image detector 202 may be implemented using various architectures, libraries, or other combination of software and hardware, such as the Mobile-Net architecture, though other architectures may be used (e.g., based on balances between memory requirements, processing speeds, and performance). The pre-trained image detector 202 is configured to process each of the tiles 402 (e.g., piecewise) and stitch together the tiles 402 to generate the image feature map 400. Each classification for a respective tile 402 may correspond to an associated feature within the tile 402. Various examples of classifications include, for instance, a classification of a tooth (e.g., incisors or centrals, canines, premolars or bicuspids, molars, etc.) included in a tile 402, a portion of the tooth included in the tile 402 (e.g., crown, root), whether the gingiva is included in the tile 402, etc. Such classifications may each include corresponding features which are likely to be present in the tile. For instance, if a tile 402 includes a portion of a tooth and a portion of the gingiva, the tile 402 likely includes a tooth-to-gingiva interface. As another example, if a tile 402 includes a molar which shows the crown, the tile 402 likely includes a crown shape, crown size, etc.

In some implementations, the pre-trained image detector 202 is configured to classify each of the tiles 402. For instance, the output from the image classifier 404 may be a classification (or probability of a classification) of the corresponding tile 402 (e.g., provided as an input to the image classifier 404). In such implementations, the image feature map 400 may include each of the tiles 402 with their corresponding classifications. The pre-trained image detector 202 is configured to construct the image feature map 400 by stitching together each of the tiles 402 with each tile 402 including their respective classification. In this regard, the pre-trained image detector 202 is configured to re-construct the images 206 by stitching together the tiles 402 to form the image feature map 400, with the image feature map 400 including the tiles 402 and corresponding classifications. The pre-trained image detector 202 is configured to provide the image feature map 400 as an input to a model generation engine 204. In some implementations, the image feature map 400 generated by the pre-trained image detector 202 may be a compressed filed (e.g., zipped or other format). The pre-trained image detector 202 may be configured to format the image feature map 400 into a compressed file for transmission to the model generation engine 204. The model generation engine 204 may be configured to parse the image feature map 400 for generating a point cloud corresponding to the image(s) 106, as described in greater detail below.

The model generation system 200 is shown to include a model generation engine 204. The model generation engine 204 may be any device(s), component(s), application(s), element(s), script(s), circuit(s), or other combination of software and/or hardware designed or implemented to generate a three-dimensional (3D) model of a user's dental arch from one or more images 206 of the user's dentition. The model generation engine 204 is configured to generate the 3D model using a plurality of images 206 received by the pre-trained image detector 202 (e.g., from a mobile device of the user). The model generation engine 204 may include a processing circuit including one or more processors and memory. The memory may store various instructions, routines, or other programs that, when executed by the processor(s), cause the processor(s) to perform various tasks relating to the generation of a 3D model. In some implementations, various subsets of processor(s), memory, instructions, routines, libraries, etc., may form an engine. Each engine may be dedicated to performing particular tasks associated with the generation of a 3D model. Some engines may be combined with other engines. Additionally, some engines may be segmented into a plurality of engines.

The model generation engine 204 is shown to include a feature map reading engine 216. The feature map reading engine 216 may be any device(s), component(s), application(s), element(s), script(s), circuit(s), or other combination of software and/or hardware designed or implemented to read features from an image feature map 400. The feature map reading engine 216 may be designed or implemented to format, re-format, or modify the image feature map 400 received from the pre-trained image detector 202 for use by other components of the model generation engine 204. For instance, where the output from the pre-trained image detector 202 is a compressed file of the image feature map 400, the feature map reading engine 216 is configured to decompress the file such that the image feature map 400 may be used by other components or elements of the model generation engine 204. In this regard, the feature map reading engine 216 is configured to parse the output received from the pre-trained image detector 202. The feature map reading engine 216 may parse the output to identify the tiles 402, the classifications of the tiles 402, features corresponding to the classifications of the tiles 402, etc. The feature map reading engine 216 is configured to provide the image feature map 400 as an input to an LSTM encoder 208, as described in greater detail below.

Figure 5:
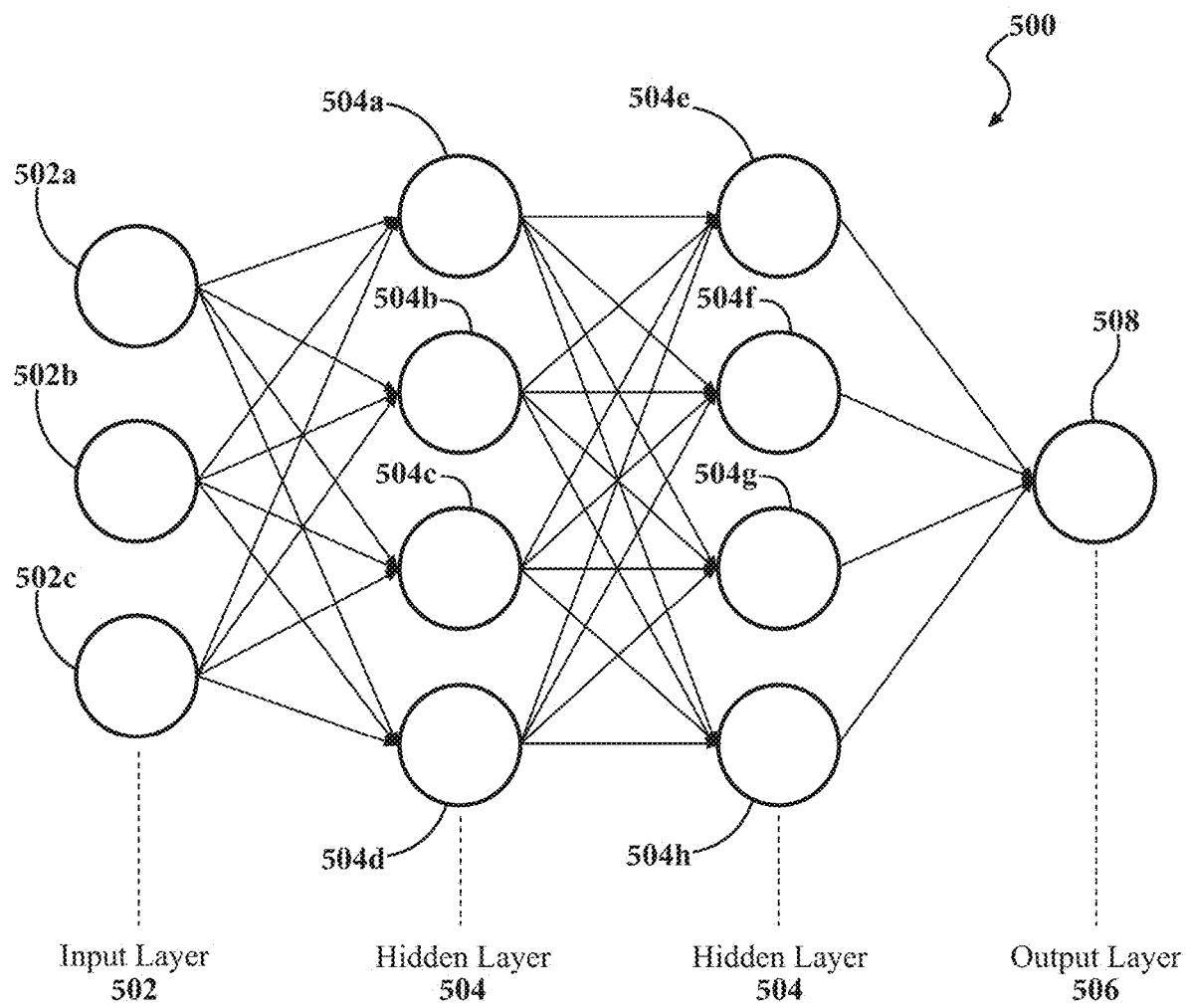
FIG. 5 is a block diagram of a neural network which may be implemented within one or more of the components of FIG. 2, according to an illustrative embodiment.

Referring now to FIG. 2 and FIG. 5, the model generation engine 204 is shown to include an LSTM encoder 208 and LSTM decoder 214. Specifically, FIG. 5 is a block diagram of an implementation of a neural network 500 which may implement various components, features, or aspects within the LSTM encoder 208 and/or LSTM decoder 214. The LSTM encoder 208 may be any device(s), component(s), application(s), element(s), script(s), circuit(s), or other combination of software and/or hardware designed or implemented to compute a probability for each feature of the image feature map 400 using one or more weights. The LSTM decoder 214 may be any device(s), component(s), application(s), element(s), script(s), circuit(s), or other combination of software and/or hardware designed or implemented to determine a difference between features from a point cloud and corresponding probabilities of features of the image feature map 400 (e.g., computed by the LSTM encoder 208). The LSTM encoder 208 and LSTM decoder 214 may be communicably coupled to one another such that the outputs of one may be used as an input of the other. The LSTM encoder 208 and LSTM decoder 214 may function cooperatively to refine point clouds corresponding to the images 106, as described in greater detail below.

As shown in FIG. 5, the neural network 500 includes an input layer 502 including a plurality of input nodes 502a-502c, a plurality of hidden layers 504 including a plurality of perception nodes 504a-504h, and an output layer 506 including an output node 508. The input layer 502 is configured to receive one or more inputs via the input nodes 502a-502c (e.g., the image feature map 400, data from the LSTM decoder 214, etc.). The hidden layer(s) 504 are connected to each of the input nodes 502a-502c of the input layer 502. Each layer of the hidden layer(s) 504 are configured to perform one or more computations based on data received from other nodes. For instance, a first perception node 504a is configured to receive, as an input, data from each of the input nodes 502a-502c, and compute an output by multiplying or otherwise providing weights to the input. As described in greater detail below, the weights may be adjusted at various times to tune the output (e.g., probabilities of certain features being included in the tiles 402). The computed output is then provided to the next hidden layer 504 (e.g., to perception nodes 504e-504h), which then compute a new output based on the output from perception node 504a as well as outputs from perception nodes 504b-504d. In the neural network implemented in the LSTM encoder 208, for instance, the hidden layers 504 may be configured to compute probabilities of certain features in the images 206 of the user's dentition based on the image feature map 400 and data from the LSTM decoder 214, as described in greater detail below. For instance, the hidden layers 504 may be configured to compute probabilities of features, such as tooth size, tooth shape, tooth location, tooth orientation, crown size, crown shape, gingiva location, gingiva shape or contours, tooth-to-gingiva interface location, interproximal region location, and so forth. Together, such features describe, characterize, or otherwise define the user's dentition from one or more images of a dental impression of the user's dentition.

The LSTM encoder 208 is configured to compute a probability of each potential feature being present in the images 206. The LSTM encoder 208 is configured to receive the image feature map 400 (e.g., from the pre-trained image detector 202 directly, or indirectly from the feature map reading engine 116). The LSTM encoder 208 may be or include a neural network (e.g., similar to the neural network 500 depicted in FIG. 5) designed or implemented to compute a probability of the potential features in the images 206 using the image feature map 400. The LSTM encoder 208 may be configured to use data from the LSTM decoder 214 and the image feature map 400 for computing a probability of the features within the images 206. Each feature associated with an image (e.g., of a user's dentition) or a tile 402 for an image 206 may have a corresponding probability. The probability may be a probability or likelihood of a particular feature being present within the image 206 or tile 402 (e.g., a probability of a particular tooth size, tooth orientation, tooth-to-gingiva interface location, etc. within the image 206 or tile 402). For instance, neurons of the neural network may be trained to detect and compute a probability for various potential features described above within an image 206. The neurons may be trained using a training set of images and/or tiles and labels corresponding to particular features, using feedback from a user (e.g., validating outputs from the neural network), etc.

As an example, a lateral incisor may have several possible orientations. A neuron of the LSTM encoder 208 may be trained to compute probabilities of the orientation of the lateral incisor relative to a gingival line. The neuron may detect (e.g., based on features from the image feature map 400) the lateral incisor having an orientation extending 45° from the gingival line along the labial side of the dental arch. The LSTM encoder 208 is configured to compute a probability of the lateral incisor having the orientation extending 45° from the gingival line. As described in greater detail below, during subsequent iterations, the neuron may have weights which are further trained to detect the lateral incisor having an orientation extending 60° from the gingival line along the labial side of the dental arch and compute the probability of the lateral incisor having the orientation extending 60° from the gingival line. Through a plurality of iterations, the probabilities of the orientation of the lateral incisor are adjusted, modified, or otherwise trained based on determined orientations and feedback from the LSTM decoder 214. In this regard, the neurons of the LSTM encoder 208 have weights which are tuned, adjusted, modified, or otherwise trained over time to have both a long term memory (e.g., through training of the 45° orientation in the example above) and short term memory (e.g., through training of the 60° orientation in the example above).

As such, the neurons are trained to detect that a tooth may have multiple possible features (e.g., a tooth may have an orientation of 45° or 60°, or other orientations detected through other iterations). Such implementations and embodiments provide for a more accurate overall 3D model which more closely matches the dentition of the user by providing an LSTM system which is optimized to remember information from previous iterations and incorporate that information as feedback for training the weights of the hidden layer 504 of the neural network, which in turn generates the output (e.g., via the output layer 506), which is used by the output engine 210 for generating the output (e.g., the 3D model). In some implementations, the LSTM encoder 208 and LSTM decoder 214 may be trained with training sets (e.g., sample images). In other implementations, the LSTM encoder 208 and LSTM decoder 214 may be trained with images received from users (e.g., similar to images 206). In either implementation, the LSTM encoder 208 and LSTM decoder 214 may be trained to detect a large set of potential features within images of a user's dental arches (e.g., various orientation, size, etc. of teeth within a user's dentition). Such implementations may provide for a robust LSTM system by which the LSTM encoder 208 can compute probabilities of a given image containing certain features.

Referring back to FIG. 2, the LSTM encoder 208 is configured to generate an output of a plurality of probabilities of each feature based on the input (e.g., the image feature map 400 and inputs from the LSTM decoder 214 described in greater detail below) and weights from the neural network of the LSTM encoder 208. The output layer 506 of the neural network corresponding to the LSTM encoder 208 is configured to output at least some of the probabilities computed by the hidden layer(s) 504. The output layer 506 may be configured to output each of the probabilities, a subset of the probabilities (e.g., the highest probabilities, for instance), etc. The output layer 506 is configured to transmit, send, or otherwise provide the probabilities to a write decoder 218.

The write decoder 218 may be any device(s), component(s), application(s), element(s), script(s), circuit(s), or other combination of software and/or hardware designed or implemented to maintain a list of each of the computed probabilities by the LSTM encoder 208. The write decoder 218 is configured to receive the output from the LSTM encoder 208 (e.g., from the output layer 506 of the neural network corresponding to the LSTM encoder 208). In some implementations, the write decoder 218 maintains the probabilities in a ledger, database, or other data structure (e.g., within or external to the system 100). As probabilities are recomputed by the LSTM encoder 208 during subsequent iterations using updated weights, the write decoder 218 may update the data structure to maintain a list or ledger of the computed probabilities of each feature within the images 206 for each iteration of the process.

The output engine 210 may be any device(s), component(s), application(s), element(s), script(s), circuit(s), or other combination of software and/or hardware designed or implemented to generate a point cloud 600. FIG. 6A-FIG. 6C are illustrations of an example point cloud 600 overlaid on an upper dental arch 604A and a lower dental arch 604B, and a perspective view of the point cloud 600 for the upper and lower dental arch aligned to one another, respectively. The point clouds 600 shown in FIG. 6A-FIG. 6C are generated by the output engine 210. The output engine 210 may be configured to generate the point cloud 600 using the image(s) 206 received by the pre-trained image detector 202. As described in greater detail below, the output engine 210 may be configured to generate a point cloud 600 of a dental arch of the user using probabilities of features within one or more of the images 206 of a dental impression of the dental arch. In some instances, the output engine 210 may be configured to generate a point cloud 600 of a dental arch using probabilities of features within one of the images 206. For instance, the output engine 210 may be configured to generate a point cloud 600 of an upper dental arch 604A using an image of an upper open view of the upper dental arch of the user (e.g., such as the image shown in FIG. 2C). In some instances, the output engine 210 may be configured to generate a point cloud 600 of the upper dental arch 604A using two or more images (e.g., the images shown in FIG. 2B and FIG. 2C, the images shown in FIG. 2A-FIG. 2C, or further images). In some instances, the output engine 210 may be configured to generate a point cloud 600 of the lower dental arch 604B using one image (e.g., the image shown in FIG. 2A), a plurality of images (e.g., the images shown in FIG. 2A-FIG. 2B, FIG. 2A-FIG. 2C), etc. The output engine 210 may be configured to combine the point clouds 600 generated for the upper and lower dental arch 604A, 504B to generate a point cloud 600, as shown in FIG. 6C, which corresponds to the mouth of the user. The output engine 210 may use each of the images 206 for aligning the point cloud of the upper and lower dental arch 604A, 504B.

The output engine 210 is configured to generate the point cloud 600 based on data from the LSTM encoder 208 via the write decoder 218. The output engine 210 is configured to parse the probabilities generated by the LSTM encoder 208 to generate points 602 for a point cloud 600 which correspond to features within the images 206. Using the previous example, the LSTM encoder 208 may determine that the highest probability of an orientation of a lateral incisor is 45° from the gingival line along the labial side. The output engine 210 may generate points 602 for the point cloud 600 corresponding to a lateral incisor having an orientation of 45° from the gingival line along the labial side. The output engine 210 is configured to generate points 602 in a 3D space corresponding to features having a highest probability as determined by LSTM encoder 208, where the points 602 are located along an exterior surface of the user's dentition. In some instances, the output engine 210 may generate the points 602 at various locations within a 3D space which align with the highest probability features of the image(s)

206. Each point 602 may be located in 3D space at a location which maps to locations of features in the images. As such, the output engine 210 may be configured to generate points 602 for the point cloud 600 which match the probability of features in the images 206 (e.g., such that the points 602 of the point cloud 600 substantially match a contour of the user's dentition as determined based on the probabilities). The output engine 210 is configured to provide the point cloud 600 to the point cloud feature extractor 212.

The point cloud feature extractor 212 may be any device(s), component(s), application(s), element(s), script(s), circuit(s), or other combination of software and/or hardware designed or implemented to determine one or more features within a point cloud 600. The point cloud feature extractor 212 may be configured to compute, extract, or otherwise determine one or more features from the point cloud 600 to generate an image feature map (e.g., similar to the image feature map received by the LSTM encoder 208). The point cloud feature extractor 212 may leverage one or more external architectures, libraries, or other software for generating the image feature map from the point cloud 600. In some implementations, the point cloud feature extractor 212 may leverage the PointNet architecture to extract feature vectors from the point cloud 600. In this regard, the images 206 are used (e.g., by the pre-trained image detector 102) for generating an image feature map 400, which is used (e.g., by the LSTM encoder 208 and output engine 210) to generate a point cloud 600, which is in turn used (e.g., by the point cloud feature extractor 212) to extract features. The point cloud feature extractor 212 is configured to transmit, send, or otherwise provide the extracted features from the point cloud 600 to the LSTM decoder 214.

The LSTM decoder 214 is configured to receive (e.g., as an input) the extracted features from the point cloud feature extractor 212 and the probabilities of features computed by the LSTM encoder 208. The LSTM decoder 214 is configured to compute, based on the extracted features and the probabilities, a difference between the output from the LSTM encoder 208 and the point cloud 600. In some implementations, the LSTM decoder 214 is configured to compute a loss function using the extracted features from the point cloud 600 and the corresponding probabilities of each feature from the image feature map 400. The LSTM decoder 214 may be configured to determine which features extracted from the point cloud 600 correspond to features within the image feature map 400. The LSTM decoder 214 may determine which features correspond to one another by comparing each feature (e.g., extracted from the point cloud 600 and identified in the image feature map 400) to determine which features most closely match one another. The LSTM decoder 214 may determine which features correspond to one another based on coordinates for points of the point cloud 600 and associated location of tiles 402 in the image feature map 400 (e.g., the coordinates residing within one of the tiles 402, particular regions of the 3D space in which the points correspond to specific tiles 402, and so forth).

Once two features are determined (e.g., by the LSTM decoder 114) to correspond to one another, the LSTM decoder 214 compares the corresponding features to determine differences. For instance, where the feature is determined to be an orientation of a specific tooth, the LSTM decoder 214 is configured to compare the orientation of the feature from the image(s) 206 and the orientation from the point cloud 600. The LSTM decoder 214 is configured to compare the orientations to determine whether the feature represented in the point cloud 600 matches the feature identified in the image(s) 206 (e.g., the same orientation). In some implementations, the LSTM decoder 214 is configured to determine the differences by computing a loss function (e.g., using points 602 from the point cloud 600 and corresponding features from the image feature map 400). The loss function may be a computation of a distance between two points (e.g., a point 602 of the point cloud 600 and corresponding features from the image feature map 400). As the value of the loss function increases, the point cloud 600 correspondingly is less accurate (e.g., because the points 602 of the point cloud 600 do not match the features of the image feature map 400). Correspondingly, as the value of the loss function decreases, the point cloud 600 is more accurate (e.g., because the points 602 of the point cloud 600 more closely match the features of the image feature map 400). The LSTM decoder 214 may provide the computed loss function, the differences between the features, etc. to the LSTM encoder 208 (e.g., either directly or through the read decoder 120) so that the LSTM encoder 208 adjusts, tunes, or otherwise modifies weights for computing the probabilities based on feedback from the LSTM decoder 214. In implementations in which the LSTM decoder 214 is configured to provide data to the LSTM encoder 208 through the read decoder 120, the read decoder 220 (e.g., similar to the write decoder 118) is configured to process the data from the LSTM decoder 214 to record the differences for adjustment of the weights for the LSTM encoder 208.

During subsequent iterations, the LSTM encoder 208 is configured to modify, refine, tune, or otherwise adjust the weights for the neural network 500 based on the feedback from the LSTM decoder 214. The LSTM encoder 208 may then compute new probabilities for features in the images 106, which is then used by the output engine 210 for generating points for a point cloud 600. As such, the LSTM decoder 214 and LSTM encoder 208 cooperatively adjust the weights for forming the point clouds 600 to more closely match the point cloud 600 to the features identified in the images 206. In some implementations, the LSTM encoder 208 and LSTM decoder 214 may perform a number of iterations. The number of iterations may be a predetermined number of iterations (e.g., two iterations, five iterations, 10 iterations, 50 iterations, 200 iterations, 200 iterations, 500 iterations, 1,000 iterations, 2,000 iterations, 5,000 iterations, 8,000 iterations, 10,000 iterations, 100,000 iterations, etc.). In some implementations, the number of iterations may change between models generated by the model generation system 200 (e.g., based on a user selection, based on feedback, based on a minimization or loss function or other algorithm, etc.). For instance, where the LSTM decoder 214 computes a loss function based on the difference between the features from the point cloud 600 and probabilities computed by the LSTM encoder 208, the number of iterations may be a variable number depending on the time for the loss function to satisfy a threshold. Hence, the LSTM encoder 208 may iteratively adjust weights based on feedback from the LSTM decoder 214 until the computed values for the loss function satisfy a threshold (e.g., an average of 0.05 mm, 0.1 mm, 0.15 mm, 0.2 mm, 0.25 mm, etc.). Following the final iteration, the output engine 210 is configured to provide the final iteration of the point cloud 600.

In some implementations, the output engine 210 is configured to merge the point cloud 600 with another point cloud or digital model of the user's dentition. For instance, the output engine 210 may be configured to generate a merged model from a first digital model (e.g., the point cloud 600) and a second digital model (e.g., a scan of a user's dentition, a scan of a dental impression of the user's dentition, etc.). In some implementations, the output engine 210 is configured to merge the point cloud 600 with another 3D model using at least some aspects as described in U.S. patent application Ser. No. 16/548,712, filed Aug. 22, 2019, the contents of which are incorporated herein by reference in its entirety.

The point cloud 600 may be used to manufacture a dental aligner specific to the user and configured to reposition one or more teeth of the user. The output engine 210 may be configured to provide the point cloud 600 to one or more external systems for generating the dental aligner. For instance, the output engine 210 may transmit the point cloud 600 to a 3D printer to print a positive mold using the point cloud. A material may be thermoformed to the positive mold to form a shape of a dental aligner, and the dental aligner may be cut from the positive model. As another example, the output engine 210 may transmit the point cloud 600 to a 3D printer to directly print a dental aligner.

Figure 7:
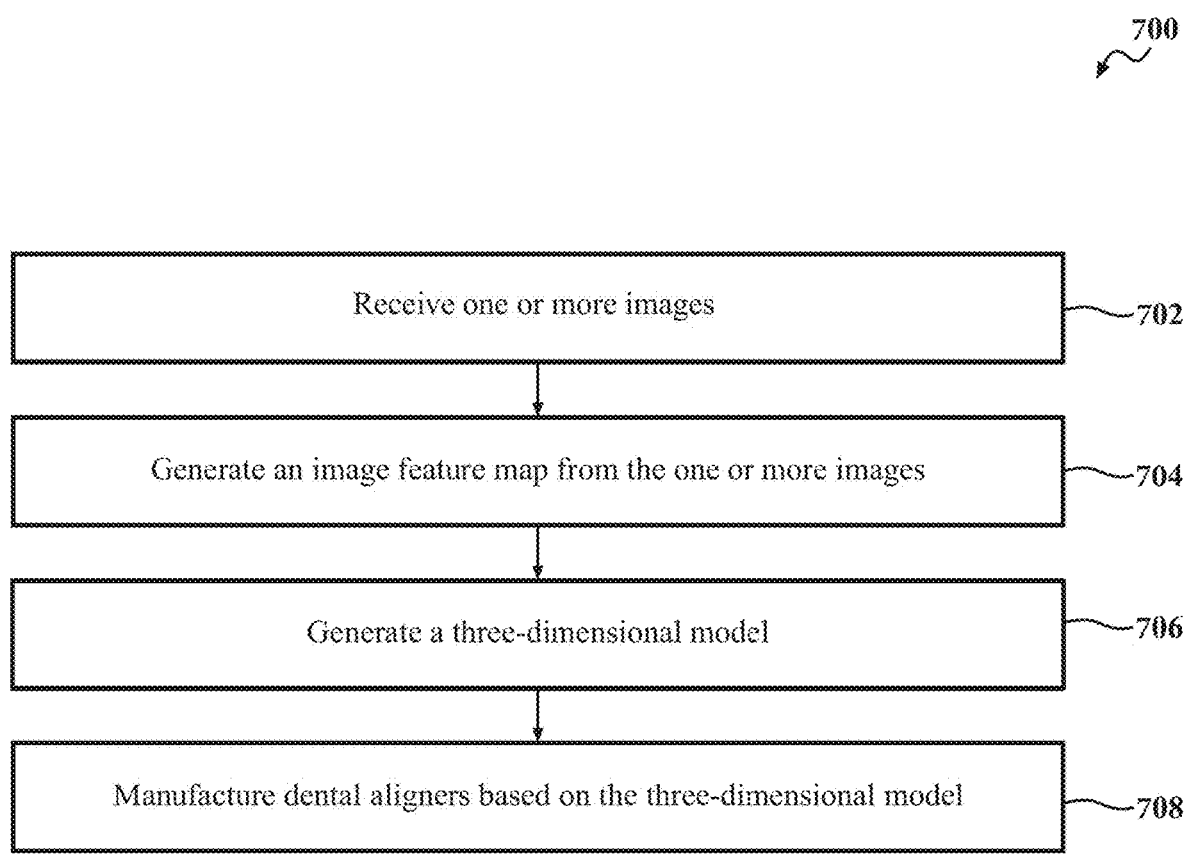
FIG. 7 is a diagram of a method of generating a 3D model from one or more 2D images, according to an illustrative embodiment.

Referring now to FIG. 7, a diagram of a method 700 of generating a three-dimensional model from one or more two-dimensional images is shown according to an illustrative embodiment. The method 700 may be implemented by one or more of the components described above with reference to FIG. 2-FIG. 6C. As an overview, at step 702, a model generation system 200 receives one or more images 206 of a dental impression of a dental arch of a user. At step 704, the model generation system 200 generates a point cloud 600 from the one or more images 206. At step 706, the model generation system generates a three-dimensional (3D) model from the point cloud 600. At step 708, dental aligners are manufactured based on the 3D model.

At step 702, a model generation system 200 receives one or more images 206 of a dental impression of a dental arch of a user. The images 206 may be captured by the user following the user administering contents of a dental impression kit (such as an at-home dental impression kit). In some embodiments, the images 206 may be captured by a dental professional following the dental professional administering dental impressions of the user. In some embodiments, the images 206 may be captured of a dental impression from a plurality of different perspectives. In some embodiments, the images 206 may include a plurality of images of a plurality of dental impressions of the same dental arch of the user (as described above with respect to FIG. 1). The user may capture the image(s) 206 on their mobile device or any other device having a camera. The user may upload, transmit, send, or otherwise provide the image(s) 206 to the model generation system 200 (e.g., to an email or account associated with the model generation system 102, via an internet-based portal, via a website, etc.). The model generation system 200 receives the image(s) 206 (e.g., from the mobile device of the user). The model generation system 200 uses the image(s) 206 for generating a 3D model of the user's mouth, as described in greater detail below.

At step 704, the model generation system 200 generates a point cloud 600 from the one or more images. In some embodiments, the model generation system 200 generates the point cloud 600 based on data from the one or more images 206 of the dental impression of the dental arch of the user (e.g., received at step 702). The model generation system 200 may parse the images 206 to generate image feature maps 400. The model generation system 200 may compute probabilities of features of the image feature map 400. The model generation system 200 may generate a point cloud 600 using the probabilities of the features of the image feature map 400. The model generation system 200 may determine features of the point cloud 600. The model generation system 200 may determine differences between the features of the point cloud and corresponding probabilities of the features of the image feature map. The model generation system 200 may train weights for computing the probabilities. The model generation system 200 may iteratively refine the point cloud 600 until a predetermined condition is met. Various aspects in which the model generation system 200 generates the point cloud 600 are described in greater detail below with reference to FIG. 8.

At step 706, the model generation system 200 generates a three-dimensional (3D) model. The model generation system 200 generates a 3D model of the mouth of the user (e.g., a 3D model of the upper and lower dental arch of the user). In some embodiments, the model generation system 200 generates a first 3D model of an upper dental arch of the user, and a second 3D model of a lower dental arch of the user. The model generation system 200 may generate the 3D models using the generated point cloud 600 (e.g., at step 704). In some embodiments, the model generation system 200 generates the 3D model by converting a point cloud 600 for the upper dental arch and a point cloud 600 for the lower dental arch into a stereolithography (STL) file, with the STL file being the 3D model. In some embodiments, the model generation system 200 uses the 3D model for generating a merged model (e.g., as described below with respect to FIG. 20-FIG. 30). The model generation system 200 may merge the 3D model generated based on the point cloud 600 (e.g., at step 706) with another 3D model (e.g., with a 3D model generated by scanning the user's dentition, with a 3D model generated by scanning an impression of the user's dentition, with a 3D model generated by scanning a physical model of the user's dentition which is fabricated based on an impression of the user's dentition, etc.) to generate a merged (or composite) model.

At step 708, dental aligner(s) are manufactured based on the 3D model. In some embodiments, a manufacturing system manufactures the dental aligner(s) based at least in part on the 3D model of the mouth of the user. The manufacturing system manufactures the dental aligner(s) by receiving the data corresponding to the 3D model generated by the model generation system 200. The manufacturing system may manufacture the dental aligner(s) using the 3D model generated by the model generation system 200 (e.g., at step 708). The manufacturing system may manufacture the dental aligner(s) by 3D printing a physical model based on the 3D model, thermoforming a material to the physical model, and cutting the material to form a dental aligner from the physical model. The manufacturing system may manufacture the dental aligner(s) by 3D printing a dental aligner using the 3D model. In any embodiment, the dental aligner(s) are specific to the user (e.g., interface with the user's dentition) and are configured to reposition one or more teeth of the user.

Figure 8:
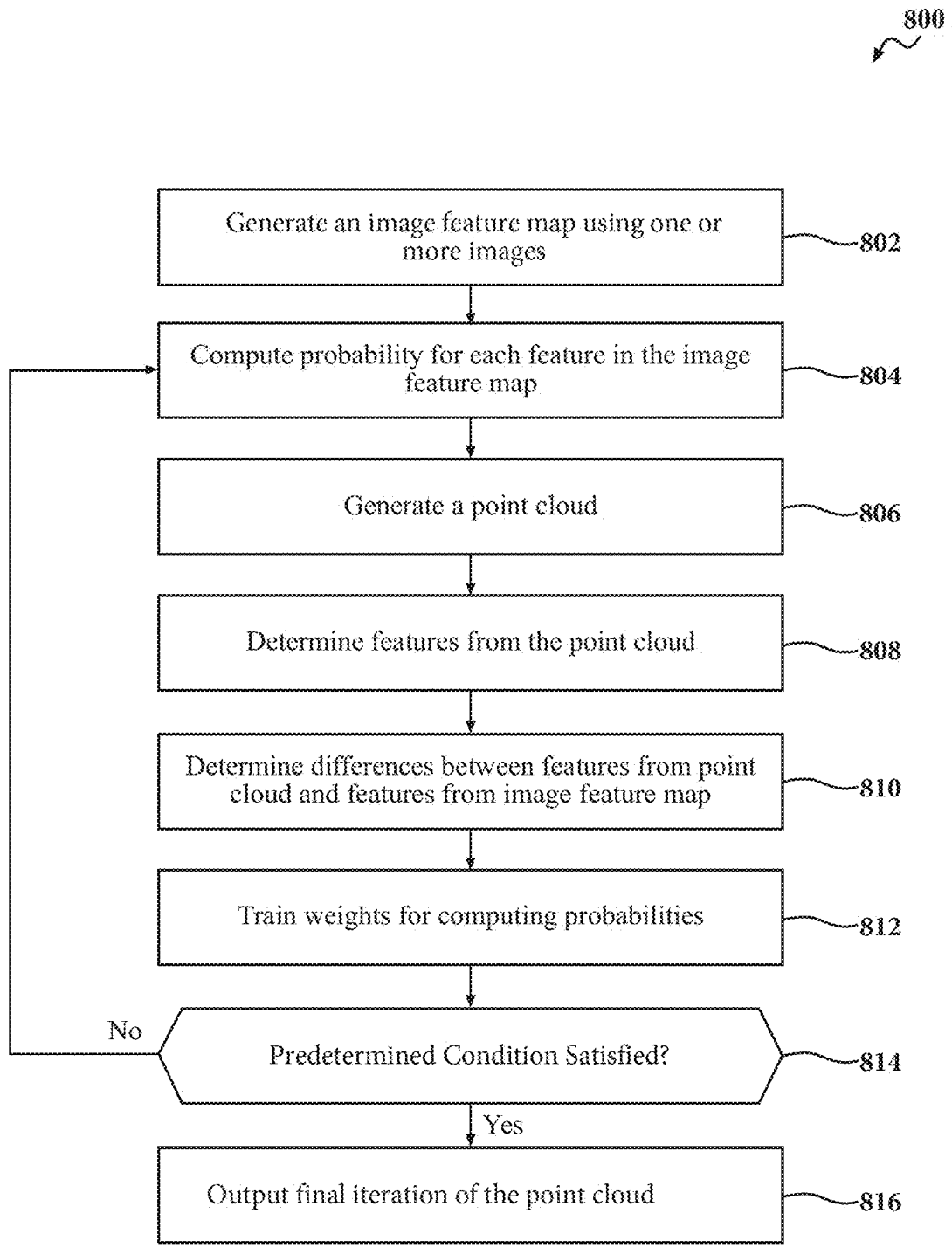
FIG. 8 is a diagram of a method of generating a point cloud from one or more 2D images, according to an illustrative embodiment.

Referring now to FIG. 8, a diagram of a method 800 of generating a point cloud 600 from one or more two-dimensional images 206 is shown according to an illustrative embodiment. The method 800 may be implemented by one or more of the components described above with reference to FIG. 2-FIG. 6C. As an overview, at step 802, the model generation system 200 generates an image feature map 400 using one or more images. At step 804, the model generation system 200 computes a probability of each feature in the image feature map 400. At step 806, the model generation system 200 generates a point cloud 600. At step 808, the model generation system 200 determines features of the point cloud 600. At step 810, the model generation system 200 determines differences between features of the point cloud and features of the image feature map 400. At step 812, the model generation system 200 trains weights for computing probabilities. At step 814, the model generation system 200 determines whether a predetermined condition is satisfied. Where the predetermined condition is not satisfied, the method 800 loops back to step 804. Where the predetermined condition is satisfied, at step 816, the model generation system 200 outputs a final iteration of the point cloud.

At step 802, the model generation system 200 generates an image feature map 400 from the one or more images 206. In some embodiments, a pre-trained image detector 202 of the model generation system 200 generates the image feature map 400 from the image(s) 206 (e.g., received at step 702 of FIG. 7). The image feature map 400 may include a classification of a plurality of portions of the image(s) 206. Each classification may correspond to a feature within the respective portion of the image(s) 206 to be represented in the point cloud.

In some embodiments the pre-trained image detector 202 may receive the image(s) 206 of the dental impression of the dental arch of the user. The pre-trained image detector 202 portions the image(s) 206 received from the mobile device of the user. The pre-trained image detector 202 may portion the image(s) 206 into pre-determined sized portions. For instance, the pre-trained image detector 202 may portion the image(s) 206 into tiles 402. The tiles 402 may be equally sized portions of the image(s) 206. A plurality of tiles 402 corresponding to an image 206 may together form the image 206. The pre-trained image detector 202 may determine a classification of each of the portions of the image(s) 206 (e.g., of each tile 402 corresponding to an image 106). The pre-trained image detector 202 may determine the classification by parsing each portion of the image(s) 206. The pre-trained image detector 202 may parse portions of the image(s) 206 by leveraging one or more architectures, such as the MobileNet architecture. In some implementations, the pre-trained image detector 202 may include an image classifier 404, which may be embodied as a neural network. The image classifier 404 may include an input layer (e.g., configured to receive the tiles 402), one or more hidden layers including various pre-trained weights, and an output layer. The image classifier 404 may classify each of the tiles 402 based on the pre-trained weights. Each classification for a respective tile 402 may correspond to an associated feature. The pre-trained image detector 202 may generate the image feature map 400 using the portions of the image(s) 206 which include their respective classifications. For instance, following the tiles 402 being classified by the image classifier 404, the pre-trained image detector 202 may reconstruct the image(s) 206 as an image feature map 400 (e.g., by stitching together the tiles 402 to form the image feature map 400).

At step 804, the model generation system 200 computes a probability of features in the image feature map 400. In some embodiments, an LSTM encoder 208 of the model generation system 200 computes the probabilities. The LSTM encoder 208 may compute a probability for each feature of the image feature map 400 using one or more weights. The LSTM encoder 208 receives the image feature map 400 (e.g., generated at step 704). The LSTM encoder 208 parses the image feature map 400 to compute probabilities of features present in the image feature map 400. The LSTM encoder 208 may be embodied as a neural network including one or more nodes having weights which are tuned to detect certain features in an image feature map 400. The output of the neural network may be a probability of a corresponding feature in the image feature map. The LSTM encoder 208 may be tuned to detect and compute a probability of the potential features in the images 206 using the image feature map 400.

At step 806, the model generation system 200 generates a point cloud 600. In some embodiments, an output engine 210 of the model generation system 200 may generate the point cloud 600 using the probabilities (e.g., computed at step 802). The output engine 210 generates the point cloud 600 based on data from the LSTM encoder 208. The output engine 210 may generate the point cloud 600 using the probabilities which are highest. For instance, the output engine 210 may generate the point cloud 600 by parsing the data corresponding to the probabilities for each feature of the images 206. Each feature may include a corresponding probability. The output engine 210 may identify the most probable features of the images 206 (e.g., based on which probabilities are highest). The output engine 210 may generate a point cloud 600 using the most probable features of the images 206. The point cloud 600 includes a plurality of points which together define a surface contour of a 3D model. The surface contour may follow a surface of the user's dental arch such that the point cloud 600 matches, mirrors, or otherwise represents the user's dental arch.

At step 808, the model generation system 200 determines features of the point cloud 600. In some embodiments, a point cloud feature extractor 212 of the model generation system 200 determines one or more features from the point cloud 600 generated by the output engine 210 (e.g., at step 806). The point cloud feature extractor 212 may process the point cloud 600 to identify the features from the points of the point cloud 600. The point cloud feature extractor 212 may process the point cloud 600 independent of the probabilities computed by the LSTM encoder 208 and/or the image feature map 400. In this regard, the point cloud feature extractor 212 determines features from the point cloud 600 without feedback from the LSTM encoder 208. The point cloud feature extractor 212 may leverage data from one or more architectures or libraries, such as PointNet architecture, for determining features from the point cloud.

At step 810, the model generation system 200 determines differences between features of the point cloud 600 (e.g., determined at step 808) and the features of the image feature map 400 (e.g., generated at step 802). In some embodiments, an LSTM decoder 214 of the model generation system 200 determines a difference between the features determined by the point cloud feature extractor 212 and corresponding features from the image feature map 400. The LSTM decoder 214 may compare features determined by the point cloud feature extractor 212 (e.g., based on the point cloud 600) and corresponding features from the image feature map 400 (e.g., probabilities of features computed by the LSTM encoder 208). The LSTM decoder 214 may compare the features to determine how accurate the point cloud 600 computed by the output engine 210 is in comparison to the image feature map 400.

In some embodiments, the LSTM decoder 214 may compute a loss function using the features extracted from the point cloud 600 (e.g., by the point cloud feature extractor 112) and corresponding probabilities of each feature of the image feature map 400. The LSTM decoder 214 may determine the difference based on the loss function. The LSTM encoder 208 may train the weights (described in greater detail below) to minimize the loss function computed by the LSTM decoder 214.

At step 812, the model generation system 200 trains weights for computing the probabilities (e.g., used at step 804). In some embodiments, the LSTM encoder 208 of the model generation system 200 trains the one or more weights for computing the probability based on the determined difference (e.g., determined at step 810). The LSTM encoder 208 may tune, adjust, modify, or otherwise train weights of the neural network used for computing the probabilities of the features of the image feature map 400. The LSTM encoder 208 may train the weights using feedback from the LSTM decoder 214. For instance, where the LSTM decoder 214 computes a loss function of corresponding feature(s) of the image feature map 400 and feature(s) extracted from the point cloud 600, the LSTM decoder 214 may provide the loss function value to the LSTM encoder 208. The LSTM encoder 208 may correspondingly train the weights for nodes of the neural network (e.g., for that particular feature) based on the feedback. The LSTM encoder 208 may train the weights of the nodes of the neural network to minimize the loss function or otherwise limit differences between the features of the point cloud 600 and features of the image feature map 400.

At step 814, the model generation system 200 determines whether a predetermined condition is met or satisfied. In some embodiments, the predetermined condition may be a predetermined or pre-set number of iterations in which steps 804-812 are to be repeated. The number of iterations may be set by a user, operator, or manufacturer of the dental aligners, may be trained based on an optimization function, etc. In some embodiments, the predetermined condition may be the loss function satisfying a threshold. For instance, the model generation system 200 may repeat steps 804-812 until the loss function value computed by the LSTM decoder 214 satisfies a threshold (e.g., the loss function value is less than 0.1 mm). Where the model generation system 200 determines the predetermined condition is not satisfied, the method 800 may loop back to step 804. Where the model generation system 200 determines the predetermined condition is satisfied, the method 800 may proceed to step 816.

At step 816, the model generation system 200 outputs the final iteration of the point cloud 600. In some embodiments, the output engine 210 of the model generation system 200 may output the point cloud 600. The output engine 210 may output a point cloud 600 for an upper dental arch of the user and a point cloud 600 for a lower dental arch of the user. Such point clouds 600 may be used for generating a 3D model, which in turn can be used for manufacturing dental aligners for an upper and lower dental arch of the user, as described above in FIG. 7.

Figure 9:
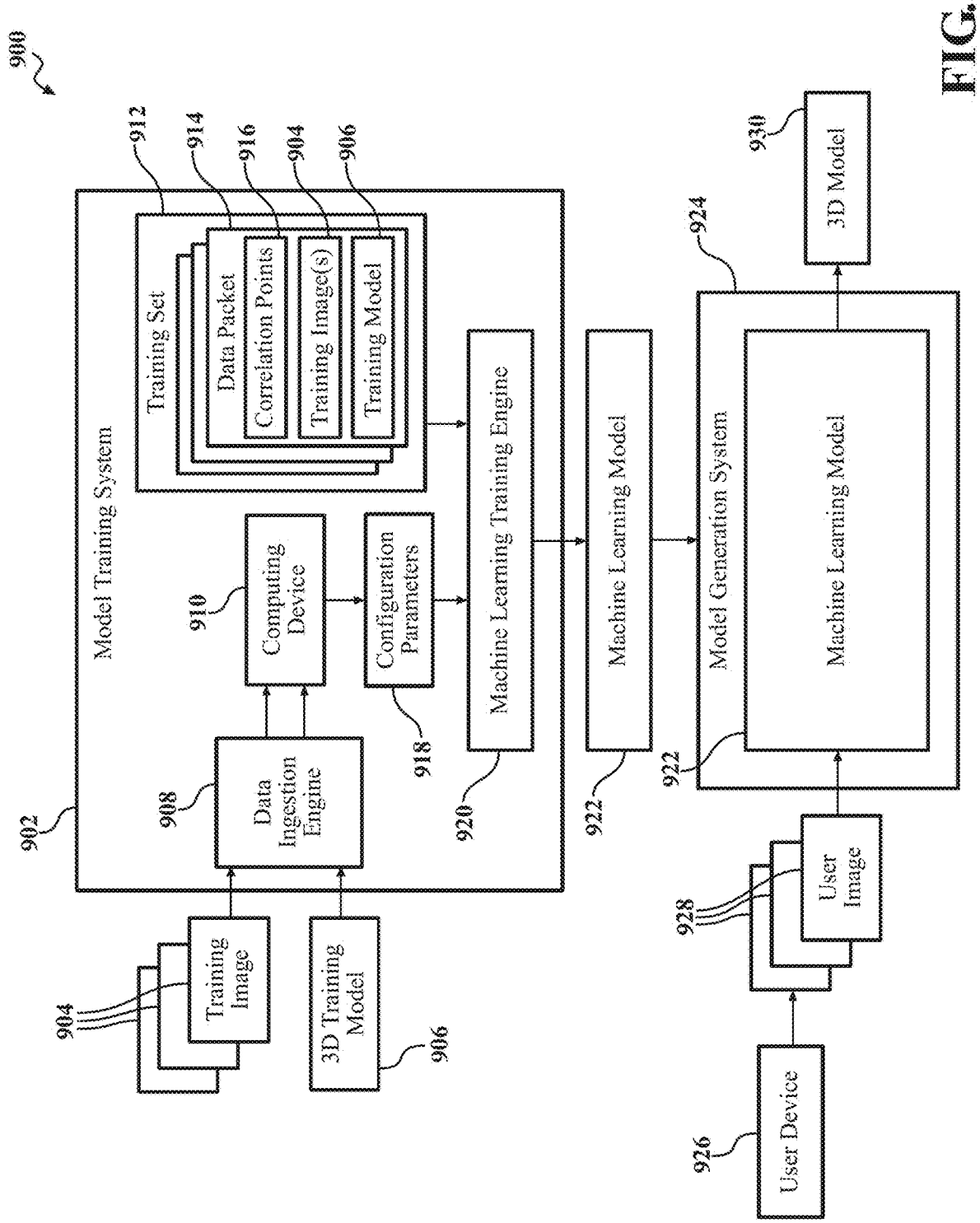
FIG. 9 is a diagram of a system for generating a 3D model from one or more 2D images, according to another illustrative embodiment.

Referring now to FIG. 9, a block diagram of another embodiment of a system 900 for generating a 3D model from one or more 2D images is shown, according to an illustrative embodiment. The system 900 is shown to include a model training system 902 and a model generation system 924. As described in greater detail below with respect to FIG. 9-FIG. 13, the model training system 902 may be configured to train a machine learning model 922 based on a training set 912 including one or more training images 904, a 3D training model 906, and a plurality of correlation points 916 between the images 904 and 3D training model 906. The model generation system 924 may be configured to apply the machine learning model 922 to one or more user images 928 (e.g., received from a user device 926) to generate a 3D model 930. The system 900 may include elements which are similar to those described above with reference to FIG. 2. For example, the model generation system 924 may include the pre-trained image detector 202 configured to process images received from a user. Similarly, the model generation system 924 may include the output engine 210 which is configured to apply the images received from the user to the machine learning model 922 to generate a 3D model 930 (which may be or include a point cloud as described above with reference to FIG. 2-7, may be a standard triangle language (STL) file used for stereolithography, a mesh, or other form of a 3D model).

The system 900 is shown to include a model training system 902. The model training system 902 may be any device(s), component(s), application(s), element(s), script(s), circuit(s), or other combination of software and/or hardware designed or implemented to generate, configure, train, or otherwise provide a machine learning model 922 for generating a 3D model from one or more user images. The model training system 902 may be configured to receive one or more training images 904 and a corresponding 3D training model 906. In some embodiments, the model training system 902 may be configured to receive the training images 904 and 3D training model 906 from a data source that stores a plurality of images and related 3D models. The training images 904 may be images captured by a patient or customer (as described above with reference to FIG. 2-FIG. 3C). The training images 904 may be images of a dental impression captured by a dental professional of a patient or customer when capturing a 3D representation of the patient's dentition (e.g., via a dental impression or a 3D scan of the patient's dentition). The 3D training model 906 may be a 3D representation of a patient's dentition. The 3D training model 906 may be captured by scanning the patient's dentition (e.g., via a 3D scanning device). The 3D training model 906 may be captured by scanning a representation of the patient's dentition (e.g., by scanning a dental impression of the patient's dentition, by scanning a physical model which is cast from a dental impression of the patient's dentition, etc.). Each of the images 904 may correspond to a respective training model 906. For example, for a given 3D training model 906 of a dental arch of a user, the model training system 902 may be configured to receive one or more 2D training images 904 of a dental impression of the dental arch of the user. As such, for a given 3D training model 906, one or more 2D training images 904 and the 3D training model 906 may both represent a common dental arch.

The model training system 902 is shown to include a data ingestion engine 908. The data ingestion engine 908 may be any device(s), component(s), application(s), element(s), script(s), circuit(s), or other combination of software and/or hardware designed or implemented to ingest the training images 904 and the 3D training model 906. In some embodiments, the data ingestion engine 908 may be configured to select a subset of training images 904 for use in training the machine learning model 922. The data ingestion engine 908 may be configured to select the subset of training images 904 based on a determined quality of the images. For example, the data ingestion engine 908 may include one or more aspects or features of the pre-trained image detector 202 described above with reference to FIG. 2. In some embodiments, the data ingestion engine 908 may be configured to ingest a series of training images 904, such as a video including a plurality of frames, with each of the frames being one of the series of training images 904. The data ingestion engine 908 may be configured to select a subset of the series of training images 904 (e.g., based on the determined quality of the frames as described above with respect to FIG. 2) for use in training the machine learning model 922. The data ingestion engine 908 may be configured to select (e.g., automatically) the series of training images 904 to include a plurality of training images 904 having a predetermined perspective. The data ingestion engine 908 may be configured to select the series of training images 904 having the predetermined perspective. The data ingestion engine 908 may be configured to select the series of training images 904 automatically (e.g., using a machine learning model) trained to detect the predetermined perspective in the training images. For example, the machine learning model may be a 2D segmentation model which is configured or trained to automatically identify individual teeth in an image of a dental impression, and determine (e.g., based on the individual teeth represented in the image of the dental impression) whether the image is suitable for including in the training set. In some embodiments, the data ingestion engine 908 may be configured to receive a selection of the training images 904 from a computing device (such as the computing device 910 described in greater detail below). In some embodiments, the data ingestion engine 908 may be configured to receive the training images 904 from a photo capturing application which is configured to capture images which are suitable for the training set.

In some embodiments, the data ingestion engine 908 may be configured to process the 3D training model 906 (e.g., to generate a modified 3D training model). For instance, the 3D training model 906 may be an initial training model which includes data corresponding to a 3D representation of an upper dental arch and a lower dental arch of a patient. As described in greater detail below with reference to FIG. 10 and FIG. 13, the data ingestion engine 908 may be configured to receive the initial training model, and generate a final 3D training model by separating the 3D representation of the upper dental arch from the 3D representation of the lower dental arch, and removing a 3D representation of gingiva in the respective arches such that the final 3D training model includes a 3D representation of a plurality of upper (or lower) teeth.

In some embodiments, the data ingestion engine 908 may be configured to generate a metadata file corresponding to the training images 904 and the associated 3D training model 906. The metadata file may be or include data that correlates or links a set of the training images 904 of a user with the 3D training model 906 of the dentition of the user represented in the set of training images 904. The data ingestion engine 908 may be configured to maintain the metadata file as the training images 904 and associated 3D training model 906 are processed to generate a corresponding data packet 914 (or data point, data package, or other structured data) of the training set 912, as described in greater detail below. In some embodiments, the metadata file may include data corresponding to the training images 904 and/or the device which was used to capture the images. For example, the metadata file may include data corresponding to an image contrast of the training images 904, a focus of the training images 904, a pixel size of the training images 904, a normalization factor of the training images 904, a scaling of the training images 904, a phone or camera type, a phone or camera model, photo orientation, etc. Such data may be used to standardize the training images 904 across the training set 912.

The model training system 902 is shown to include a computing device 910. The computing device 910 may be configured to determine, generate, or otherwise identify correlation points 916 between the training images 904 and the 3D training model 906. The correlation points 916 may be points that are commonly represented in both the training images 904 and the 3D training model 906. For example, the correlation points 916 may be a point located on a crown of a tooth, which is depicted, shown, or otherwise represented in both of the training images 803 and the 3D training model 906. In some embodiments, the computing device 910 may be or include one or more processors and memory of the model training system 902 configured to automatically generate the correlation points 916. In some embodiments, the computing device 910 may be a computer (e.g., a desktop, laptop, or other computer) configured to receive a selection of the correlation points 916. The computing device 910 may be configured to use the correlation points 916 for establishing a data packet 914 of a training set 912 that is used for training the machine learning model 922, as described in greater detail below. In some embodiments, the computing device 910 may be configured to update the metadata file with the correlation points 916.

The computing device 910 (or one or more other devices, components, or engines of the model training system 902) may be configured to generate, establish, populate, or otherwise provide a training set 912. The training set 912 may include a plurality of data packets 914. Each of the data packets 914 may include the training image(s) 804, and the associated 3D training model 906, and the correlation points 916 between the training images 904 and the associated 3D training model 906. As such, each data packet 914 of the plurality of data packets 914 may be representative of a respective dental arch which is used for training the machine learning model 922. The training set 912 may include data packets 914 for a plurality of different users, and for a plurality of different dental arches. As such, each data packet 914 may include data that represents a unique dental arch.

The computing device 910 may be configured to generate, establish, or otherwise provide one or more configuration parameters 918 for generating the machine learning model 922. In some embodiments, the configuration parameters 918 may be automatically set by a user (such as a technician) operating the computing device 910 to tune the training of the machine learning model 922. The user may tune the training of the machine learning model 922 based on outputs from the machine learning model 922. In some embodiments, the computing device 910 may be configured to automatically generate the configuration parameters 918. The computing device 910 may automatically generate the configuration parameters 918 based on model evaluation interfaces (such as those shown in FIG. 18). Various examples for automatically or manually generating configuration parameters 918 include accuracy of 3D models generated by the machine learning model 922 (in comparison to actual 3D models), processing time in which the machine learning model 922 generates the 3D models, etc.

The computing device 910 may be configured to provide the configuration parameters 918 to a machine learning training engine 920 for generating the machine learning model 922. In some embodiments, the configuration parameters 918 may include a number of iterations in which the machine learning training engine 920 is to perform to train the machine learning model 922 using the training set 912. In some embodiments, the configuration parameters 918 may include a loss weight for a set of hyperparameters that are used by the machine learning training engine 920. The computing device 910 may be configured to send, transmit, or otherwise provide the configuration parameters to the machine learning training engine 920 (e.g., along with the training set 912) for training the machine learning model 922.

The model training system 902 is shown to include a machine learning training engine 920. The machine learning training engine 920 may be any device(s), component(s), application(s), element(s), script(s), circuit(s), or other combination of software and/or hardware designed or implemented to generate, configure, train, or otherwise provide a machine learning model 922 for generating a 3D model from one or more user images. The machine learning training engine 920 may be configured to receive the training set 912 and the configuration parameters 918 (e.g., from the computing device 910 and/or from another device or component of the model training system 902) for generating the machine learning model 922. In some embodiments, the machine learning training engine 920 may be similar in some respects to the model generation engine 204 described above with respect to FIG. 2. In some embodiments, the machine learning training engine 920 may be similar to or incorporate features from a mesh R-CNN training system, such as the system described in "Mesh R-CNN" [Georgia Gkioxari, Jitendra Malik, & Justin Johnson, Mesh R-CNN, Facebook AI Research (FAIR) (Jan. 25, 2020)], the contents of which are incorporated by reference in its entirety. The machine learning training engine 920 may be configured to generate the machine learning model 922 for generating a 3D model from images of a dental impression of a dental arch of a user (such as a patient who is to receive or is receiving dental treatment), as described in greater detail below. Further details corresponding to the model training system 902 are described in greater detail below with respect to FIG. 10 through FIG. 13.

The system 900 is shown to include a model generation system 924. The model generation system 924 may be or include any device(s), component(s), application(s), element(s), script(s), circuit(s), or other combination of software and/or hardware designed or implemented to generate a 3D model 930 from a set of 2D images 928 received from a user device 926. The model generation system 924 may include or leverage the machine learning model 922 generated by the machine learning training engine 920 for generating the 3D model 930.

The model generation system 924 may be configured to receive one or more user images 928 from a user device 926. The user device 926 may be a mobile device (e.g., a smart phone, tablet, etc.). In some embodiments, the user device 926 may be associated with a user (such as the user depicted in the user image 928). In some embodiments, the user device 926 may be a generic device (e.g., a device used to capture images 928 of a plurality of users, such as at an intraoral scanning location, dental or medical office, etc.). The user device 926 may be a computing device (e.g., similar to the computing device 910 described above). The user device 926 may be configured to generate, capture, or otherwise provide the user images 928 to the model generation system 924. In some embodiments, the user device 926 may be configured to provide the user images 928 to the model generation system 924 by uploading the images 928 to a portal maintained by or otherwise associated with the model generation system 924. In some embodiments, the user device 926 may be configured to provide the user images 928 to the model generation system 924 by transmitting the images 928 to an address associated with the model generation system 924 (e.g., an IP address associated with a server which hosts the model generation system 924, an email address associated with an account linked to the model generation system 924, etc.). The one or more user images 928 may be representative of a dental impression of a common dental arch. The user images 928 may represent a dental impression of a common dental arch, and may be used to generate a 3D model 930 of the dental arch represented in the images of the dental impression(s).

The model generation system 924 is shown to include the machine learning model 922 (e.g., generated or otherwise trained by the machine learning training engine 920). The model generation system 924 may be configured to transmit, send, or otherwise provide the received user images 928 to the machine learning model 922 to generate the 3D model 930 of the dental arch represented in the user images 928. The model generation system 924 may be configured to execute an instance of the machine learning model 922 by providing the user images 928 as an input to the machine learning model 922. The machine learning model 922 may be configured to generate, as an output, a 3D model 930 of the dental arch based on the user images 928. In some embodiments, the machine learning model 922 may be configured to generate a plurality of 3D models of each perspective of the dental arch included in a respective image 928. The machine learning model 922 may be configured to stitch together the plurality of 3D models of each perspective dental arch to establish, generate, or otherwise form the 3D model 930 as an output.

The 3D model 930 may be used to generate, construct, or otherwise manufacture one or more dental aligners as described above with reference to FIG. 2-FIG. 6C. For example, in some embodiments, a manufacturing system manufactures the dental aligner(s) based at least in part on the 3D model 930 of the dental arch of the user. The manufacturing system may manufacture the dental aligner(s) by receiving the data corresponding to the 3D model 930 generated by the model generation system 924. The manufacturing system may manufacture the dental aligner(s) by 3D printing a physical model based on the 3D model 930, thermoforming a material to the physical model, and cutting the material to form a dental aligner from the physical model. The manufacturing system may manufacture the dental aligner(s) by 3D printing a dental aligner using the 3D model 930. In these or other embodiments, the dental aligner(s) are specific to the user and are configured to reposition one or more teeth of the user.

In some embodiments, the 3D model 930 may be used to track a progress of dental aligner treatment for a patient. For example, a patient may be treated using dental aligners to move the patient's teeth in various stages from an initial position (e.g., prior to treatment) to a final position (e.g., following treatment). During treatment, the patient's teeth may move from the initial position (e.g., at a first stage of a treatment plan) to one or more intermediate positions (e.g., at one or more intermediate stages of the treatment plan), and to the final position (e.g., at a final stage of the treatment plan). Each of the stages of treatment may be represented in a patient file as a target 3D model (e.g., a first 3D model representing the first stage of treatment, one or more intermediate 3D models representing the intermediate stages of treatment, and a final 3D model representing the final stage of treatment). At each stage, the patient may administer one of a series of dental aligners that are configured to move the patient's teeth from the current stage of treatment to the subsequent stage of treatment.

In some implementations, the patient may upload the user images 928 of impressions made following completion of one stage of treatment. For example, the patient may be prompted to upload images 928 at various intervals (such as daily, weekly, every two weeks, following completion of a stage of treatment, every six months or year following treatment via dental aligners, whenever the patient requests to check their progress, etc.). The patient may be prompted to upload images 928 to ensure that the patient's teeth are progressing according to the treatment plan, or to ensure that the patient's teeth have not reverted back to a position prior to treatment via dental aligners. The model generation system 924 may be configured to generate the 3D model 930 based on the user images 928. The 3D model 930 may then be compared to the 3D model included in the patient file to determine whether the patient's teeth moved according to the treatment plan for the patient. The patient file may include a 3D model for each stage of treatment (e.g., an initial 3D model corresponding to an initial stage of treatment, one or more intermediate 3D models corresponding to intermediate stages of treatment, and a final 3D model corresponding to the final stage of treatment). The 3D model 930 generated by the model generation system 924 may be compared to the 3D models from the patient file. For example, where the 3D model 930 generated from the user images 928 matches (or substantially matches) the 3D model included in the patient file corresponding to the particular stage of the treatment plan, the patient may be determined to be progressing in accordance with the treatment plan, since the patient's teeth are moving according to the progression defined in the treatment plan from their initial position prior to treatment, to one or more intermediate positions, and to a final position following treatment. However, where the 3D model 930 generated from the user images 928 does not match (or substantially match) the 3D model included in the patient file corresponding to the particular stage of the treatment plan, the patient may be determined to not be progressing in accordance with the treatment plan. Such embodiments may provide for early onset identification of a need for a mid-course correction of a treatment plan. For example, when a patient is determined to not be progressing according to the treatment plan, the patient file may be flagged to generate a new treatment plan from the patient's current teeth positions (and, correspondingly, new dental aligners according to the new treatment plan). As another example, when the patient is determined to not be progressing according to the treatment plan, the patient may be prompted to skip one or more aligners (e.g., to advance to another stage of treatment where the patient is progressing faster than expected or predicted under the treatment plan), use a particular aligner out of order, such that the patient's teeth move back on course according to the treatment plan.

In some embodiments, the 3D model 930 may be rendered on a user interface and displayed back to a user. For example, the model generation system 924 may be configured to transmit, send, or otherwise provide the 3D model 930 to the user device 926 for rendering to the user. In some embodiments, the model generation system 924 may be configured to generate a user interface for displaying at the user device 926. The user interface may include, for example, the 3D model 930 generated based on the user images 928. In some embodiments, the user interface may include another 3D model. For example, the user interface may include the 3D model 930 generated based on the user images 928 and an expected 3D model (such as the 3D model from the patient file corresponding to the current stage of treatment). Such embodiment may allow the user to track their progress in comparison to the target 3D model corresponding to the treatment. As another example, the user interface may include the 3D model 930 and a prior (and/or subsequent) 3D model. The prior 3D model may be the 3D model from the patient file corresponding to a prior stage of the treatment plan. The prior 3D model may be a 3D model generated from a previous user image 928. The subsequent 3D model may be the 3D model from the patient file corresponding to a subsequent stage of the treatment plan. The user may view the prior 3D model, the current 3D model 930, and/or a subsequent 3D model to show a progress of the patient's treatment.

Figure 10:
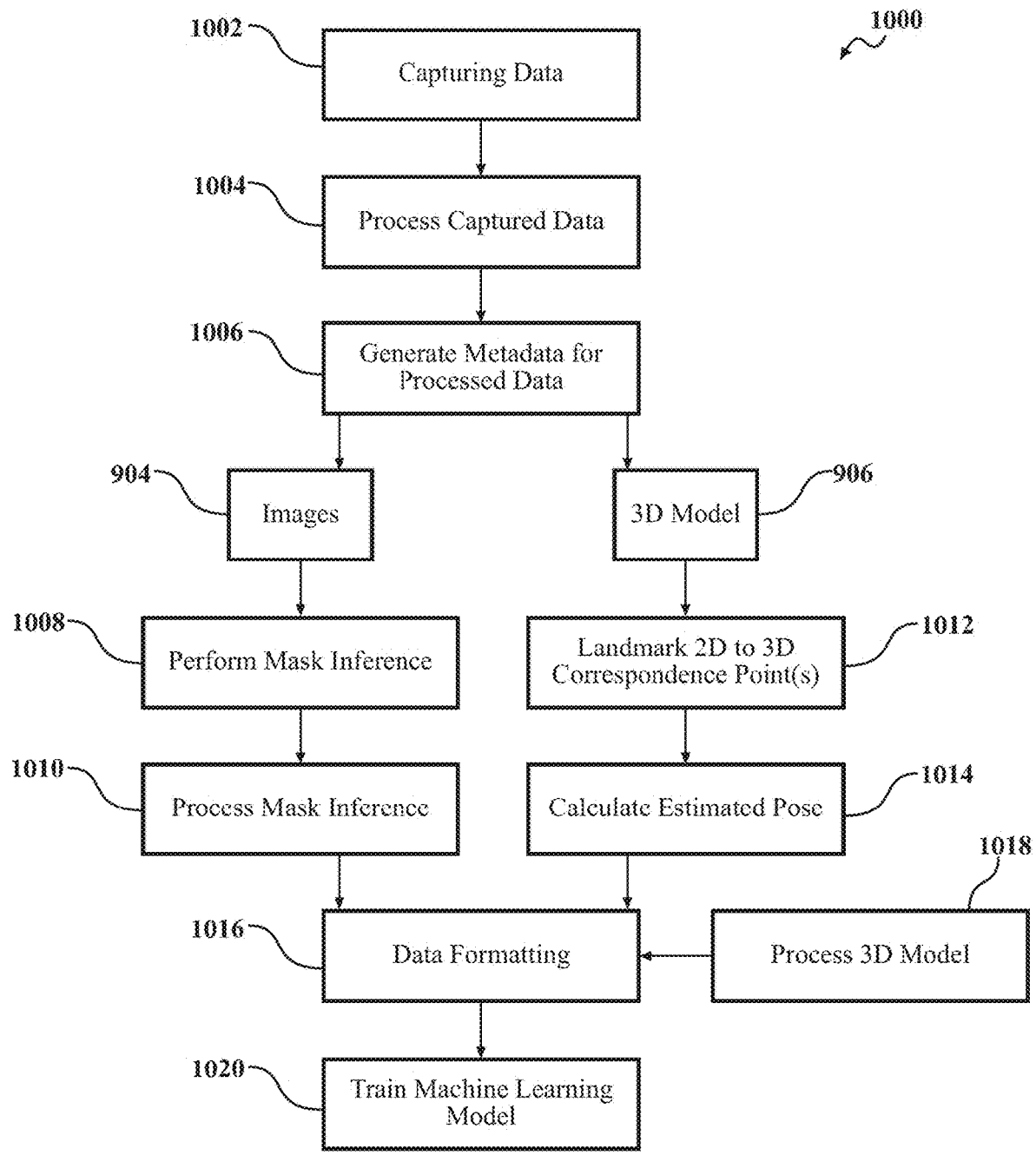
FIG. 10 a diagram of a method of training a machine learning model, according to an illustrative embodiment.
Figure 11A:
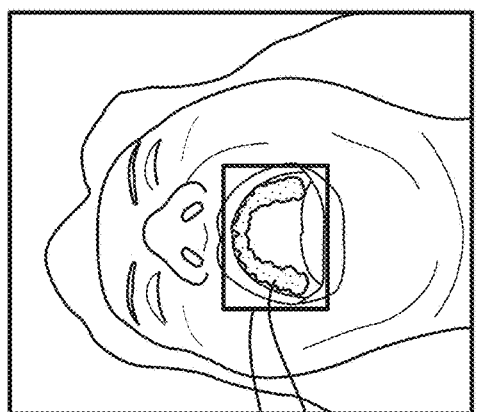
FIG. 11A is an illustration of a first example training image, according to an illustrative embodiment
Figure 11B:
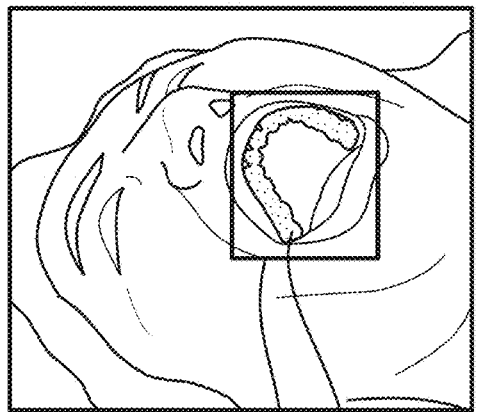
FIG. 11B is an illustration of a second example training image, according to an illustrative embodiment.
Figure 11C:
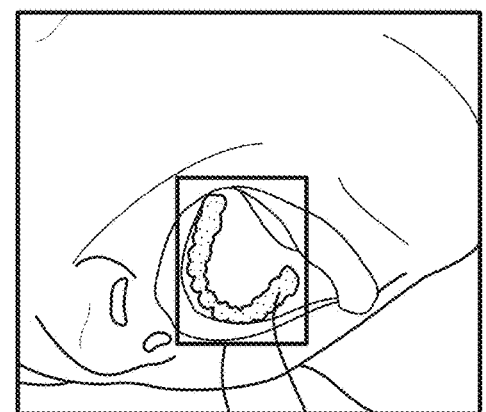
FIG. 11C is an illustration of a third example training image, according to an illustrative embodiment.
Figure 11D:
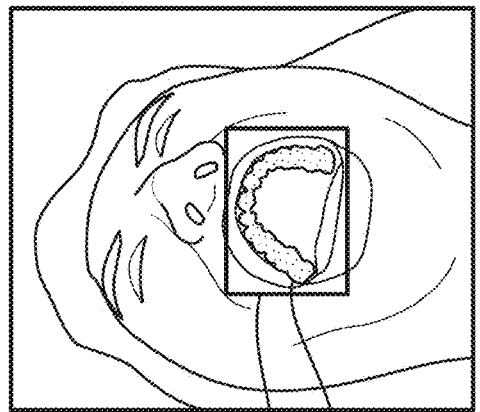
FIG. 11D is an illustration of a fourth example training image, according to an illustrative embodiment.

Referring now to FIG. 10, a flow chart showing an example method 1000 of training a machine learning model 922 is shown. The method 1000 may be performed by one or more of the components described above with reference to FIG. 9, such as the model training system 902. In some embodiments, the method 1000 may be performed to train a machine learning model 922 to generate 3D models of a dental arch from 2D images of a dental impression of the dental arch. In other embodiments, and as described in greater detail below, the method 1000 may be performed to train a machine learning model 922 to generate 3D models of a dental arch from 2D images of the dental arch. However, it is noted that, in either embodiment, the machine learning model 922 may be trained in substantially the same manner.

As a brief overview, at step 1002, the model training system 902 captures data (such as training images 904 and a 3D training model 906). At step 1004, the model training system 902 processes the captured data. At step 1006, the model training system 902 generates metadata for the processed data. At step 1008, the model training system 902 performs a mask inference, and at step 1010, the model training system 902 processes the mask inference. At step 1012, the model training system 902 landmarks 2D to 3D correlation points 916. At step 1014, the model training system 902 calculates an estimated pose. At step 1016, the model training system 902 performs data formatting. At step 1018, the model training system 902 processes the 3D model 906. At step 1020, the model training system 902 trains the machine learning model 922. These steps are described in greater detail below with reference to FIG. 9 and FIG. 10 in conjunction with FIG. 10-FIG. 13.

At step 1002, the model training system 902 receives data (such as training images 904 and a 3D training model 906). In some embodiments, the model training system 902 may receive or retrieve the data from a data structure or source that stores a plurality of images and corresponding 3D models. As described above, each of the 3D training models 906 may be representative of a unique dental arch. The model training system 902 may capture, retrieve, or otherwise receive a plurality of 3D training models 906 and a set of training images 904 that include at least a portion of a representation of the dental arch associated with a respective 3D training model 906. In other words, the model training system 902 may receive, for a particular dental arch that is to be used in the training set 912, a 3D training model 906 of the dental arch and one or more training images 904 which include a representation of at least a portion of the dental arch.

At step 1004, the model training system 902 processes the received data. In some embodiments, the data ingestion engine 908 of the model training system 902 may process the received data (e.g., received at step 1002). The data ingestion engine 908 may process the captured data by selecting a subset of the training images 904 which are to be used for training the machine learning model 922. For example, the training images 904 received at step 1002 may include a video including a series of frames, each of which show a perspective view of a mouth of a patient. The data ingestion engine 908 may select a subset of frames from the series of frames of the video. In some embodiments, the data ingestion engine 908 may select a subset of frames based on a quality of the subset of frames. In some embodiments, the data ingestion engine 908 may select a subset of frames based on a particular perspective view of the dental arch of the user depicted in a respective frame. In some embodiments, the data ingestion engine 908 may process the 3D model as described in greater detail below with reference to step 1018. In other words, step 1018 may be performed when the 3D training model 906 is ingested or otherwise captured at step 1002, or step 1018 may be performed subsequent to one or more of the following steps described in greater detail below.

At step 1006, the model training system 902 generates metadata for the processed data. In some embodiments, the data ingestion engine 908 may generate the metadata for the processed data. In some embodiments, the data ingestion engine 908 may generate a metadata file including the metadata for the training images 904 and the associated 3D training model 906. The metadata file may be or include data that correlates or links a set of the training images 904 of a user with the 3D training model 906 of the dentition of the user represented in the set of training images 904. In some embodiments, the metadata file may include data corresponding to the training images 904. For example, the metadata file may include data corresponding to an image contrast of the training images 904, a focus of the training images 904, a pixel size of the training images 904, a focal length of a camera used to capture the training images 904, a normalization factor of the training images 904, a scaling of the training images 904, etc. Such data may be used to standardize the training images 904 across the training set 912.

Referring now to FIG. 10 and FIG. 11A-FIG. 11D, at step 1008, the model training system 902 performs a mask inference. Specifically, FIG. 11A-FIG. 11D show respective training images 1100*a-d*. As shown in FIG. 11A-FIG. 11D, each of the images 1100*a-d* may include a bounding box 1102*a-d* surrounding a dental arch of the person depicted in the respective image 1100*a-d*, and a mask 1104*a-d* applied to the dental arch. The model training system 902 may apply the mask 1104*a-d* by performing object recognition of teeth within the image 1100*a-d*, and generating an overlay over the teeth within the image 1100*a-d*. As such, the mask 1104*a-d* may be or include an overlay which is applied to particular objects or features within an image 1100*a-d* (such as the teeth as shown in FIG. 11A-FIG. 11D). The model training system 902 may apply the bounding box 1102*a-d* to encompass each of the teeth recognized in the image 1100*a-d* (e.g., to encompass the mask 1104*a-d* within the image 1100*a-d*). In some embodiments, the model training system 902 may include or access one or more masking systems that are configured to automatically generate a mask 1104*a-d* and bounding box 1102*a-d* for an image 1100*a-d*. In some embodiments, the model training system 902 may include or otherwise access masking software hosted on a server which is remote from the system 900 via an application program interface (API) for the masking software. For instance, the model training system 902 may access Detectron2 developed by FAIR for masking the images 1100 of the training set. The mask 1104 may define a perimeter or edge of the teeth shown or represented in the dental arch. In some embodiments, the mask 1104*a-d* may be applied to individual teeth (e.g., on a tooth-by-tooth basis). In some embodiments, the mask 1104*a-d* may be applied to a subset of teeth (e.g., based on a tooth type, such as incisors, molar, premolar, etc.). In some embodiments, the mask 1104*a-d* may be applied to each of the teeth located in a common dental arch (e.g., maxillary teeth and mandibular teeth). While FIGS. 11A-11D depict training images 1100*a-d* of a dental arch of a user, it will be appreciated that a similar methodology can be applied to training images of dental impressions taken of a dental arch of a user.

At step 1010, the model training system 902 processes the mask inference. In some embodiments, the model training system 902 processes the mask inference (e.g., the mask 1104*a-d*) applied to the training images 1100 *a-d*) to determine that the masks 1104 *a-d* are properly applied to the dental arch represented in the training image 1100 *a-d*. The model training system 902 may display, render, or otherwise provide the images 1100 *a-d* including the mask 1104 *a-d* to the computing device 910 for performing a quality control of the mask 1104 *a-d*. In some implementations, the model training system 902 may receive one or more adjustments of the mask 1104 *a-d* (e.g., from the computing device 910). The adjustments may be made by dragging a portion of an edge of the mask 1104 *a-d* to align with a corresponding portion of the dental arch in the image 1100 *a-d*, adjusting the bounding box 1102*a-d*, etc.

Figure 12:
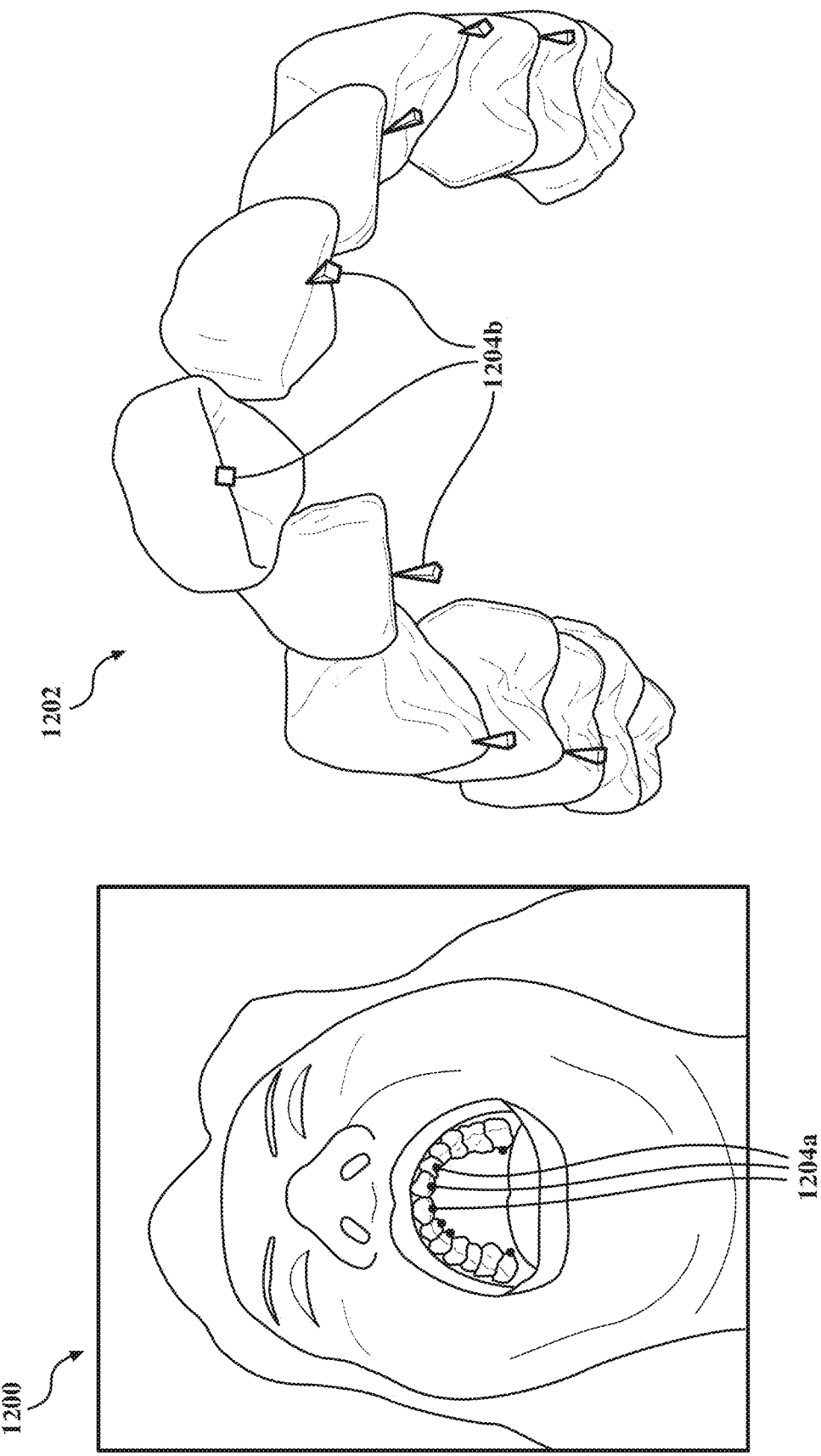
FIG. 12 are illustrations of a training image and a corresponding 3D training model, according to an illustrative embodiment.

Referring now to FIG. 10 and FIG. 12, at step 1012, the model training system 902 landmarks 2D to 3D correlation points 916. Specifically, FIG. 12 shows a training image 1200 and a corresponding 3D training model 1202. The training image 1200 and corresponding 3D training model 1202 may be one of the data packets 914 of the training set 912 received at step 1002. As shown in FIG. 12, the training image 1200 and 3D training model 1202 may include correlation points 1204*a-b*. Specifically, the training image 1200 includes correlation points 1204*a*, and the 3D training model 1202 includes correlation points 1204*b*. Each of the correlation points 1204*a-b* may be representative of or otherwise identify a common point represented in both the training image 1200 and 3D training model 1202. As shown in FIG. 12, a given correlation point 1204 may map to a respective tooth that is shown in both of the training image 1200 and the 3D training model 1202. In some embodiments, the computing device 910 may automatically generate the correlation points 1204*a-b* in the training image 1200 and the 3D training model 1202. For example, the computing device 910 may analyze the images 1200 and the 3D training model 1202 to identify each of the individual teeth located in the images 1200 and 3D training model 1202. The computing device 910 may be configured to apply one or more labels to each of the individual teeth in both the images 1200 and 3D training model 1202. The computing device 910 may be configured to automatically generate the correlation points 1204*a-b* at a mid-point of each of the teeth represented in both of the training images 1200 and the 3D training model 1202. In some embodiments, the computing device 910 may receive a selection (e.g., from a user of the computing device 910) of the correlation points 1204 in the training image 1200 and the 3D training model 1202.

Figure 13:
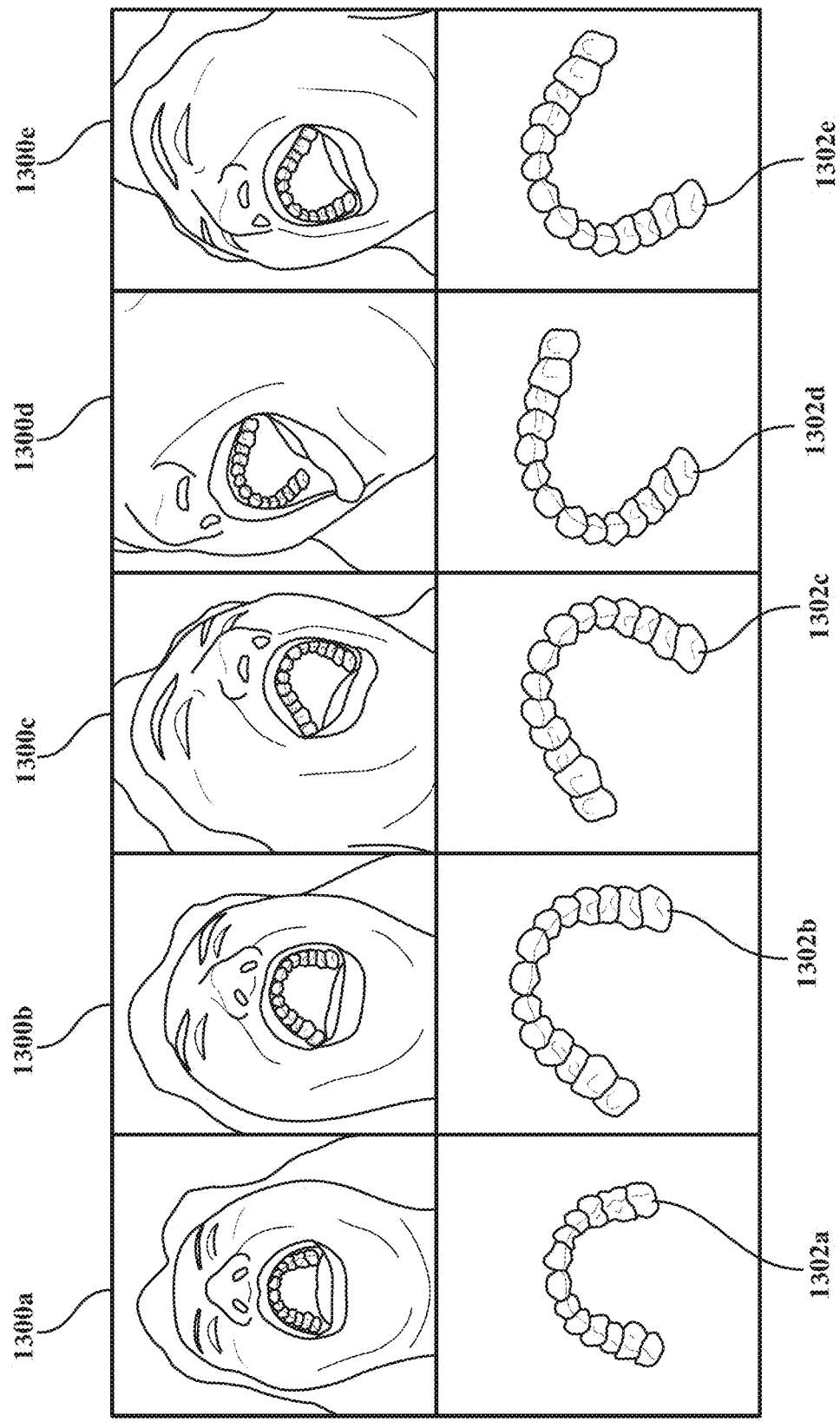
FIG. 13 are illustrations of a series of training images and corresponding poses of the 3D training model for the training images, according to an illustrative embodiment.

Referring now to FIG. 10 and FIG. 13, at step 1014, the model training system 902 calculates an estimated pose. Specifically, FIG. 13 shows a series of training images 1300 and corresponding poses of the 3D training model 1302 for the training images 1300. In some embodiments, the model training system 902 calculates the estimated pose of the user in the training image 1300 by performing a camera constant, rotation, and translation (KRT) analysis (or other pose alignment analysis) of the images. In some embodiments, the model training system 902 calculates the estimated pose of the user in the training image 1300 using metadata corresponding to the camera used to capture the image 1300 (e.g., one or more intrinsic properties of the camera that captured the images 1300, such as focal length, principal axis, etc.), a rotation of the dental arch reflected in the image, and a translation of the dental arch reflected in the image. The model training system 902 may calculate the estimated pose of a respective training image 1300, to match the pose of the 3D training model with the estimated pose of the user in the training image 1300. For example, the model training system 902 may translate, rotate, or otherwise modify the pose of the 3D training model to match the calculated pose for the training image 1300.

In some embodiments, steps 1008 through 1014 may be executed in parallel. For example, steps 1008 through 1010 may be performed on the images while steps 1012 through 1014 may be performed on the 3D model. In some embodiments, steps 1008 through 1014 may be executed serially (e.g., the model training system 902 may landmark the 2D to 3D correlation points 916 following processing the mask inference).

At step 1016, the model training system 902 performs data formatting. In some embodiments, the model training system 902 may format the training images 904, 3D training models 906, and correlation points 916 (generally referred to as a training set 912) into a format acceptable for training a machine learning model. For example, the model training system 902 may format the training set 912 into a common objects in context (COCO) data format. The model training system 902 may format the training set 912 prior to providing the training set 912 to the machine learning training engine 920 for training the machine learning model 922.

Figure 14:
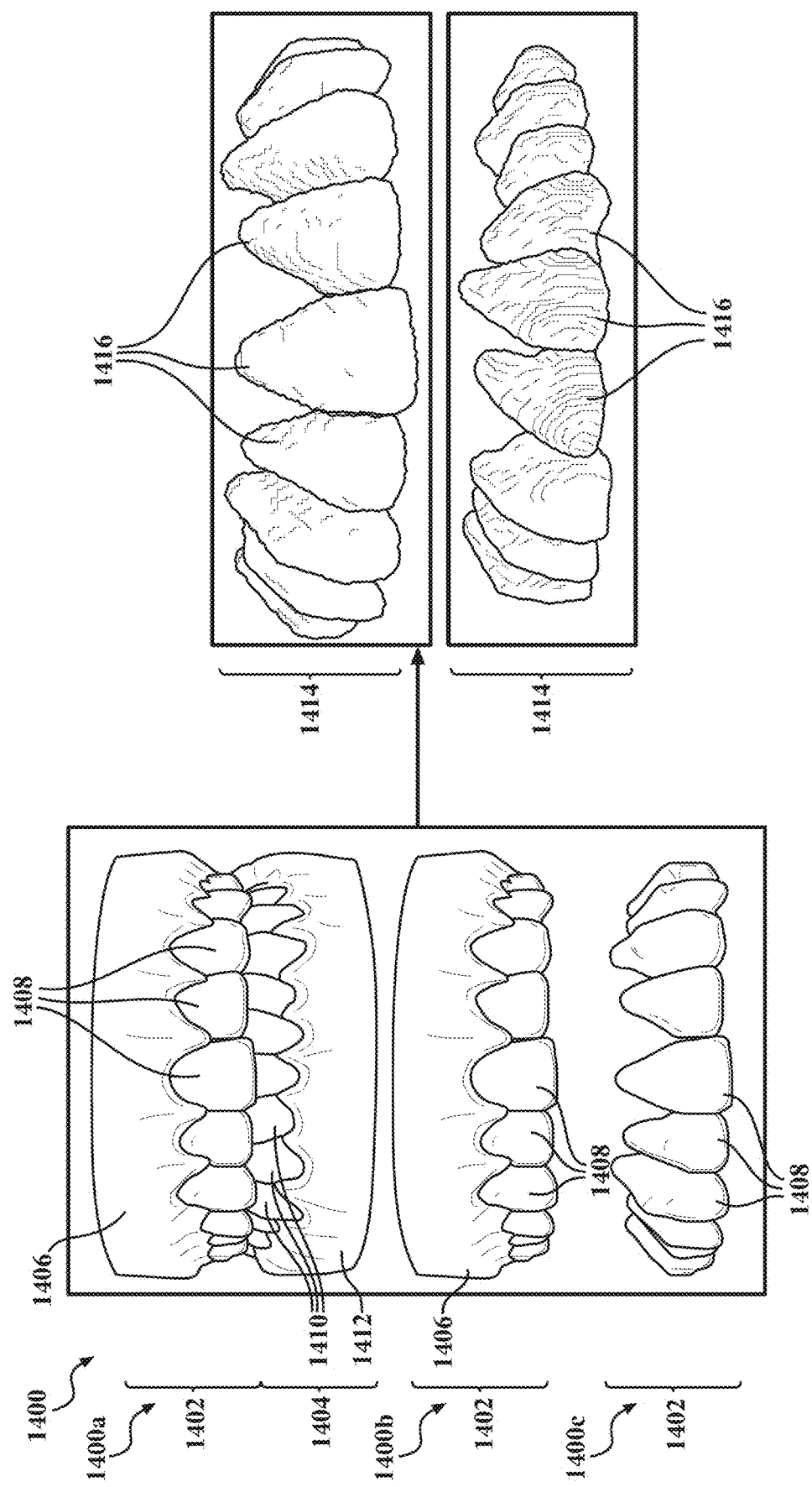
FIG. 14 is an illustration of a processing progression of a 3D model which is used in a training set, according to an illustrative embodiment.

Referring now to FIG. 10 and FIG. 14, at step 1018, the model training system 902 processes the 3D model 1400. Specifically, FIG. 14 shows a processing progression of a 3D model 906 that is used in the training set 912, according to an illustrative embodiment. As shown in FIG. 14, the model training system 902 may receive an initial 3D training model 1400a that includes a 3D representation 1402 of an upper dental arch of a user and a 3D representation 1404 of a lower dental arch of the user. Each of the 3D representations 1402, 1404 may include a representation of gingiva 1406, 1412 and teeth 1408, 1410 for the corresponding dental arch. The model training system 902 may process the 3D model 1400a by separating the 3D model 1400 into two 3D models (e.g., a first 3D model of the 3D representation 1402 of the upper dental arch and a second 3D model of the 3D representation 1404 of the lower dental arch), which may be a first iteration of a processed 3D model 1400b from the initial 3D model 1400a. The model training system 902 may process each of the first iteration of 3D models 1400b as shown in FIG. 14 to remove the 3D representation of gingiva 1406 from the 3D representation of teeth 1408. As such, the model training system 902 may process the first iteration of the 3D models 1400b to form a second iteration of the 3D model 1400c that includes the 3D representation of teeth 1408 without any 3D representations of gingiva 1406. The model training system 902 may generate a final iteration 1414 of the processed 3D model 1400 by voxelizing the 3D representations of the teeth 1408 in the 3D model 1400c. As such, the final iteration 1414 of the processed 3D model 1400 includes voxelized 3D representations of teeth 1416 that correspond to the 3D representations of teeth 1408 in the initial 3D model 1400. The model training system 902 may use the final iteration 1414 of the 3D model 1400 as the 3D training model 906 for training the machine learning model 922.

In some embodiments, the model training system 902 may add, generate, or otherwise incorporate gingiva into the final iteration 1414 of the 3D model 1400. For example, the model training system 902 may be configured to generate gingiva based on one or more parameters, traits, shapes, or other characteristics of the voxelized 3D representations of teeth 1416 in the final iteration of the model 1414. In some embodiments, the model training system 902 may be configured to provide the final iteration 1414 of the 3D model 1400 to a machine learning model which is trained to add or incorporate voxelized gingiva into voxelized 3D representations of teeth 1416 in a model 1400.

At step 1020, the model training system 902 trains the machine learning model 922. The model training system 902 may transmit, send, or otherwise provide the training set 912 to machine learning training engine 920 to train the machine learning model 922. In some embodiments, the model training system may provide the training set and one or more configuration parameters to the machine learning training engine 920 for training the machine learning model 922. In some embodiments, the configuration parameters 918 may include a number of iterations in which the machine learning training engine 920 trains the machine learning model 922 using the training set 912. In some embodiments, the configuration parameters 918 may include a loss weight for a set of hyperparameters that are used by the machine learning training engine 920. The computing device 910 may be configured to send, transmit, or otherwise provide the configuration parameters to the machine learning training engine 920 (e.g., along with the training set 912) for training the machine learning model 922. The machine learning training engine 920 may receive and use the training set 912 and the configuration parameters 918 (e.g., from the computing device 910 and/or from another device or component of the model training system 902) as an input for training the machine learning model 922. The machine learning training engine 920 may train one or more weights for a neural network (such as the neural network shown in FIG. 5 and described above) based on data from the training images 904, the 3D training model 906, and the correlation points 916.

In some embodiments, the 3D training models 906 and/or training images 904 may include or be represented in color. In such embodiments, the machine learning training engine 920 may be configured to train the machine learning model 922 to detect, determine, or otherwise predict a color of the 3D model based on data from one or more images. The machine learning training engine 920 may be configured to train one or more weights of a neural network to detect, determine, or otherwise predict a color of the 3D model based on one or more images which are provided (e.g., as an input) to the machine learning model 922.

Figure 15:
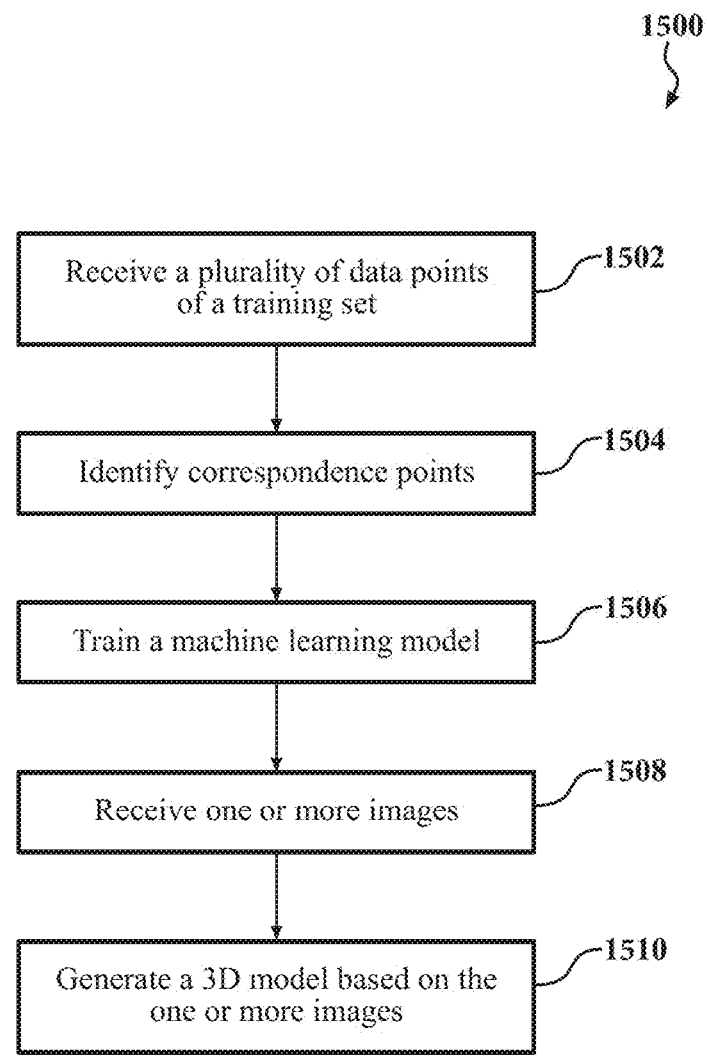
FIG. 15 is an illustration of a method of generating a 3D model from one or more 2D user images, according to an illustrative embodiment.

Referring now to FIG. 15, a flow chart showing an example method 1500 of generating a 3D model from one or more 2D user images is shown, according to an illustrative embodiment. The method 1500 may be performed by one or more of the components described above with reference to FIG. 9. As a brief overview, at step 1502, a model training system 902 receives a plurality of data packets 914 of a training set 912. At step 1504, the model training system 902 identifies correlation points 916. At step 1506, the model training system 902 trains a machine learning model 922. At step 1508, a model generation system 924 receives one or more images 928. At step 1510, the model generation system 924 generates a 3D model 930 based on the one or more images 928.

At step 1502, a model training system 902 receives a plurality of data packets 914 of a training set 912. In some embodiments, each data packet 914 includes data corresponding to one or more training images 904 of a first dental impression of a first dental arch of a first user and a three-dimensional (3D) training model 906 of the first dental arch of the first user. As such, the data packets 914 may correspond to a respective dental arch, and may include data corresponding to training images 904 of an impression of the dental arch and a 3D training model 906 of the dental arch. In some embodiments, the data ingestion engine 908 may receive the training images 904 and 3D training model 906 from a data source as described above with respect to FIG. 10. The data ingestion engine 908 may generate the data packets 914 of the training set 912 from the training images 904 and the 3D training model 906 for training the machine learning model 922, as described in greater detail below.

In some embodiments, the model training system 902 may apply a mask to one or more teeth represented in the training images 904. In some instances, the model training system 902 may apply a bounding box around a dental impression represented in the training images 904, and apply a mask to one or more of the teeth of the dental impression. In some implementations, the model training system 902 may apply the mask to individual teeth of the dental impression. In some implementations, the model training system 902 may apply the mask to the set of the teeth of the dental impression (similar to what is shown in FIG. 12 and described in greater detail above). Hence, the masks may be applied on a tooth-by-tooth basis, or the masks may be applied to each of the teeth of the dental impression shown in the training images 904.

In some embodiments, the model training system 902 may calculate an estimated perspective angle of the dental impression in the training images 904. The model training system 902 may calculate the estimated perspective angle by performing a KRT analysis (e.g., using metadata corresponding to the training images 904) as described above with respect to FIG. 10 and FIG. 13. The model training system 902 may use the estimated perspective angle for modifying a pose of the 3D training model 906. For example, the model training system 902 may adjust, modify, or otherwise change the pose of the 3D training model 906 to match (or substantially match) the estimated perspective angle of the dental impression shown in the training images 904. The model training system 902 may modify the pose of the 3D training model 906 to match the estimated perspective angle in the training images 904 for displaying on a computing device used for selecting correlation points 916, as described in greater detail below.

In some embodiments, the model training system 902 may generate the 3D training model 906 from an initial 3D training model (as described above). For example, the model training system 902 may receive an initial 3D training model that includes a 3D representation of an upper dental arch of a user and a 3D representation of a lower dental arch of the user. Each of the 3D representations may include representations of teeth and gingiva (e.g., a 3D representation of upper teeth and a 3D representation of upper gingiva, and a 3D representation of lower teeth and a 3D representation of lower gingiva). The model training system 902 may generate the 3D training model from the initial 3D training model by separating the 3D representation of the upper dental arch from the 3D representation of the lower dental arch, and removing the 3D representation of the gingiva from the separated 3D representation of teeth. As such, the 3D training model may include the 3D representation of the plurality of teeth for the dental arch. In some implementations, the model training system 902 may voxelize the 3D training model (e.g., voxelize at least the teeth represented in the 3D training model).

At step 1504, the model training system 902 identifies correlation points 916. In some embodiments, the model training system 902 may identify a plurality of correlation points 916 between the one or more training images 904 and the 3D training model 906 of a respective dental arch for a data packet 914 of the training set 912. In some embodiments, the model training system 902 may identify the correlation points 916 by receiving a selection of the correlation points 916 from a computing device 910. The computing device 910 may display the training images 904 and the 3D training model 906. A user of the computing device 910 may select a first point on the training image 904. The user may then select a second point on the 3D training model 906 that corresponds to the first point on the training image 904. As such, the first and second points may together form a correlation point. In some embodiments, the model training system 902 may automatically select the correlation points between the training images 904 and the 3D training model 906.

At step 1506, the model training system 902 trains a machine learning model 922. In some embodiments, the model training system 902 may train the machine learning model 922 using the plurality of correlation points 916 for the plurality of data packets 914 of the training set 912. In some embodiments, the model training system 902 may train the machine learning model 922 by transmitting, sending, or otherwise providing the correlation points 916, training images 904, and 3D training model 906 (which collectively form the training set 912) to a machine learning training engine 920 which trains the machine learning model 922. The machine learning training engine 920 may use the training set 912 as an input for training one or more weights of a neural network corresponding to the machine learning model 922. In some embodiments, the machine learning training engine 920 may train the machine learning model 922 to detect, determine, or otherwise predict a color of the 3D model. In such embodiments, the training set 912 may include color data (e.g., the training images 904 and/or the 3D training model 906 may include color data).

In some embodiments, the model training system 902 may receive one or more configuration parameters for generating the machine learning model 922. The model training system 902 may receive the configuration parameters from a computing device (such as computing device 910). The configuration parameters may include, for example, a number of training iterations that the machine learning training engine 920 is to perform using the training set 912 for training the machine learning model 922. The model training system 902 may transmit the configuration parameters along with the training set 912 to the machine learning training engine 920, to cause the machine learning training engine 920 to perform the number of iterations on the training set to generate the trained machine learning model 922.

At step 1508, a model generation system 924 receives one or more images 928. In some embodiments, the model generation system 924 receives one or more images 928 of a dental impression of a patient. The model generation system 924 may receive the images 928 from a user device 926. The user device 926 may transmit, send, or otherwise provide the images 928 to the model generation system 924 (e.g., by uploading the images 928 to a portal associated with the model generation system 924, by transmitting the images 928 to an address associated with the model generation system 924, etc.). The images 928 may represent a portion of a dental impression of a dental arch of the patient. In some embodiments, the model generation system 924 may receive a plurality of images 928 of the dental impression. The plurality of images 928 may each depict or otherwise represent a portion of the dental impression from a different perspective such that the plurality of images 928 together represent the dental impression (e.g., in its entirety).

At step 1510, the model generation system 924 generates a 3D model 930 based on the one or more images 928. In some embodiments, the model generation system 924 may generate the 3D model of the dental arch of the patient by applying the one or more images of the dental impression to the machine learning model (e.g., generated at step 1506). The model generation system 924 may provide the one or more images received at step 1508 to the machine learning model as an input. The machine learning model may be trained to generate the 3D model 930 based on the images received as an input and corresponding weights of the neural network for the machine learning model. As such, the machine learning model may generate the 3D model 930 as an output based on the input images 928 and the corresponding weights of the neural network of the machine learning model. In some embodiments, such as where the machine learning model is trained to predict a color of the 3D model 930, the machine learning model may generate the 3D model 930 to include color data based on the input images 928. The 3D model 930 may be generated as a Standard Triangle Language (STL) file for stereolithography, a mesh, or other 3D representation of the dental arch of the patient represented in the image(s). The STL file can describe only a triangulated surface geometry of the 3D model 930 without any representation of color, texture or other attribute.

In some embodiments, the method 1500 may further include manufacturing a dental aligner based on the 3D model where the dental aligner is specific to the user and configured to reposition one or more teeth of the user. Manufacturing the dental aligner may be similar to step 708 of FIG. 7 described above.

In some embodiments, the method 1500 may further include tracking a progress of repositioning one or more teeth of a patient via one or more dental aligners from an initial position prior to treatment to a final position following treatment. As described above, a patient may be treated according to treatment plan including a series of stages of movement (and corresponding dental aligners used at a respective stage to implement movement of the teeth in accordance with the treatment plan). The model generation system 924 may generate the 3D model 930 based on images 928 captured following administering impressions subsequent to one or more stages of treatment (or following treatment via dental aligners). The user may capture images 928 responsive to one or more prompts to capture images at various intervals of treatment. For example, the patient may be prompted to upload images 928 at various intervals (such as daily, weekly, every two weeks, following completion of a stage of treatment, every six months or year following treatment via dental aligners, whenever the patient requests to check their progress, etc.). The 3D model 930 generated by the model generation system 924 may then be compared to the 3D model included in a patient file corresponding to the stage of treatment to determine whether the patient's teeth moved according to the treatment plan (e.g., as expected) for the patient. The patient file may include a 3D model for each stage of treatment (e.g., an initial 3D model corresponding to an initial stage of treatment, one or more intermediate 3D models corresponding to intermediate stages of treatment, and a final 3D model corresponding to the final stage of treatment). The 3D model 930 generated by the model generation system 924 may be compared to the 3D models from the patient file. For example, where the 3D model 930 generated from the user images 928 matches (or substantially matches) the 3D model included in the patient file corresponding to the particular stage of the treatment plan, the patient may be determined to be progressing in accordance with the treatment plan, since the patient's teeth are moving according to the progression defined in the treatment plan from their initial position prior to treatment, to one or more intermediate positions, and to a final position following treatment. However, where the 3D model 930 generated from the user images 928 does not match (or substantially match) the 3D model included in the patient file corresponding to the particular stage of the treatment plan, the patient may be determined to not be progressing in accordance with the treatment plan. When the patient is determined to not be progressing in accordance with a treatment plan, the patient file may be flagged for a mid-course correction of treatment. For example, when a patient is determined to not be progressing according to the treatment plan, the patient file may be flagged to generate a new treatment plan from the patient's current teeth positions (and, correspondingly, new dental aligners according to the new treatment plan). As another example, when the patient is determined to not be progressing according to the treatment plan, the patient may be prompted to skip one or more aligners (e.g., to advance to another stage of treatment where the patient is progressing faster than expected or predicted under the treatment plan), use a particular aligner out of order, such that the patient's teeth move back on course according to the treatment plan.

In some embodiments, the method 1500 may further include displaying the 3D model 930 on a user interface at the user device 926. In other words, the 3D model 930 may be rendered on a user interface back to a user via the user device 926. For example, the model generation system 924 may transmit, send, or otherwise provide the 3D model 930 to the user device 926 for rendering to the user. In some embodiments, the model generation system 924 may generate a user interface for displaying at the user device 926. The user interface may include, for example, the 3D model 930 generated based on the user images 928. In some embodiments, the user interface may include another 3D model. For example, the user interface may include the 3D model 930 generated based on the user images 928 and an expected 3D model (such as the 3D model from the patient file corresponding to the current stage of treatment). Such embodiment may allow the user to track their progress in comparison to the target 3D model corresponding to the treatment plan. As another example, the user interface may include the 3D model 930 and a prior (and/or subsequent) 3D model. The prior 3D model may be the 3D model from the patient file corresponding to a prior stage of the treatment plan. The prior 3D model may be a 3D model generated from a previous user image 928. The subsequent 3D model may be the 3D model from the patient file corresponding to a subsequent stage of the treatment plan. The user may view the prior 3D model, the current 3D model 930, and/or a subsequent 3D model to show a progress of the patient's treatment.

Figure 16:
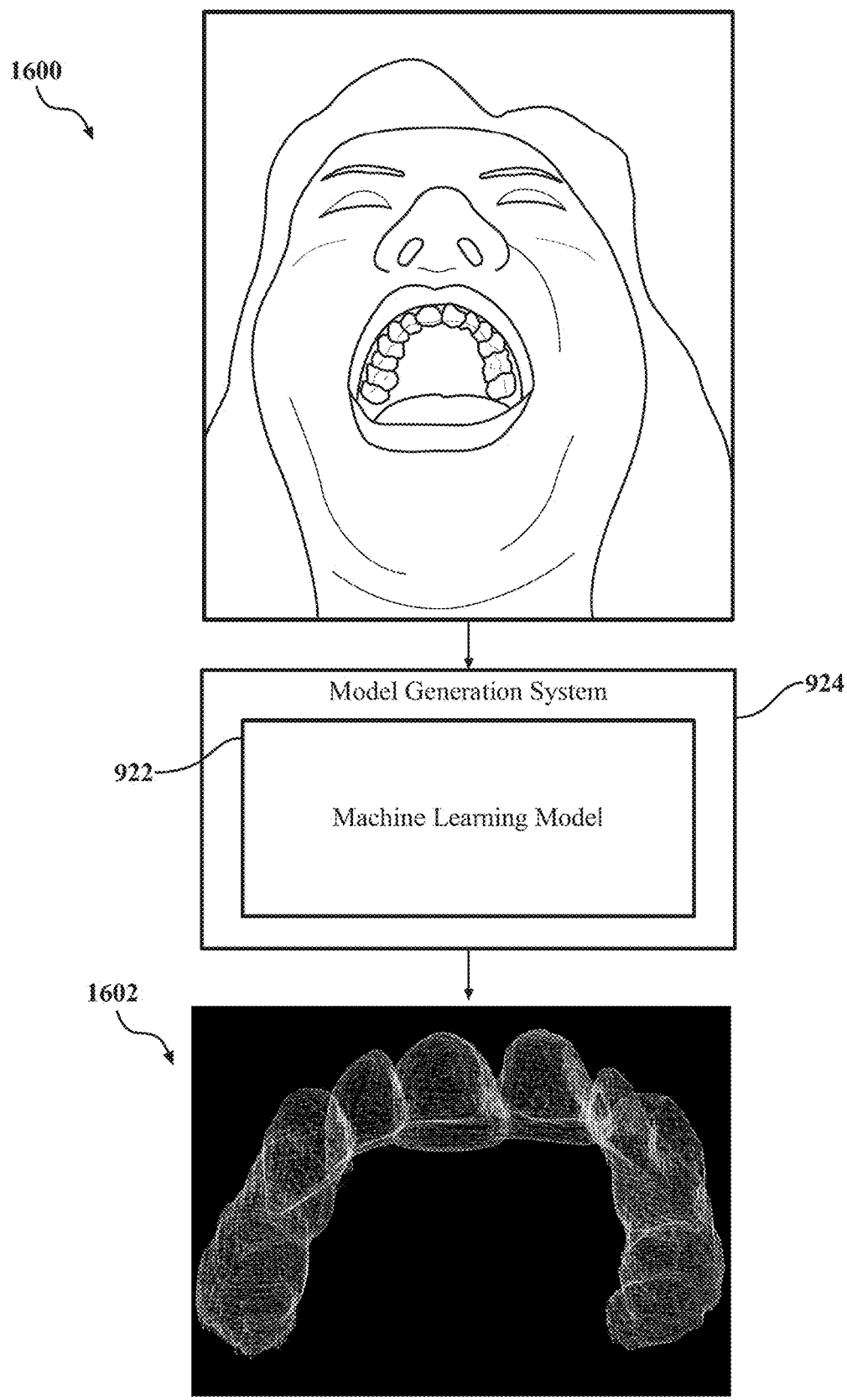
FIG. 16 is an illustration of a use case diagram of the system of FIG. 9, according to an illustrative embodiment.

Referring now to FIG. 16, a use case diagram of the system 900 of FIG. 9 is shown, according to an illustrative embodiment. In some embodiments, and as shown in FIG. 16, a user may upload one or more images (such as image 1600) that include a representation of the user's teeth. In some embodiments, the user may capture images from different perspectives, such as those shown in FIG. 3A-FIG. 3C. In some embodiments, the user may capture images of their own teeth. In some embodiments, a different person may capture images of the user's teeth (e.g., from the user's device or from a different device). The user may provide the image 1600 to the model generation system 924. The model generation system 924 may apply the image 1600 to the trained machine learning model 922 (e.g., as an input) to generate a 3D model 1602 based on the image 1600.

Accordingly, the machine learning model 922 is trained to use an image 1600 received from a user to generate a 3D model 1602.

In some embodiments, some of the results (e.g., 3D models) generated via the machine learning model 922 may be used for refining the machine learning model 922 and/or other processes for generating subsequent models. For example, a user performing a quality review or check of the 3D models generated via the machine learning model 922 may further refine parameters (such as the configuration parameters) based on the outputs of the machine learning models.

Figure 17:
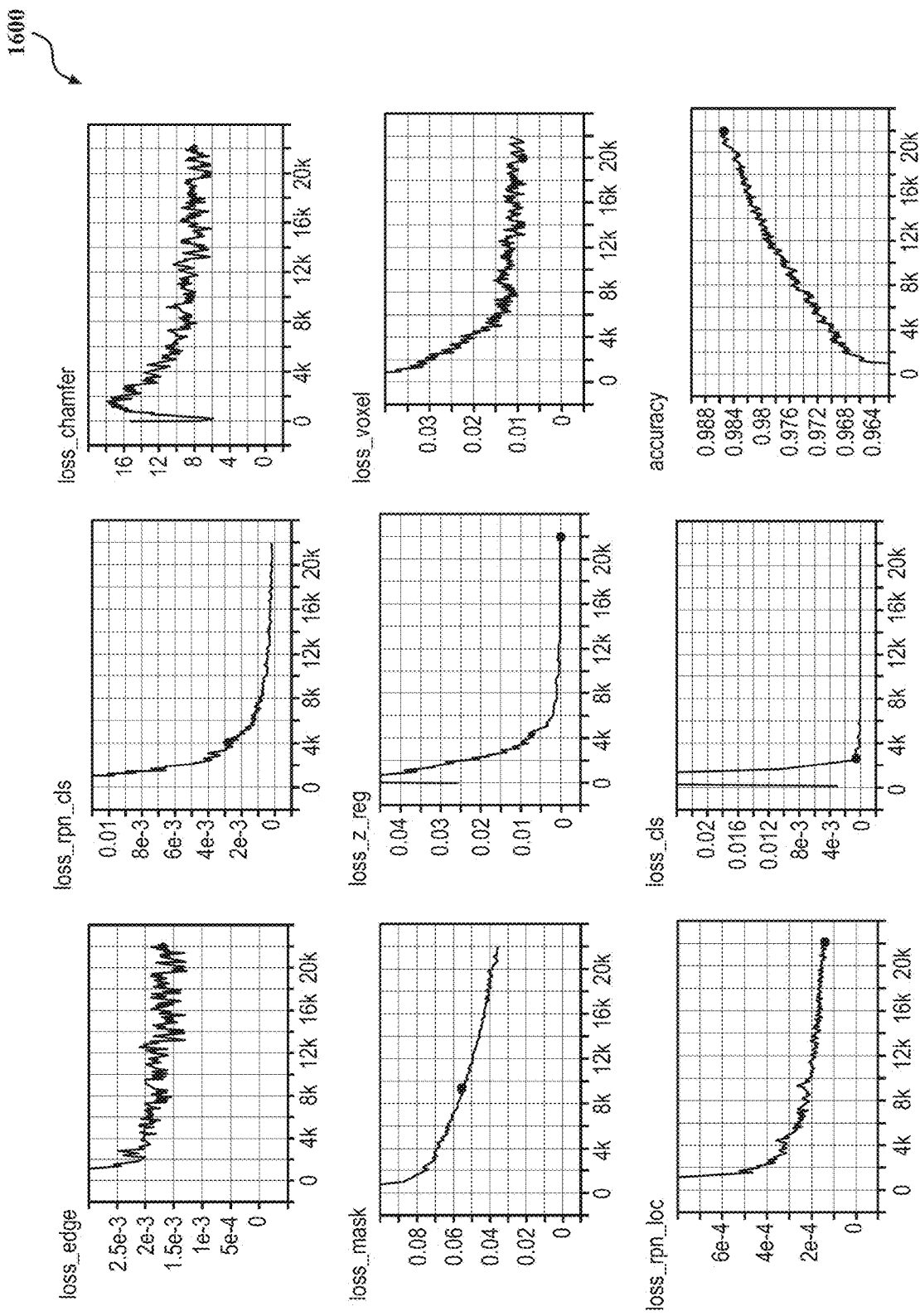
FIG. 17 are illustrations of a series of graphs corresponding to training of a machine learning model of the system of FIG. 9, according to an illustrative embodiment.
Figure 18:
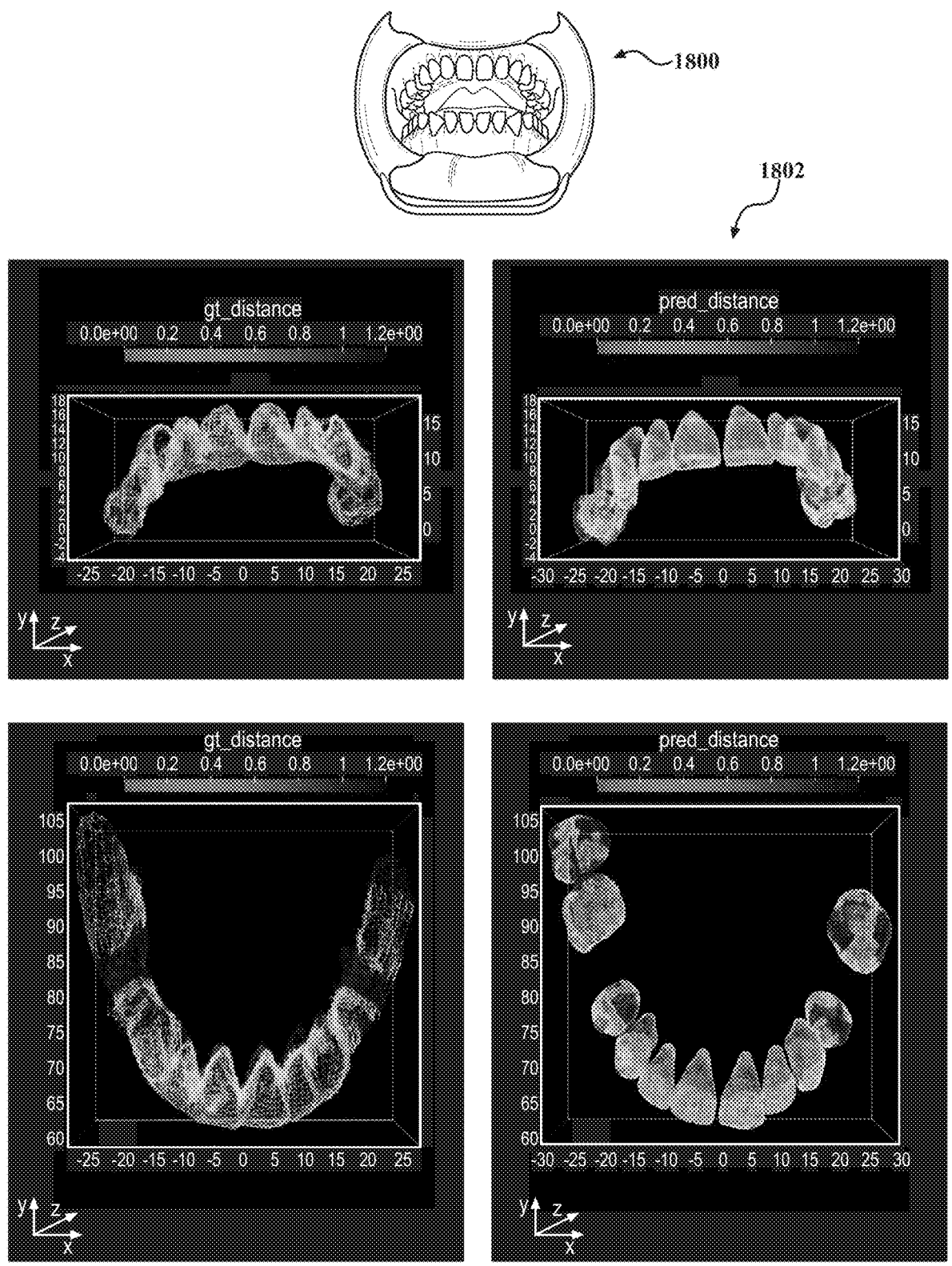
FIG. 18 are illustrations of a series of model evaluation interfaces corresponding to a model generated by the machine learning model of the system of FIG. 9, according to an illustrative embodiment.

Referring now to FIGS. 16 and 17, a series of graphs 1700 corresponding to training of the machine learning model 922 is shown in FIG. 17, and a series of model evaluation interfaces 1802 showing a model generated by the machine learning model 922 based on an image 1800 from a user is shown in FIG. 18. Each of the graphs 1700 shown in FIG. 17 may be representative of metrics of each model used to train the machine learning model 922. Such metrics may include or correspond to configuration parameters 918 that are used for training the machine learning model 922. Correspondingly, a person performing quality control of the machine learning model 922 may view the graphs 1700 shown in FIG. 17 and interfaces 1802 to modify various configuration parameters 918 for updating or otherwise refining the training of the machine learning model 922. Various examples of configuration parameters 918 which may be represented in graphs 1700 include loss edge, loss region proposal network (RPN), classification (CLS), loss chamfer, loss mask, loss z regression (REG), loss voxel, loss RPN local, loss classification, accuracy, etc. Additional examples of configuration parameters 181 which may be represented in graphs 1700 include data time, estimated time of arrival (ETA) in seconds, fast regions with convolutional neural network (R-CNN), loss normal, mask R-CNN, region of interest (ROI) head, RPN, time, total loss, and voxel R-CNN. While these configuration parameters 918 are described, it is noted that the machine learning model 922 may be trained or configured to leverage various combinations of these (and other) configuration parameters 918. The graphs 1700 and interfaces 1802 may be rendered on the computing device 910. A technician viewing the graphs 1700 and interfaces 1802 may adjust, tune, or otherwise revise one or more of the configuration parameters 918 to modify the machine learning model 922. In some embodiments, the computing device 910 may automatically adjust, tune, or otherwise revise the configuration parameters 918, or may make recommendations of changes to configuration parameters 918 for acceptance by the technician. Such embodiments may provide for a more accurate tuning of the configuration parameters 918 for training the machine learning model 922.

Figure 19:
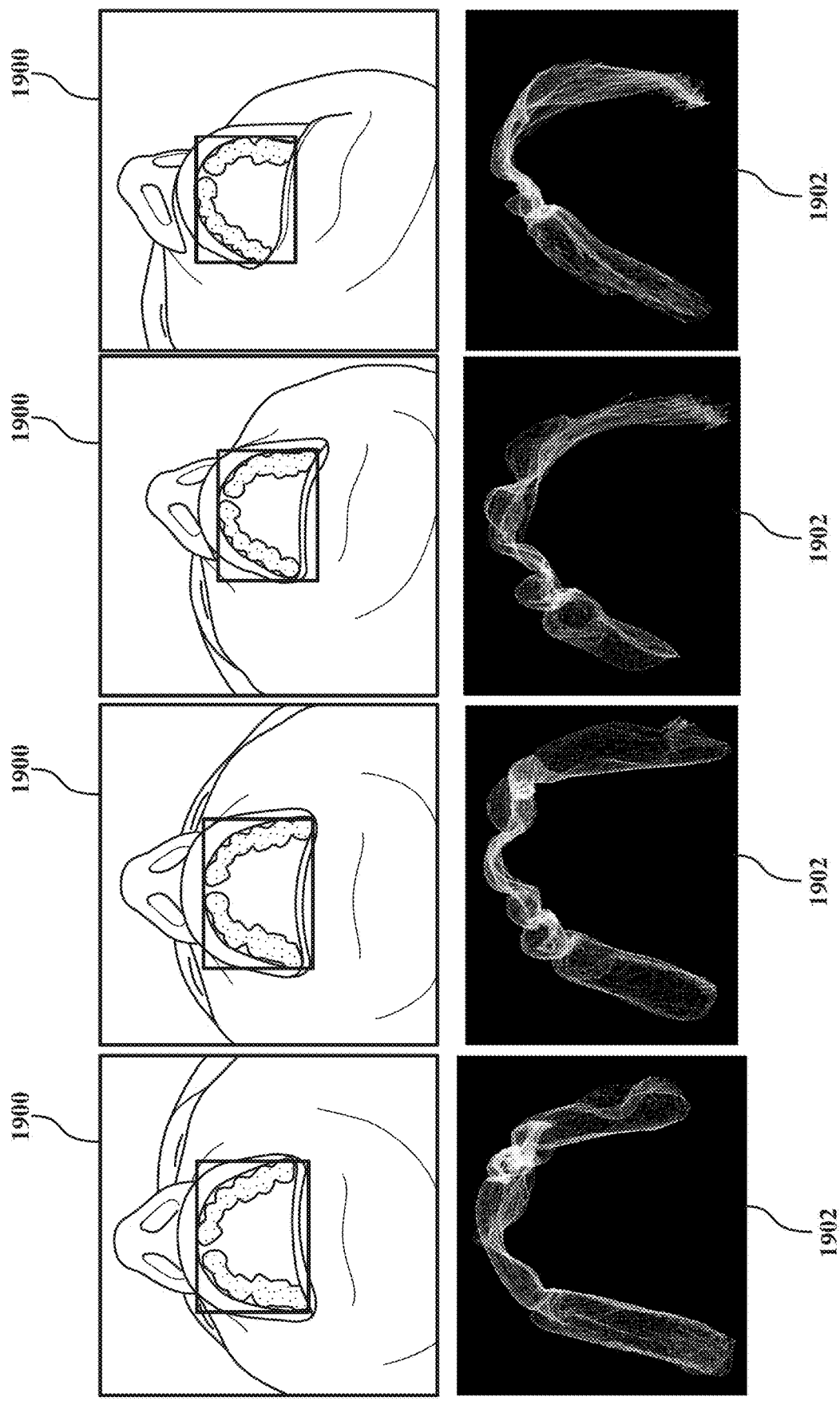
FIG. 19 is an illustration of a series of images of a user and a corresponding series of 3D models generated using the machine learning model of the system of FIG. 9, according to an illustrative embodiment.

Referring now to FIG. 19, a series of images 1900 of a user and a corresponding series of 3D models 1902 which are generated using the machine learning model 922 are shown. As shown in FIG. 19, a dental arch of the user is represented in the images 1900. The models 1902 shown in FIG. 19 are separate 3D models which are generated from the plurality of images 1900 by the machine learning model 922. As such, the machine learning model 922 may generate the plurality of 3D models 1902 from a plurality of images 1900 of the user's dental arch (e.g., from different perspectives). In some embodiments, the model generation system 924 may generate a merged 3D model from the plurality of 3D models 1902. As described above, the model generation system 924 may combine, fuse, or otherwise merge the plurality of 3D models 1902 to form a merged 3D model of the dental arch. The 3D models may be merged as described above to form the merged model 1902. As shown in FIG. 19, through the implementations and embodiments described above, the machine learning model 922 may generate 3D models from different views, which may be merged and together model an entire dental arch, including occlusal regions, which may be difficult to model. While some of the processes set forth above and depicted in the Figures describe training machine learning models and generating models of dental arches using images of a person's teeth, in these instances it will be appreciated that a similar methodology can be applied to training machine learning models for processing images of dental impressions taken of a dental arch of a user and generating models based on such images of dental impressions.

Figure 20:
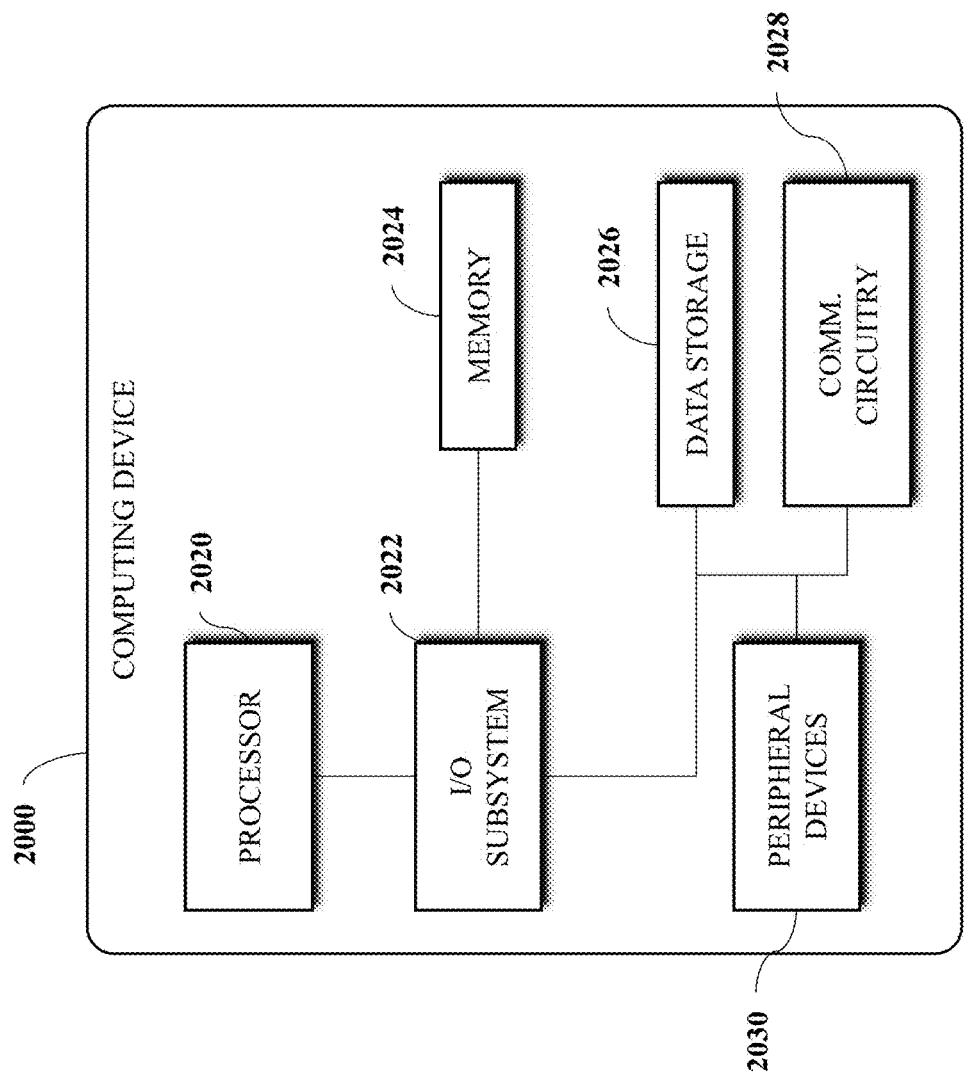
FIG. 20 is a block diagram of at least one embodiment of a computing device for merging three-dimensional models, according to an illustrative embodiment.

Referring now to FIG. 20, an illustrative computing device 2000 for merging three-dimensional models of dental impressions is shown. In use, as described further below, the computing device 2000 generates or otherwise acquires three-dimensional models for each of multiple dental impressions. For example, multiple dental impressions created by a user with an at-home dental impression kit may be scanned to generate the three-dimensional models. The computing device 2000 automatically merges geometry from the models to generate a complete model of one or more of the user's dental arches. In some embodiments, the computing device 2000 may use multiple merge strategies and select the best merged model. Thus, the computing device 2000 may generate a higher-quality merged model as compared to any of the individual models. Additionally, the computing device 2000 may be able to generate a complete model from multiple incomplete dental impressions, which may improve the proportion of at-home dental kits that are successfully completed and/or reduce the number of retake impression kits that are sent to users (e.g., customers).

The computing device 2000 may be embodied as any type of computation or computer device capable of performing the functions described herein, including, without limitation, a computer, a server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. As such, the computing device 2000 may be embodied as a single server computing device or a collection of servers and associated devices. For example, in some embodiments, the computing device 2000 may be embodied as a "virtual server" formed from multiple computing devices distributed across a network and operating in a public or private cloud. Accordingly, although the computing device 2000 is illustrated in FIG. 1 and described below as embodied as a single server computing device, it should be appreciated that the computing device 2000 may be embodied as multiple devices cooperating together to facilitate the functionality described below.

As shown in FIG. 20, the computing device 2000 illustratively include a processor 2020, an input/output subsystem 2022, a memory 2024, a data storage device 2026, and a communication subsystem 2028, and/or other components and devices commonly found in a server computer or similar computing device. Of course, in other embodiments, the computing device 2000 may include other or additional components, such as those commonly found in a server computer (e.g., various input/output devices). Additionally, in some embodiments, one or more of the illustrative components may be incorporated in, or otherwise form a portion of, another component. For example, the memory 2024, or portions thereof, may be incorporated in the processor 2020.

The processor 2020 may be embodied as any type of processor capable of performing the functions described herein. The processor 2020 may be embodied as a single or multi-core processor(s), digital signal processor, microcontroller, or other processor or processing/controlling circuit. Similarly, the memory 2024 may be embodied as any type of volatile or non-volatile memory or data storage capable of performing the functions described herein. In operation, the memory 2024 may store various data and software used during operation of the computing device 2000, such as operating systems, applications, programs, libraries, and drivers. The memory 2024 is communicatively coupled to the processor 2020 via the I/O subsystem 2022, which may be embodied as circuitry and/or components to facilitate input/output operations with the processor 2020, the memory 2024, and other components of the computing device 2000. For example, the I/O subsystem 2022 may be embodied as, or otherwise include, memory controller hubs, input/output control hubs, platform controller hubs, integrated control circuitry, firmware devices, communication links (i.e., point-to-point links, bus links, wires, cables, light guides, printed circuit board traces, etc.) and/or other components and subsystems to facilitate the input/output operations. In some embodiments, the I/O subsystem 2022 may form a portion of a system-on-a-chip (SoC) and be incorporated, along with the processor 2020, the memory 2024, and other components of the computing device 2000, on a single integrated circuit chip.

The data storage device 2026 may be embodied as any type of device or devices configured for short-term or long-term storage of data such as, for example, memory devices and circuits, memory cards, hard disk drives, solid-state drives, or other data storage devices. The communication subsystem 2028 of the computing device 2000 may be embodied as any communication circuit, device, or collection thereof, capable of enabling communications between the computing device 2000 and other remote devices over a network. The communication subsystem 2028 may be configured to use any one or more communication technology (e.g., wired or wireless communications) and associated protocols (e.g., Ethernet, InfiniBand®, Bluetooth®, WiMAX, etc.) to effect such communication.

As shown, the computing device 2000 may also include one or more peripheral devices 130. The peripheral devices 130 may include any number of additional input/output devices, interface devices, and/or other peripheral devices. For example, in some embodiments, the peripheral devices 130 may include a display, touch screen, graphics circuitry, keyboard, mouse, speaker system, microphone, network interface, and/or other input/output devices, interface devices, and/or peripheral devices.

Figure 21:
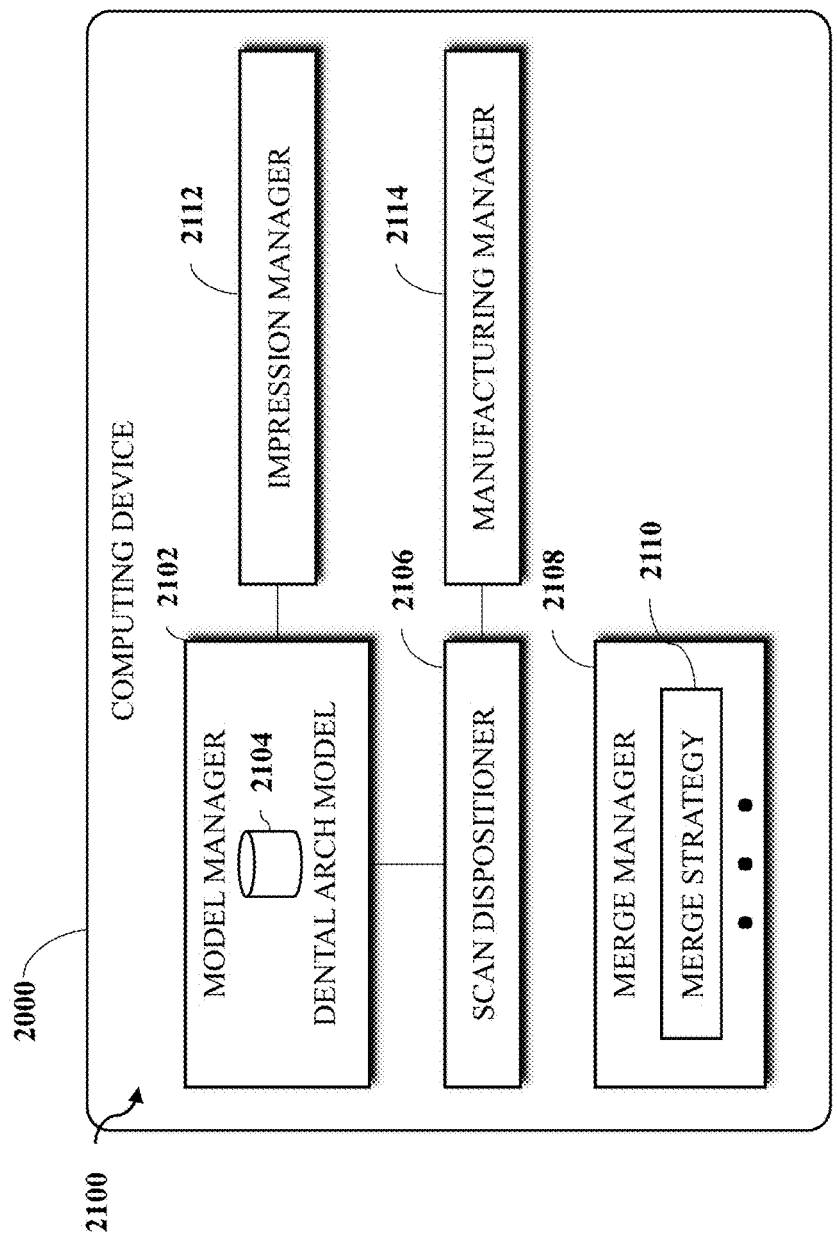
FIG. 21 is a block diagram of at least one embodiment of an environment that may be established by the computing device of FIG. 20, according to an illustrative embodiment.

Referring now to FIG. 21, in an illustrative embodiment, the computing device 2000 establishes an environment 2100 during operation. The illustrative environment 2100 includes model manager 2102, a scan dispositioner circuitry 2106, a merge manager 2108, an impression manager 2112, and a manufacturing manager 2114. The various components of the environment 2100 may be embodied as hardware, firmware, software, or a combination thereof. As such, in some embodiments, one or more of the components of the environment 2100 may be embodied as circuitry or collection of electrical devices (e.g., model manager circuitry 2102, scan dispositioner circuitry 2106, merge manager circuitry 2108, impression manager circuitry 2112, and/or manufacturing manager circuitry 2114). It should be appreciated that, in such embodiments, one or more of the model manager circuitry 2102, the scan dispositioner circuitry 2106, the merge manager circuitry 2108, the impression manager circuitry 2112, and/or the manufacturing manager circuitry 2114 may form a portion of one or more of the processor 2020, the I/O subsystem 2022, and/or other components of the computing device 2000. For instance, the model manager 2102, merge manager 2108, manufacturing manager 2114, etc. may be implemented as one or more processor(s) 2020 of the computing device 2000, as one or more processing circuits, or other types of hardware. Additionally, in some embodiments, one or more of the illustrative components may form a portion of another component and/or one or more of the illustrative components may be independent of one another.

The model manager 2102 is configured to generate multiple models 2104. Each model 2104 may be embodied as a three-dimensional model indicative of a dental impression of a client's dental arch (e.g., mandibular arch or maxillary arch). The models 2104 may be generated by the model generation system described above with respect to FIG. 2-FIG. 19. As described below, the model manager 2102 may be further configured to generate additional models 2104 if a merged model 2104 is not indicative of the complete anatomy of a customer's dental arch.

The scan dispositioner circuitry 2106 is configured to determine whether a model 2104 (including a merged model 2104) is indicative of a complete anatomy of the customer's dental arch. That determination may be based on quality review data provided for each model 2104 by a technician.

The merge manager 2108 is configured to merge two models 2104 using a merge strategy 2110 to generate a merged model 2104 if an original input model 2104 is not indicative of the complete anatomy of the customer's dental arch. Each merge strategy 2110 may be embodied as any algorithm, process, policy, or other strategy that may be used to select geometry from the input models 2104 to be included in the merged model 2104. In some embodiments, the merge manager 2108 may be configured to merge the models 2104 using multiple merge strategies 2110 to generate multiple merge models 2104. The merge manager 2108 may be configured to select a merged model 2104 from multiple results, for example, by receiving a selection of the best-merged model 2104 from a technician.

To perform the merge, the merge manager 2108 may be configured to align geometry of the models 2104 based on a common point or other common location. The merge manager 2108 is configured to select geometry from either of the models 2104 using the merge strategy 2110. The selected geometry is associated with a common anatomical location in the customer's dental arch. Selecting the geometry using the merge strategy 2110 may include, for example, determining which of the dental impressions associated with the models 2104 includes more detail associated with the common anatomical location and/or determining which of the models 2104 includes greater depth associated with the common anatomical location. In some embodiments, the merge strategy 2110 may include one or more of the steps described below with reference to FIG. 24-FIG. 30. The merge manager 2108 may be further configured to clean (or smooth) the merged model 2104 to generate a closed surface, for example, by performing Poisson surface reconstruction or by performing a gap closing (or smoothing) algorithm.

The impression manager 2112 may be configured to obtain additional dental impressions if the input models 2104 and/or the merged model 2104 do not include a complete representation of the customer's dental arch. The manufacturing manager 2114 may be configured to use the input models 2104 and/or the merged model 2104 for sculpting and setup or otherwise use the models 2104 for manufacturing.

Figure 22:
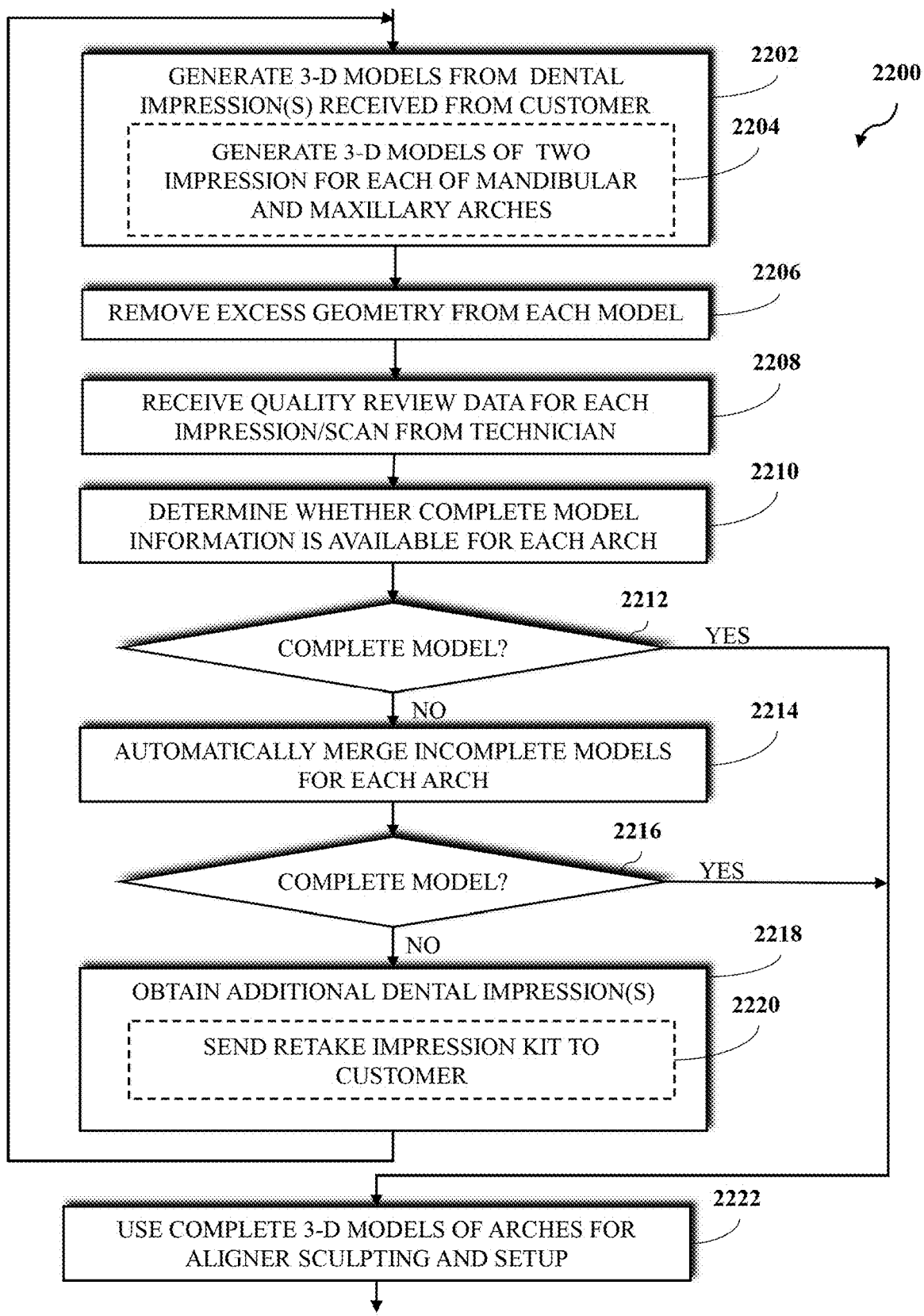
FIG. 22 is a flow diagram of at least one embodiment of a method for capturing and processing three-dimensional scans of dental impressions that may be executed by the computing device of FIGS. 20 and 21, according to an illustrative embodiment.

Referring now to FIG. 22, in use, the computing device 2000 may execute a method 2200 for capturing and processing three-dimensional models of dental impressions. It should be appreciated that, in some embodiments, the operations of the method 2200 may be performed by one or more components of the environment 2100 of the computing device 2000 as shown in FIG. 2. The method 2200 begins in block 2202, in which the computing device 2000 generates 3D models 2104 of one or more dental impressions from images received from a customer. The computing device 2000 may use, implement, or otherwise include the components described above with respect to FIG. 2-FIG. 19 for generating the 3D models 2104. Each model 2104 may be embodied as a three-dimensional representation of the geometry of a dental impression, which is in turn a negative representation of a dental arch (e.g., a mandibular arch or maxillary arch) of the customer. Illustratively, the models 2104 are embodied as standard triangle language (STL) files that describe the surface geometry of the corresponding dental impressions. In other embodiments, the models 2104 may be embodied as any surface or solid three-dimensional modeling data.

The computing device 2000 may generate 3D models 2104 for several impressions produced by the customer in connection with an at-home dental impression kit. For example, in some embodiments, in block 2204, the computing device 2000 may generate 3D models 2104 for two impressions for each of the customer's mandibular arch (i.e., the customer's lower teeth) and the customer's maxillary arch (i.e., the customer's upper teeth), producing a total of four models 2104. Additionally or alternatively, in some embodiments, the computing device 2000 may generate 3D models 2104 for a different number of dental impressions. For example, as described further below, a retake kit may include multiple dental impressions for one or more of the user's dental arches.

In block 2206, the computing device 2000 removes excess geometry from each model 2104. The excess geometry may be removed, for example, by a technician using a 3-D editor, or may be removed automatically.

In block 2208, the computing device 2000 receives quality review data for each impression/scan from a technician. The technician may, for example, interactively view a representation of each model 2104 and then provide the quality review data. The quality review data may indicate whether the corresponding dental impression includes a complete impression of the user's dental arch. Due to incorrect use by the customer or other factors, a dental impression may not include clear impressions of one or more teeth or other areas of a dental arch. Thus, in some embodiments, the quality review data may identify incomplete areas of each arch (e.g., incomplete sides, teeth, or other parts of the impression).

In block 2210, for each of the mandibular arch and the maxillary arch, the computing device 2000 determines whether one of the models 2104 is complete. For example, the computing device 2000 may determine whether any of the models 2104 includes data for a complete impression of a dental arch using the quality review data. In block 2212, the computing device 2000 checks whether a model 2104 is complete for both of the dental arches. If so, the method 2200 branches ahead to block 2222, described below. If a model 2104 is not complete for either arch, the method 2200 advances to block 2214.

In block 2214, for one or more of the dental arches, the computing device 2000 automatically merges incomplete models 2104 to generate a merged model 2104. For example, the computing device 2000 may merge two models 2104 of the customer's mandibular arch and/or may merge two models 2104 of the customer's maxillary arch. The computing device 2000 may use one or more merge strategies 2110 to select geometry from one of the models 2104 and replace geometry in the other model 2104 with the selected geometry. Thus, after merging, the merged model 2104 may include geometry generated from more than one dental impression. One potential embodiment of a method for automatically merging the models 2104 is described below in connection with FIG. 23.

In block 2216, for each of the mandibular arch and the maxillary arch, the computing device 2000 checks whether one of the models 2104, including the merged model 2104, is complete. If so, the method 2200 branches ahead to block 2222, described below. If a model 2104 is not complete, the method 2200 advances to block 2218.

In block 2218, the computing device 2000 obtains 3D models 2104 for additional dental impressions for the incomplete dental arch(es). In some embodiments, in block 2220 the computing device 2000 may cause a retake impression kit to be sent to the customer. The retake impression kit may include materials (e.g., dental trays and thixotropic impression material) to create one or more dental impressions for the incomplete dental arch or arches. After administering additional dental impressions, the customer may upload images of the additional dental impressions, which may be used for generating the additional 3D models 2104. The method 2200 loops back to block 2202, in which the additional 3D models 2104 may be checked for completeness, and potentially merged with the existing models 2104.

Referring back to block 2216, if a model 2104 is complete for both of the dental arches, then the method 2200 advances to block 2222, in which the computing device 2000 uses the complete models 2104 of the customer's dental arches to perform sculpting and setup. For example, a complete model 2104 may be used to generate a three-dimensional treatment plan for the customer, to generate or manufacture a positive model of the customer's dental arches, and/or to manufacture invisible aligners for the customer. After using the complete models 2104, the method 2200 is completed. The method 2200 may be executed again for an additional customer and/or for additional dental impressions.

Figure 23:
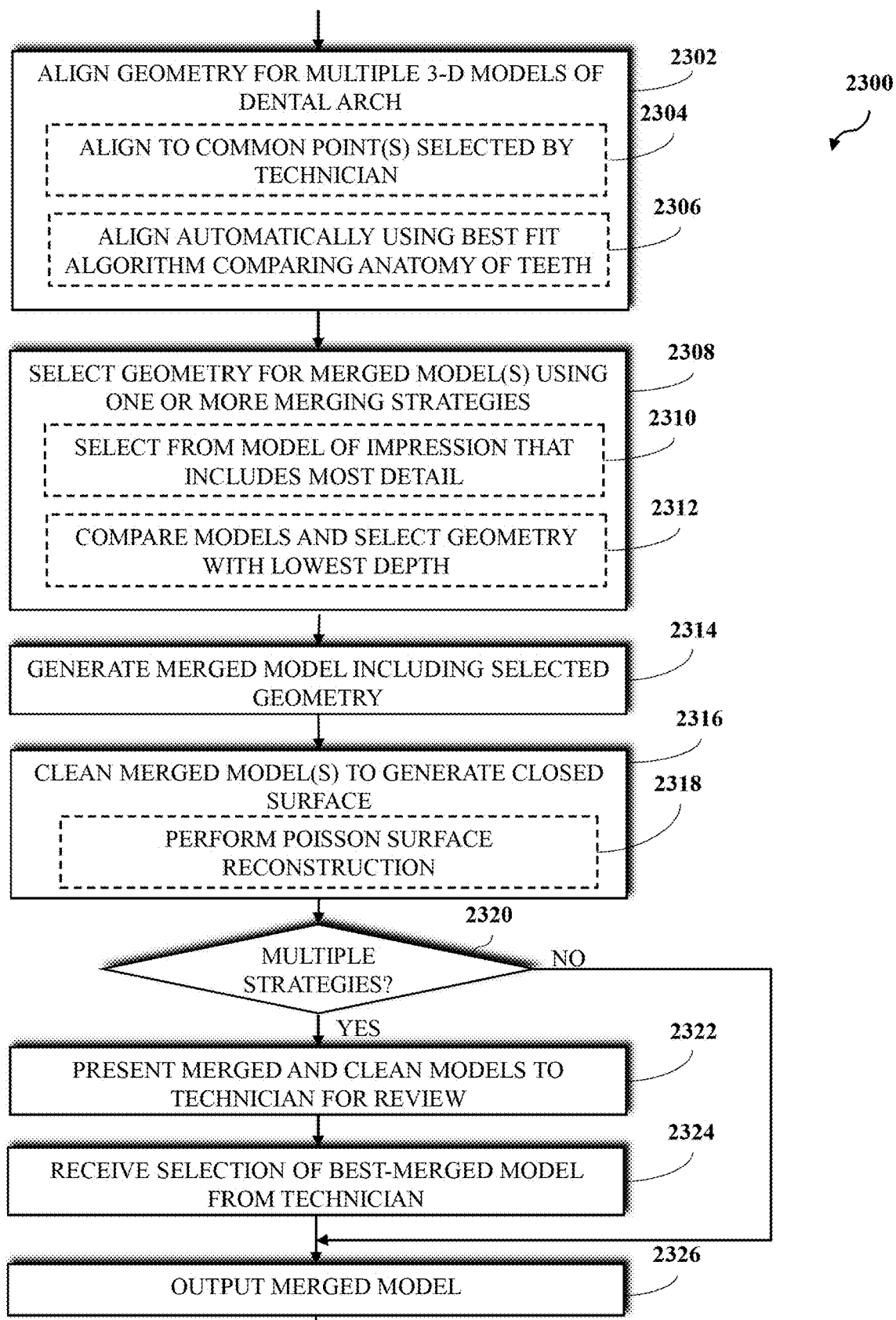
FIG. 23 is a flow diagram of at least one embodiment of a method for merging three-dimensional models that may be executed by the computing device of FIGS. 20 and 21, according to an illustrative embodiment.

Referring now to FIG. 23, in use, the computing device 2000 may execute a method 2300 for merging three-dimensional models. The method 2300 may be executed in connection with block 2214 of FIG. 22, as described above. It should be appreciated that, in some embodiments, the operations of the method 2300 may be performed by one or more components of the environment 2100 of the computing device 2000 as shown in FIG. 2. The method 2300 begins in block 2302, in which the computing device 2000 aligns the geometry of multiple models 2104. Each of the models 2104 may be generated from images of a dental impression of one of the customer's dental arches. For example, the computing device 2000 may merge two models 2104 associated with the mandibular arch of the customer or may merge two models 2104 associated with the maxillary arch of the customer. The geometry of the models 2104 is aligned according to the underlying geometry of the dental impressions and, therefore, the corresponding anatomy of the customer's dental arches. In some embodiments, in block 2304 the models 2104 may be aligned to one or more common points selected by a technician. For example, the technician may interactively identify teeth or other common features in each of the models 2104. In some embodiments, in block 2306 the models 2104 may be aligned automatically using a best fit algorithm that compares the anatomy of the teeth represented in each of the models 2104. One embodiment of aligning the models 2104 is described below in connection with FIG. 30.

After aligning the geometry, in block 2308 the computing device 2000 selects geometry from the models 2104 to include in a merged model 2104 using one or more merge strategies 2110. The computing device 2000 may select geometry from a model 2104 to fill in incomplete parts of the other model 2104. In some embodiments, in block 2310, the computing device 2000 may select geometry from the model 2104 corresponding to the dental impression that includes the most detail of the user's anatomy. For example, the computing device 2000 may select geometry from a model 2104 of a dental impression that captures the customer's anatomy from the tip of the teeth to the gingival line.

In some embodiments, in block 2312 the computing device 2000 may compare the models 2104 and select geometry from the model 2104 having the greatest depth. In other words, the computing device 2000 may select geometry from the model 2104 with the greatest distance from the bottom of the impression (e.g., corresponding to the tip of a tooth) up to the top of the impression (e.g., the surface of the impression mixture). For example, the computing device 2000 may combine the models 2104 into multiple layers, and then select lower points from the layers. Having lower depth in the model 2104 indicates that the dental impression was also deeper, and deeper dental impressions tend to capture greater detail of the customer's tooth and gum anatomy. Additionally, using the deeper model 2104 may remove noise from the model 2104, such as spikes in the impression caused by the impression mixture pulling up as the impression is removed from the customer's teeth.

In block 2314, the computing device 2000 generates the merged model 2104 including the selected geometry. The merged model 2104 may include 3D geometry from both of the models 2104, with the less-detailed components of the geometry removed.

In block 2316, the computing device 2000 may clean the merged model 2104 to generate a closed surface, also known as a watertight mesh. In some embodiments, the model 2104 may be embodied as a mesh or other surface model, and that mesh may include holes or be otherwise open. Generating a closed surface may allow the merged model 2104 to define a solid object that can, for example, be input to a 3-D printer. The computing device 2000 may use any technique to clean the merged model 2104. In some embodiments, in block 2318 the computing device 2000 may perform Poisson surface reconstruction to generate the closed surface. Additionally or alternatively, in some embodiments the computing device 2000 may perform a gap closing algorithm for surface reconstruction to generate the closed surface.

In block 2320, the computing device 2000 determines whether multiple merge strategies 2110 were used to generate multiple merged models 2104. As described above in connection with block 2308, the computing device 2000 may use more than one merge strategy 2110 to merge the models 2104. Each merge strategy 2110 may generate a different merged model 2104. If a single merge strategy 2110 is used, the method 2300 branches ahead to block 2326. If more than one merge strategy 2110 is used, the method 2300 advances to block 2322.

In block 2322, the computing device 2000 presents the merged and cleaned models 2104 generated using the multiple merge strategies 2110 to a technician for review. In block 2324, the computing device 2000 receives a selection of a merged model 2104 from the technician. The technician may, for example, manually select the best-merged model 2104.

In block 2326, the computing device 2000 outputs the merged model 2104. As described above in connection with FIG. 22, if the merged model 2104 is complete, it may be used to prepare a three-dimensional treatment plan for the customer, to generate or manufacture a positive model of the customer's dental arches, to manufacture invisible aligners for the customer, or otherwise be used for dental treatment. After outputting the merged model 2104, the method 2300 is completed. The method 2300 may be executed repeatedly to perform additional merges.

Figure 24:
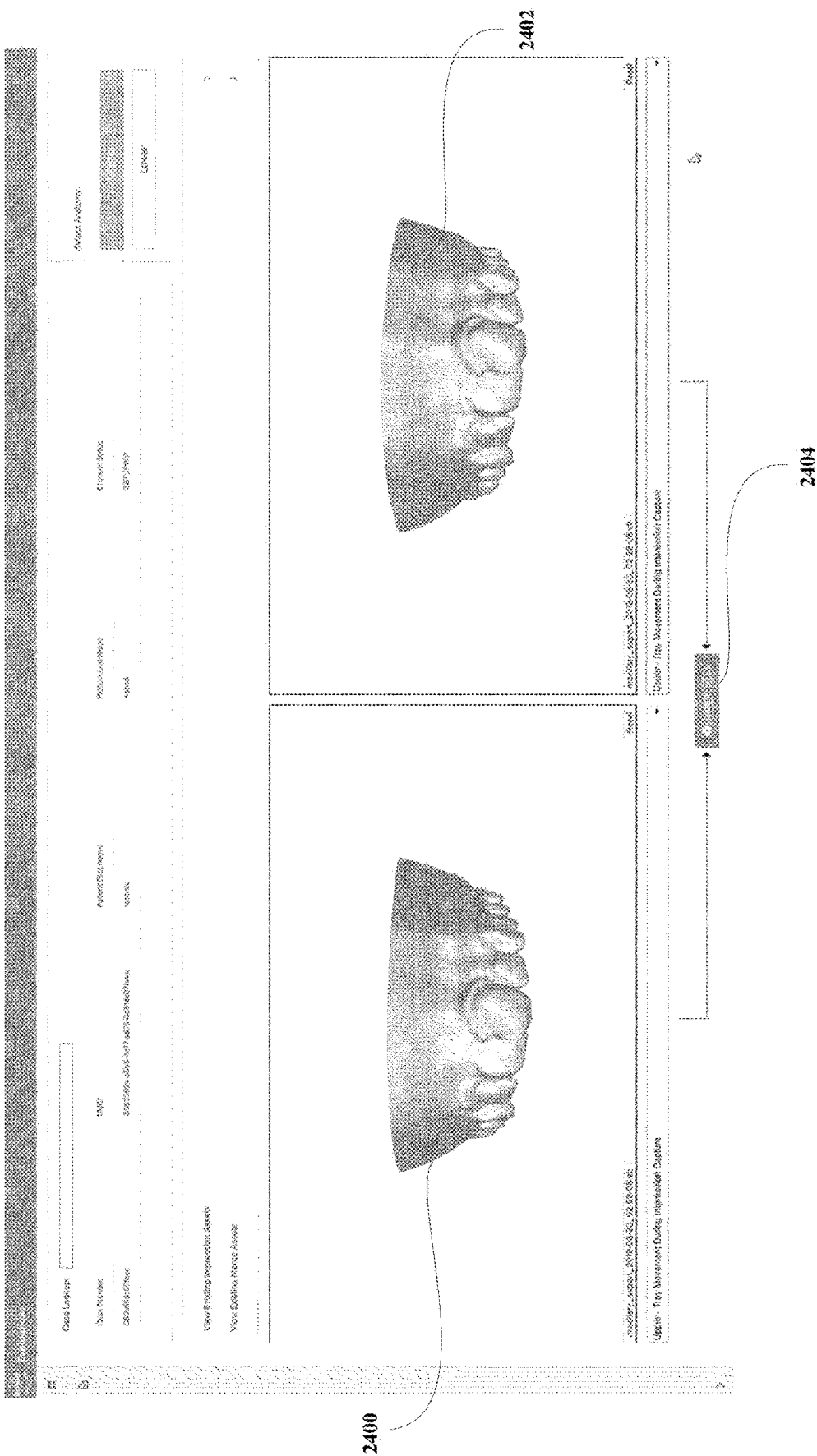
FIG. 24 is a user interface for uploading first and second models to be merged, according to an illustrative embodiment.
Figure 25:
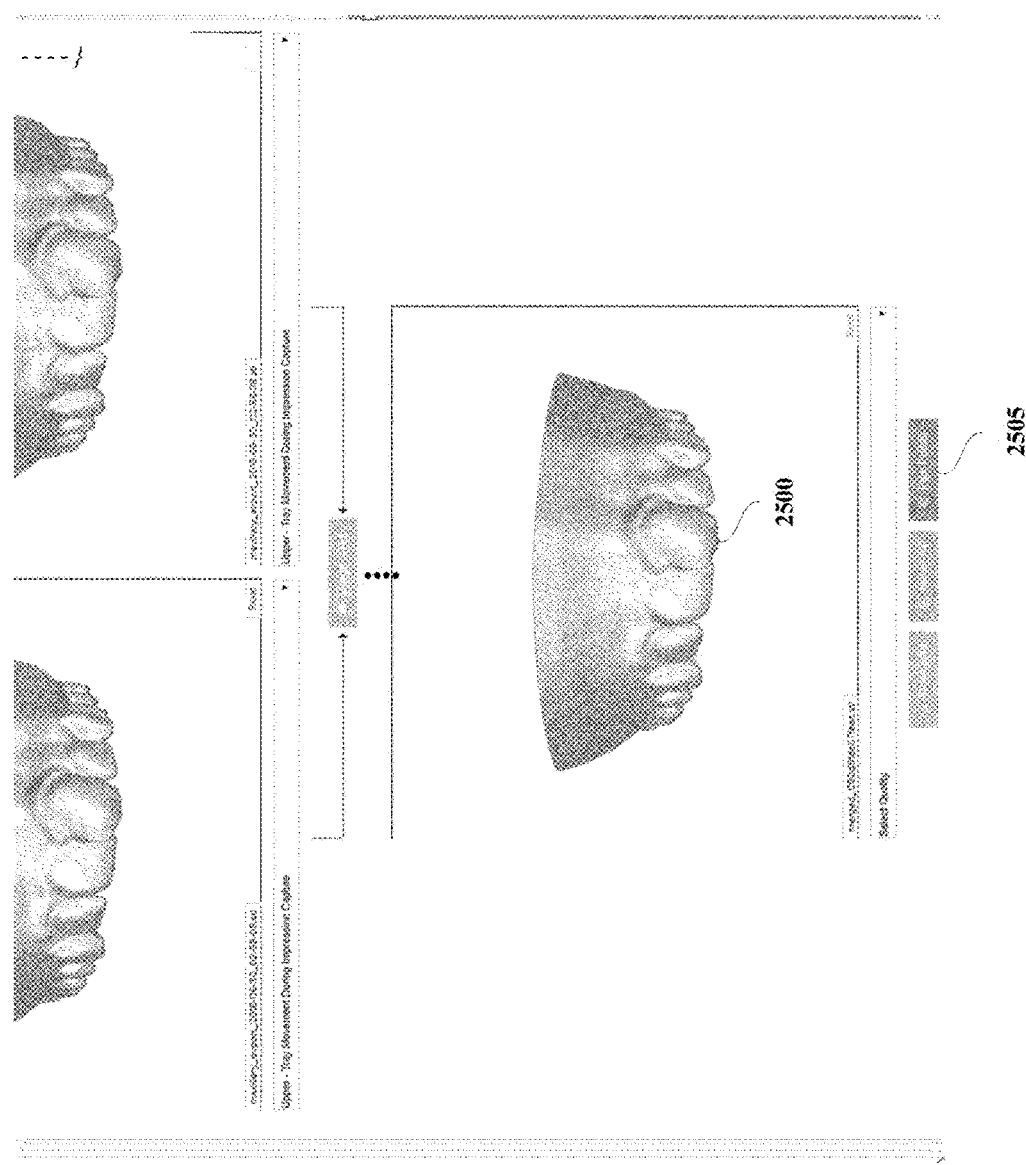
FIG. 25 is a user interface showing a rough merge of the first and second models of FIG. 24, according to an illustrative embodiment.
Figure 26:
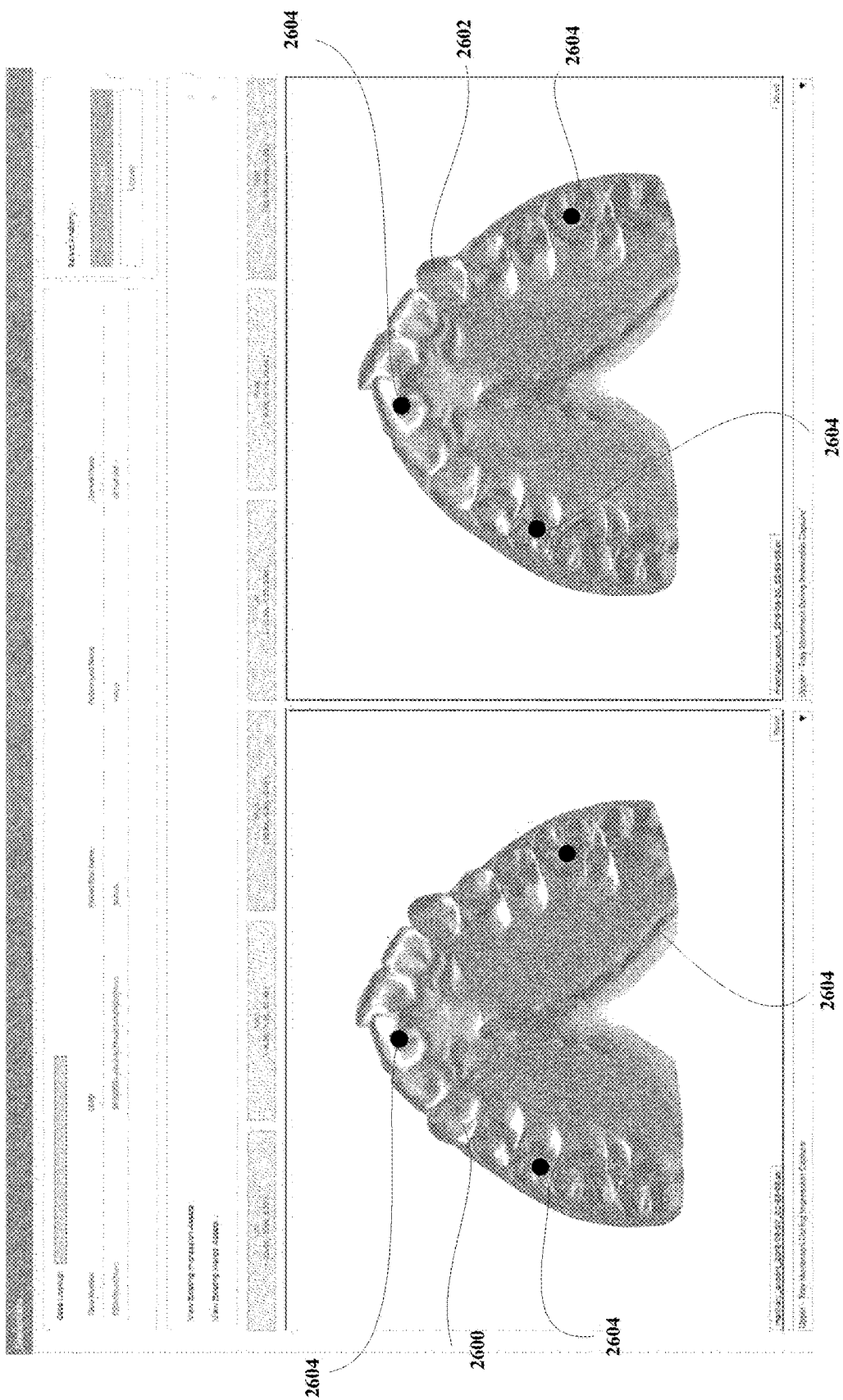
FIG. 26 is a user interface showing the occlusal surface of the first and second models of FIG. 24 for selecting correlation points in the two models, according to an illustrative embodiment.

Referring now to FIG. 24-FIG. 26, various user interfaces are shown for generating a merged model 2104, according to exemplary embodiments. Specifically, FIGS. 24-26 depict a series of user interfaces which may be used for merging two or more models 2104 to output a merged model 2104. In some embodiments, the user interfaces may be operated, controlled, or otherwise used by a user of the computing device 2000. In some embodiments, one or more of the steps outlined below may be automated (and thus the user interface corresponding to such steps may be omitted or modified).

FIG. 24 depicts a user interface for uploading models to be merged. The models may be represented in various file formats. For instance, the models may be represented as geometric faces coupled to one another according to a surface contour. In some embodiments, the geometric faces may be triangles (e.g., the file format may be STL). Each triangle may be joined at the sides by adjacent triangles proximate thereto. Hence, the triangles form a mesh which represents the surface contour or geometry of the user's mouth, or at least the user's teeth and gums (as captured by the dental impression). As described above, the model manager 2102 is configured to generate and store multiple models 2104. Such models 2104 may include a first model 2400 and a second model 2402. The first model 2400 and second model 2402 are representations of the same dental arch of a user. For example, the first model 2400 can be captured at a first time and the second model 2402 can be captured at a second time (e.g., shortly after the first model 2400 is captured).

In some embodiments, a user uploads the first model 2400 and second model 2402 to the computing device 2000 (e.g., for use by the model manager 2102). The user may select or otherwise provide an address to a file location corresponding to the first and second models 2400, 2402, drag and drop the files corresponding to the models 2400, 2402 into a workspace, a file upload box, or other user interface element which may be used for uploading files to the computing device 2000. In some embodiments, the model manager 2102 automatically retrieves the first and second models 2400, 2402 (e.g., based on a creation time, based on a file name, etc.). In each of these embodiments, the model manager 2102 receives, acquires, obtains, or otherwise generates and includes the first model 2400 and second model 2402.

The user may select (or the model manager 2102 may automatically initiate) a merge model option 2404. The merge model option 2404 is shown to be represented as a button ("Merge STLs") on the user interface, though the merge model option 2404 may be implemented in other ways via the user interface.

Upon selection and/or initiation of the merge model option 2404, the merge manager 2108 may be configured to generate a rough merge 2500 of the model. FIG. 25 shows a rough merge of the first and second models 2400, 2402, according to an exemplary embodiment. The merge manager 2108 may generate the rough merge 2500 in a number of ways. The merge manager 2108 may identify, estimate, etc., corresponding anatomical features between the first model 2400 and second model 2402. For instance, the merge manager 2108 may match crowns in the first model 2400 with crowns in the second model 2402. The user is then prompted to select correlation points for generating a more accurate merge than the rough merge 2500, or for modifying the rough merge 2500 prior to generating the more accurate merge. A select points option 2505 is shown on the user interface. While the select points option 2505 is shown to be represented on the user interface as a button, the select points option 2505 may be implemented in other ways via the user interface. Upon the select points option 2505 being selected by the user, the user may be prompted to select correlation points between the two models 2400, 2402 for refining the merged model, as described in greater detail below.

Following the merge model option 2404 being initiated (e.g., by the user or by the model manager 2102), various corresponding points for the first and second models 2400, 2402 are selected for aligning the models 2400, 2402. The user interface shown in FIG. 26 depicts the occlusal surface 2600, 2602 of the first and second models 2400, 2402, respectively, for selecting correlation points 2604 in the two models 2400, 2402. The correlation points 2604 include a left point, an apex point, and a right point for each model 2400, 2402. The left correlation point 2604 on the first model 2400 may be a point on the left side of the first model 2400 which correlates or corresponds to a correlation point 2604 on the left side of the second model 2402. Similarly, the apex correlation point may be a point towards the center of the first model 2400 which correlates to a correlation point 2604 towards the center of the second model 2402, and the right correlation point 2604 on the first model 2400 may be a point on the right side of the first model 2400 that correlates to a correlation point 2604 on the right side of the second model 2402. In some embodiments, a user selects the correlation points 2604, for instance, by locating a geometric feature on the first model 2400, selecting that geometric feature on the first model 2400, and locating and selecting a similar, related, or corresponding geometric feature on the second model 2402. In some embodiments, the merge manager 2108 selects the correlation points 2604 (e.g., based on correlating geometric features in the respective models 2400, 2402). In each embodiment, a user may modify the location of the correlation points 2604 based on the prominence of geometric features in the first and second models 2400, 2402 to better align the first and second models 2400, 2402. The user may select the correlation points 2604 and drag the selected correlation points 2604 to different locations as needed.

Once the correlation points 2604 on the first model 2400 and second model 2402 are selected, the first and second models 2400, 2402 are merged. The merge manager 2108 is configured to merge the first model 2400 and second model 2402.

Figure 27:
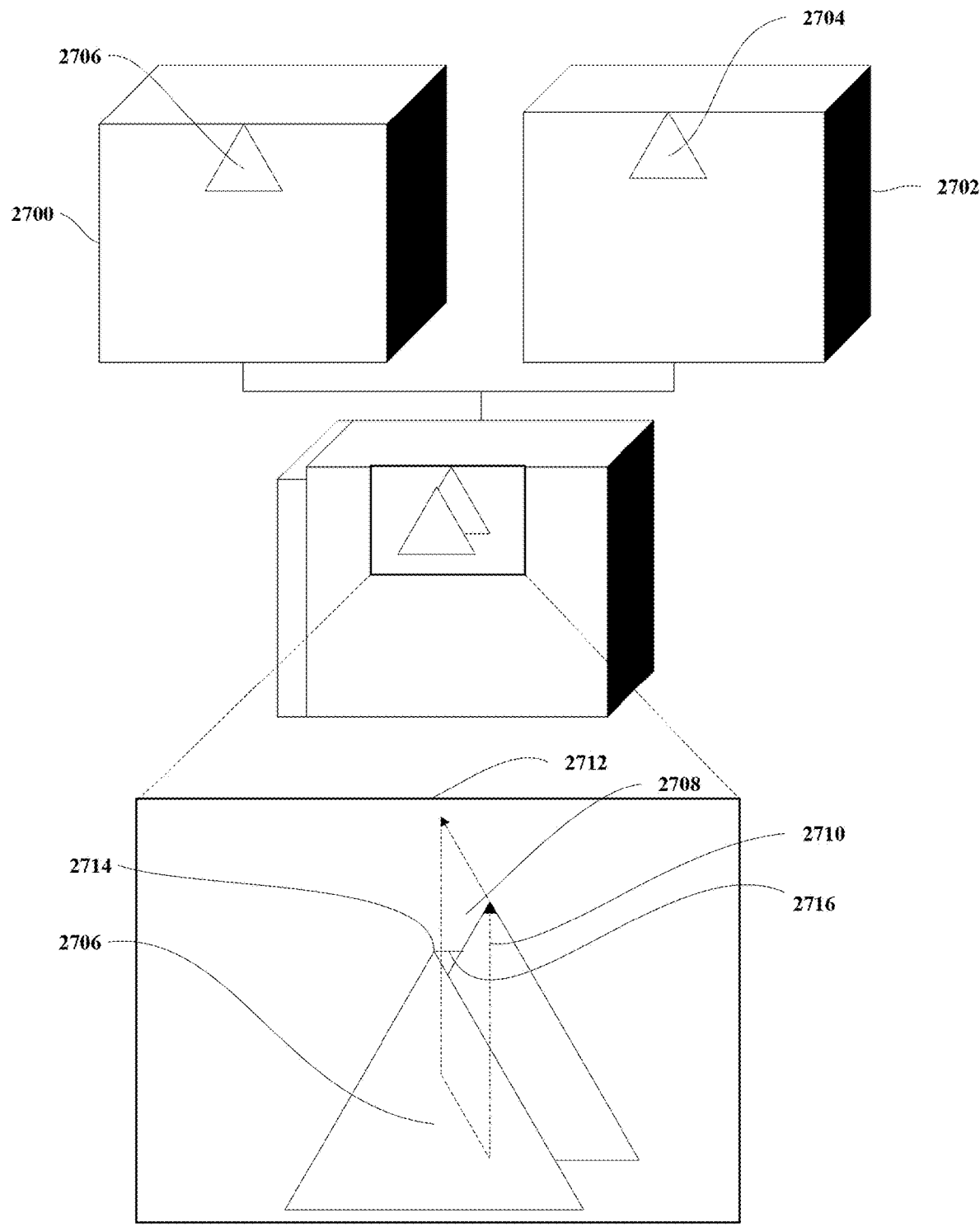
FIG. 27 is a simplified representation of two three-dimensional models being merged, according to an illustrative embodiment.

Referring now to FIG. 27, in some embodiments, the merge manager 2108 is configured to align the occlusal surface 2600 of the first model 2400 with the occlusal surface 2602 of the second model 2402. Specifically, FIG. 27 shows simplified first and second models 2700, 2702 which are merged to form a merged model 2800 (of FIG. 28). In some embodiments, the merge manager 2108 overlays the correlation points 2604 for the first model 2400 and the correlation points 2604 for the second model 2402 to align the first model 2400 and second model 2400. As the merge manager overlays the correlation points 2604 for the first model 2400 and the correlation points 2604 for the second model 2402, each of the geometric faces for the first model 2400 are overlaid on the second model 2402. As such, the first model 2400 is stacked on top of and aligned with the second model 2402. Where the models 2400, 2402 are the same, each of the geometric faces on the first and second models may be aligned with corresponding geometric faces and extend within the same plane. Where the models 2400, 2402 deviate from one another, at least some of the geometric faces may not be aligned, or may not extend within the same plane. Hence, some geometric faces in the first model 2400 may be offset from corresponding geometric faces in the second model 2402. The merge manager 2108 is configured to apply various best fit calculations, which compare the anatomy of the scanned teeth, to more finely align the first and second models 2400, 2402.

As shown in FIG. 27, and in some embodiments, the merge manager 2108 is configured to determine whether a geometric face 2704 of the second model 2702 has a depth greater than a geometric face 2706 of the first model 2700. As can be seen in FIG. 27, the first model 2700 has different dimensions from the dimensions of the second model 2702. As such, the geometric faces 2704, 2706 are not aligned and does not extend within the same plane.

The merge manager 2108 is configured to selectively remove geometric faces from the first and/or second model. The merge manager 2108 is configured to selectively remove geometric faces from the first and/or second model based on relative depth of the geometric faces. In some embodiments, the merge manager 2108 identifies corresponding geometric faces for the first and second models 2400, 2402. For instance, when the first model 2400 is stacked atop and aligned with the second model 2402, the merge manager 2108 may identify the nearest geometric faces for the first and second models 2400, 2402. Where the models 2400, 2402 are the same, for a given geometric face for the first model 2400, the nearest geometric face on the second model 2402 is aligned and extends in the same plane. At locations where the first and second models 2400, 2402 are not the same, corresponding geometric faces for the first model 2400 and second model 2402 will be slightly offset from one another.

The merge manager 2108 may be configured to identify, for a given geometric face of the first model 2400, a corresponding geometric face on the second model 2402 which is nearest to the geometric face of the first model 2400. The merge manager 2108 may be configured to identify the nearest face on the second model 2402 for each geometric face on the first model 2400.

As shown in FIG. 27, the geometric face 2706 for the first model 2700 and the geometric face 2704 for the second model 2702 are offset. The merge manager 2108 may quantify the offset for the geometric faces 2704, 2706 for determining whether one of the first and second geometric faces 2704, 2706 have a greater depth. The merge manager 2108 is shown in FIG. 27 to define a plane 2708 on the second model 2702. In some embodiments, the merger manager 2108 defines a plane 2708 within or corresponding to the geometric face 2704 nearest to the geometric face 2706 on the first model 2700. The merge manager 2108 may identify a vertex 2710 for the geometric face 2704. The vertex 2710 may be the peak (or maximum elevation) of the geometric face 2704. The merge manager 2108 may define the plane 2708 based on the vertex 2710. In some embodiments, the merge manager 2108 defines the plane 2708 based on the identified vertex 2710 and a normal vector 2712 (e.g., a perpendicularly extending vector with respect to the vertex 2710) for the vertex 2710. Hence, the plane 2708 in these embodiments extends perpendicularly from the geometric face 2704 and is aligned with the vertex 2710.

In some embodiments, the merge manager 2108 is configured to identify a vertex 2714 for the geometric face 2706 of the first model 2700 (e.g., the geometric face 2706 nearest to the geometric face 2704). Similar to the vertex 2710 of the second model 2702, the vertex 2714 of the first model 2700 may be the peak (or maximum elevation) of the geometric face 2706.

The merge manager 2108 is configured to determine a distance 2716 between the vertex 2714 and the plane 2708. The distance 2716 may correspond to the offset between the geometric faces 2704, 2706. In some embodiments, the distance includes X, Y, and Z components (e.g., height, width, and depth). The merge manager 2108 may be used for determining relative depth of the first and second models 2400, 2402. In some embodiments, the merge manager 2108 compares the distance 2716 between the vertex 2714 and plane 2708 to a threshold. The threshold may correspond to a relative depth between the geometric faces 2704, 2706 corresponding to one another. In some embodiments, the threshold is a minimum distance. The distance 2716 may satisfy the threshold when the distance 2716 exceeds the minimum distance. In other embodiments, the threshold is between a minimum and maximum distance. Thus, the distance 2716 may satisfy the threshold when the distance 2716 falls between the minimum and maximum distance of the threshold.

The merge manager 2108 is configured to remove geometric faces on a given model where a corresponding geometric face on the other model has a greater depth. For instance, the merge manager 2108 may remove the geometric face 2706 on the first model 2700 where the geometric face 2704 on the second model 2702 has a greater depth (e.g., with respect to the geometric face 2706). In some embodiments, where the distance 2716 satisfies the threshold, the merge manager 2108 may remove the geometric face 2706 on the first model 2700.

In some embodiments, the merge manager 2108 is configured to identify the relative depth by casting a ray from each face on the first model 2400 to nearby faces on the second model 2402. The merge manager 2108 may cast a ray for each geometric face in the first model 2400 to nearby faces on the second model 2402. The merge manager 2108 may define a reverse face normal plane or vector (e.g., a plane extending beneath and perpendicular) for a geometric face on the first model 2400. The merge manager 2108 may cast the ray from the reverse face normal plane or vector towards the nearby geometric faces in the second model 2402. The merge manager 2108 may determine whether any geometric faces on the second model 2402 intersect with the ray (within a tolerance or threshold, for instance). Where a face on the second model 2402 intersects with the ray, the merge manager 2108 removes the geometric face on the second model 2402.

The merge manager 2108 may be configured to identify, determine, and/or quantify a depth between relative geometric faces for each of the geometric faces of the first model 2400. Hence, the merge manager 2108 may evaluate each of the geometric faces of the first model 2400, and at least some of those geometric faces may be removed. In some embodiments, the merge manager 2108 may be configured to re-execute the steps outlined above with the first and second models 2400, 2402 reversed (e.g., where the second model 2402 is stacked atop and aligned with the first model 2400). The merge manager 2108 identifies nearest geometric faces on the first model 2400 for a given geometric face on the second model 2402, defines a plane for the first model, and identifies a distance between the plane and a vertex of the geometric face on the second model.

In some embodiments, the merge manager 2108 identifies geometric face(s) which are isolated in a geometric model 2400, 2402 (e.g., a given geometric face is surrounded by voids where geometric faces were removed). The merge manager 2108 may delete isolated geometric face(s).

Following such processing of the geometric models, the merge manager 2108 is configured to select a geometry. The selected geometry may be or include a selection of the first or second models 2400, 2402. The selected geometry may include the geometric faces remaining after removal of some of the geometric faces based on corresponding depth. The merge manager 2108 may select a geometry from the first and second models 2400, 2402 based on remaining surface area, number of geometric faces remaining in each model 2400, 2402, etc. The selected geometry may be used for forming the merged model. In some embodiments, the merge manager 2108 incorporates, or combines, geometric faces from the unselected geometry into the selected geometry (e.g., to fill gaps or voids within the selected geometry). The merge manager 2108 may process the selected geometry to fill the gaps or voids. In some embodiments, the merge manager 2108 applies a smoothing function to the merged model. The merge manager 2108 may be further configured to clean or smooth the merged model to generate a closed surface, for example, by performing Poisson surface reconstruction or by performing a gap closing or smoothing algorithm.

Figure 28:
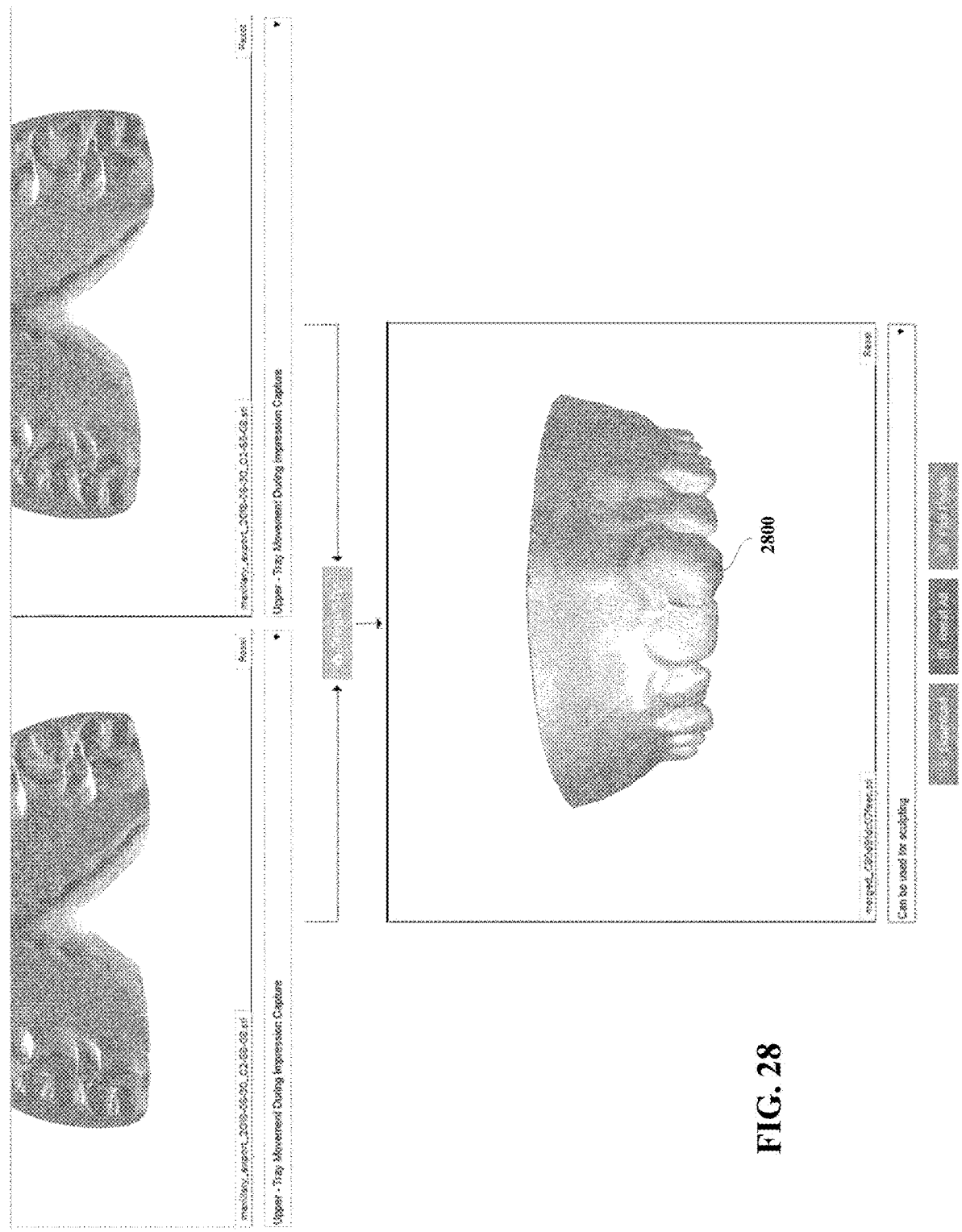
FIG. 28 is a user interface depicting the merged model generated from the first and second models, according to an illustrative embodiment.

The merge manager 2108 may be configured to render the merged model to a user, such as a dental technician, via a user interface. FIG. 28 shows a user interface depicting the merged model 2800 generated from the first and second models 2400, 2402. In some embodiments, the merge manager 2108 merges the first and second models 2400, 2402 according to a number of different merge strategies. The merge manager 2108 may merge the first and second models 2400, 2402 according to merge strategies that address shifted scans, improper dental impression material mixtures, etc. The merge manager 2108 may be configured to automatically select the best merging strategy using, for instance, artificial intelligence, machine learning, neural networks, etc. The merge manager 2108 may, for instance, train a neural network for identifying which merging strategies result in the best merged model.

In some embodiments, the merge manager 2108 is configured to display each of the merged models 2800 to a user, such as a technician, on a display or the user interface as shown in FIG. 28. In some embodiments, the user interface includes an image of the patient's smile (e.g., corresponding to the dental impression). The image may be displayed side-by-side with the merged model (and, optionally, the first and second models 2400, 2402). The technician may select the ideal merged model based on the side-by-side photo. Following selection of the merged model for use, the technician may manipulate, modify, etc. the merged model to reposition the patient's teeth, and the technician may export the modified merged model to the manufacturing manager 2114 for manufacturing dental aligners for repositioning the patient's teeth, as described above.

Figure 29:
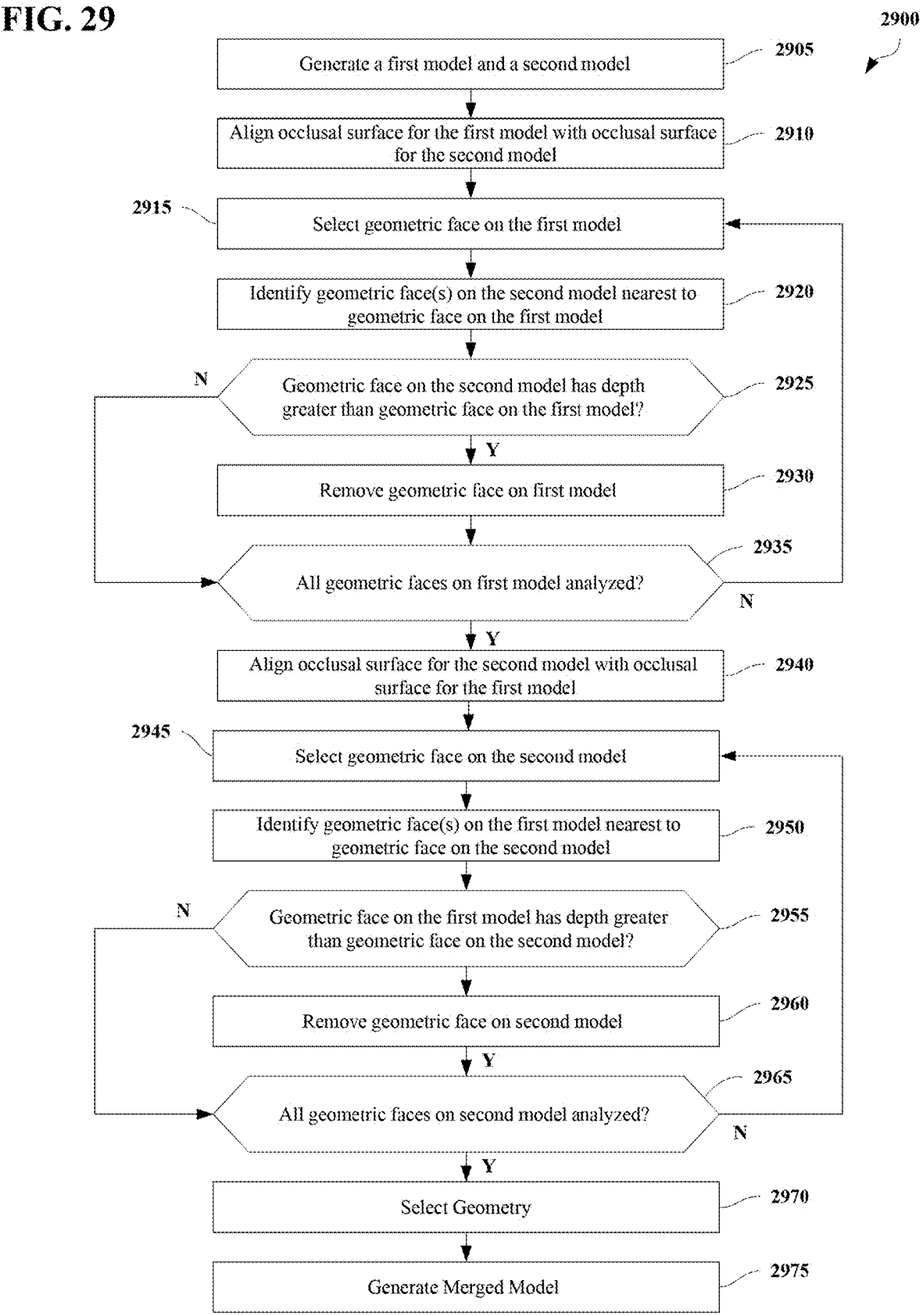
FIG. 29 is a flow diagram of at least one embodiment of another method of merging three-dimensional models that may be executed by the computing device of FIGS. 20 and 21, according to an illustrative embodiment.

Referring to FIG. 29, a flowchart depicting one embodiment of a method 2900 for dental impression scan merging is shown, according to an exemplary embodiment. Similar to FIG. 22, it should be appreciated that, in some embodiments, the operations of the method 2900 may be performed by one or more components of the environment 2100 of the computing device 2000 shown in FIG. 21.

At step 2905, the computing device 2000 generates a first model and second model. In some embodiments, the computing device 2000 scans one or more dental impressions received from a customer to generate three-dimensional models 2104. Hence, the first model may be a three-dimensional model including a plurality of geometric faces indicative of a first dental impression of a user's dental arch, and the second model may be a three-dimensional model including a plurality of geometric faces indicative of a second dental impression of the user's dental arch (e.g., the same dental arch). The computing device 2000 may use any stereoscopic imager, photometric scanner, laser scanner, infrared scanner, structured light sensor, or other three-dimensional scanning technology to scan the dental impressions. Each model 2104 may be embodied as a three-dimensional representation of the geometry of a dental impression, which is in turn a negative representation of a dental arch (e.g., a mandibular arch or maxillary arch) of the customer. Illustratively, the models 2104 are embodied as STL files that describe the surface geometry of the corresponding dental impressions and include geometric faces which form a mesh which defines the surface geometry or contours. In other embodiments, the models 2104 may be embodied as any surface or solid three-dimensional modeling data.

At step 2910, and in some embodiments, the computing device 2000 aligns an occlusal surface 2600 of the first model 2400 with an occlusal surface 2602 of the second model 2402. In some embodiments, the computing device 2000 analyzes geometric properties of the first and second models 2400, 2402 for aligning the occlusal surfaces 2600, 2602. In some embodiments, the computing device 2000 receives or automatically selects correlation points 2604 on the first and second models 2400, 2402. The computing device 2000 may overlay the correlation points 2604 and remaining portions of the first and second models 2400, 2402. The computing device 2000 may align the occlusal surfaces 2600, 2602 such that at least some of the geometric faces in the first and second models 2400, 2402 are aligned and extend in the same plane. Where the first and second models 2400, 2402 are different from one another, the geometric faces may be offset from one another. For instance, some geometric faces on one model may correspond to greater measured or captured depths than in the other model.

At step 2915, and in some embodiments, the computing device 2000 selects a geometric face on the first model 2400. The computing device 2000 may progressively select geometric faces on the first model 2400 beginning in one area (e.g., the right side, the center or apex, etc.), and progress through the geometric faces in the first model 2400, as described in greater detail below.

At step 2920, and in some embodiments, the computing device 2000 identifies a geometric face on the second model 2402 nearest to the geometric face selected at step 2915. In embodiments where the first and second models 2400, 2402 are the same, the nearest geometric face on the second model 2402 is directly aligned with and extends planar to the geometric face selected at step 2915. In embodiments where the models 2400, 2402 are not the same, the identified geometric face on the second model 2402 nearest to the geometric face selected at step 2915 may be slightly offset from one another.

At step 2925, and in some embodiments, the computing device 2000 may determine whether the geometric face on the second model 2402 has a depth greater than the geometric face on the first model 2400. In some embodiments, the computing device 2000 may define a plane on the second model 2400. Specifically, the computing device 2000 defines a plane on the geometric face on the second model 2400. The plane may extend along the vertex for the geometric face and a normal vector for the vertex. Hence, the plane may extend outwardly from (e.g., perpendicularly to) and along the vertex of the geometric face. The computing device 2000 may determine a distance between the vertex of the geometric face on the first model 2400 and the plane. The computing device 2000 may compare the distance to a threshold (e.g., a minimum distance, a range of distances, etc.). In some embodiments, the merge manager 2108 identifies the relative depth by casting a ray from the geometric face on the first model 2400 to the geometric face on the second model 2402. The computing device 2000 may define a reverse face normal plane or vector (e.g., a plane extending beneath and perpendicular) from the geometric face on the first model 2400. The computing device 2000 may cast a ray from the reverse face normal plane or vector to the geometric face on the second model 2402. The merge manager 2108 may determine whether the geometric face on the second model 2402 intersects with the ray (e.g., within a tolerance or threshold, for instance). Where the geometric face on the second model 2402 intersects with the ray, the computing device 2000 may determine that the geometric face on the second model 2402 has a greater depth.

Where the computing device 2000 determines that the geometric face on the second model 2402 has a depth greater than the geometric face on the first model 2400, the method 2900 proceeds to step 2930. Where the computing device 2000 determines that the geometric face on the second model 2402 does not have a depth greater than the geometric face on the first model 2400 (or the distance or depth do not satisfy a threshold), the method 2900 proceeds to step 2935.

At step 2930, and in some embodiments, the computing device 2000 removes the geometric face on the first model 2400. The computing device 2000 may remove the geometric face on the first model 2400 when the corresponding geometric face on the second model 2402 has a greater depth. The computing device 2000 may remove the geometric face on the first model 2400 when the distance between the plane on the second model 2402 and the vertex of the first model 2400 satisfies a threshold (e.g., the vertex is greater than a minimum distance, falls within a range of distances, etc.) corresponding to relative depth. The computing device 2000 may remove the geometric face on the first model 2400 when the ray cast from a reverse face plane or vector intersects with the geometric face on the second model 2402.

At step 2935, the computing device 2000 may determine whether all geometric faces on the first model 2400 have been analyzed. The computing device 2000 may maintain a data log of each geometric face as the relative depth between the geometric face of the first and second models 2400, 2402 are determined. Where the computing device 2000 determines that all geometric faces on the first model 2400 have been analyzed, the method 2900 may proceed to step 2940. Where geometric faces have not been analyzed, the method 2900 may proceed back to step 2915, e.g., where the computing device 2000 selects another geometric face of the first model 2400. Hence, the method may loop between step 2915-2935 until all geometric faces of the first model 2400 are analyzed.

At step 2940, the computing device 2000 aligns the occlusal surface 2602 of the second model 2402 with the occlusal surface 2600 of the first model 2400. Following alignment, the second model and first model 2400, 2402 are reversed (e.g., with respect to the orientation at step 2910). In this regard, the first and second models 2400, 2402 are flipped. The first and second models 2400, 2402 are aligned, except that the second model 2402 is on top of the first model 2400 at step 2940. Following step 2940, the method 2900 may proceed to steps 2945-2965, which are similar to steps 2915-2935 described above.

Following analysis of each of the geometric faces on the second model (e.g., step 2965), the method 2900 proceeds to step 2970. At step 2970, the computing device 2000 selects a geometry. The selected geometry may be or include a selection of the first or second models 2400, 2402. The selected geometry may include the geometric faces remaining after removal of some of the geometric faces based on corresponding depth. The computing device 2000 may select a geometry from the first and second models 2400, 2402 based on remaining surface area, number of geometric faces remaining in each model 2400, 2402, etc. The selected geometry may be used for forming the merged model.

At step 2975, and in some embodiments, the computing device 2000 generates the merged model. The computing device 2000 may combine remaining geometric faces from the first and/or second model 2400, 2402 into the selected geometry. In some embodiments, the computing device 2000 incorporates, or combines, geometric faces from the unselected geometry into the selected geometry (e.g., to fill gaps or voids within the selected geometry). The computing device 2000 may process the selected geometry to fill the gaps or voids. In some embodiments, the computing device 2000 applies a smoothing function to the merged model. The computing device 2000 may be further configured to clean or smooth the merged model to generate a closed surface, for example, by performing Poisson surface reconstruction or by performing a gap closing or smoothing algorithm.

Figure 30:
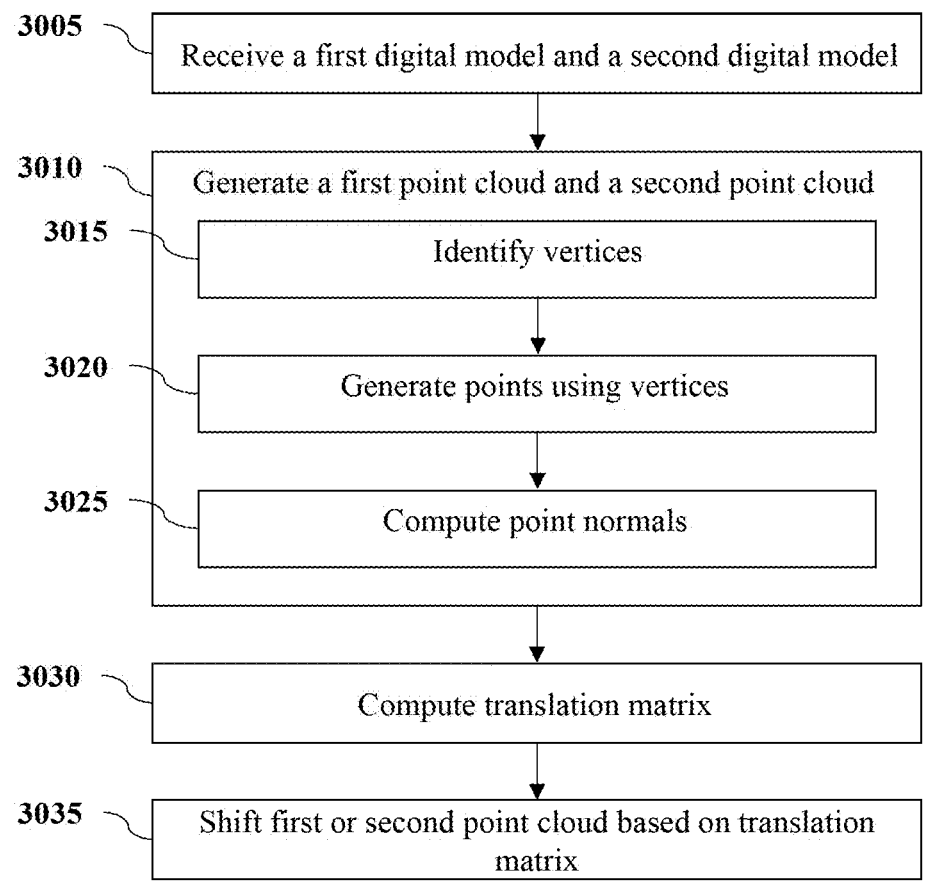
FIG. 30 is a flow diagram of at least one embodiment of a method of aligning two or more dental models that may be executed by the computing device of FIGS. 20 and 21, according to an illustrative embodiment.

Referring now to FIG. 30, a flowchart depicting one embodiment of a method 3000 for aligning two or more dental models is shown, according to an exemplary embodiment. Similar to FIG. 22, it should be appreciated that, in some embodiments, the operations of the method 3000 may be performed by one or more components of the environment 2100 of the computing device 2000 shown in FIG. 2. For instance, the steps depicted in method 3000 may be performed by the computing device 2000.

At step 3005, the computing device 2000 receives a first digital model and a second digital model. In some implementations, the first digital model and second digital model are generated based on a scan of two or more physical dental models of the same dental arch of a user, dental impressions of the same dental arch of a user, two or more scans of the same dental arch of a user, etc. Hence, the first digital model and second digital model are digital models of a common dental arch of a user (e.g., an upper arch or a lower arch of the same user). The computing device 2000 may receive the first digital model and second digital model from a three-dimensional (3D) scanner. The digital models may be similar to the models described above with reference to FIG. 22. The computing device 2000 may receive the digital models from any form or type of 3D scanner including, for instance a stereoscopic imager, photometric scanner, laser scanner, infrared scanner, structured light sensor, or other three-dimensional scanning technology configured to scan the dental impressions. Each model may be embodied as a three-dimensional representation of the geometry of a dental impression, which is in turn a negative representation of a dental arch (e.g., a mandibular arch or maxillary arch) of the user. Illustratively, the models are embodied as standard triangle language (STL) files that describe the surface geometry of the corresponding dental impressions. The STL files include a plurality of interconnected triangles having three vertices coupled to other triangles which, together, define, characterize, or otherwise describe the surface geometry of the customer's dental arch.

At step 3010, the computing device 2000 generates a first point cloud and a second point cloud. In some implementations, the model manager 2102 of the computing device 2000 generates the first point cloud and the second point cloud. The model manager 2102 generates a first point cloud for the first digital model, and a second point cloud for the second digital model. Each point cloud may include a plurality of points in a three-dimensional space which represent an outermost point on the surface of the user's dentition. The points of the point cloud may include a respective point normal. Each point normal includes a vector extending outwardly from the points of the point cloud. For each point, the vectors can be perpendicular to the surface of the digital model at the point. Each of the points and point normals for the point clouds may together define, characterize or otherwise describe the surface geometry of the customer's dental arch. The model manager 2102 computes, determines, or otherwise generates the point clouds according to steps 3015-3025 described below. In some implementations, the model manager 2102 may use, implement, or otherwise access one or more external systems, devices, or libraries, such as a TriMesh library, for determining, identifying, or otherwise generating one or more aspects of the point clouds.

At step 3015, the computing device 2000 identifies each of the vertices of the geometric faces. In some implementations, the model manager 2102 identifies vertices which connect two or more geometric faces. Where each of the geometric faces are triangles, the vertices are defined as the point in which two edges of the triangles meet. The model manager 2102 parses each of the STL files for the first and second digital models to identify the vertices for each digital model. The model manager 2102 may identify each geometric face, and correspondingly determine the vertices for those geometric faces. The model manager 2102 may identify coordinates for each of the identified vertices (e.g., within the 3D space in which the digital models are generated). The model manager 2102 may remove duplicate coordinates (e.g., vertices for adjacent geometric faces which share a common vertex).

At step 3020, the computing device 2000 generates points using the vertices (e.g., identified at step 3015). In some implementations, the model manager 2102 generates the points using each of the vertices of the geometric faces of the first and second models. The model manager 2102 generates points for the point clouds which represent the respective model (e.g., a first set of points for the first point cloud representing the first digital model, a second set of points for a second point cloud which represents the second digital model, etc.). The model manager 2102 may generate the points using the coordinates of the vertices of the geometric faces of the first and second models. In the 3D space, each point may be located on a vertex for a geometric face of the digital model that corresponds to the STL file.

In some implementations, the model manager 2102 may generate the points using a subset of the coordinates of the vertices. In this regard, the model manager 2102 may be configured to down-sample the vertices to down-sample the points of the point clouds. The model manager 2102 may be configured to down-sample the points of the point clouds in particular regions or portions of the digital models. For instance, the model manager 2102 may be configured to down-sample the points of the point cloud in some portions of the digital model (e.g., the gingiva portion of the digital model corresponding to gingiva on the user's dental arch), and maintain points of the point cloud in other portions of the digital model (e.g., the teeth portion of the digital model corresponding to teeth on the user's dental arch). The model manager 2102 may down-sample the points of the point cloud temporarily (e.g., for purposes of alignment) while adding those down-sampled points back into the digital model or into the merged model or aligned models, or remove at least some of the points of the point cloud (e.g., to decrease computing requirements, and increase computing performance and the speed at which models can be merged). In some embodiments, the model manager 2102 can down-sample or eliminate unnecessary points from a digital model or the merged model based on the unnecessary points being located on a part of the model that is irrelevant or less importance than other parts of the model to manufacturing aligners. For example, the model manager 2102 can down-sample or eliminate points located a threshold distance from a gingival-tooth interface of the model (e.g., greater than 3 mm, greater than 5 mm, greater than 1 cm). By down-sampling or eliminating points that are irrelevant or less important than other parts of the model to manufacturing aligners, the model manager 2102 can more quickly perform merges and other functions with respect to the models.

At step 3025, the computing device 2000 computes point normals. In some implementations, the model manager 2102 generates the point normals for each of the generated points for the point clouds (e.g., generated at step 3020). Together, the generated points (e.g., at step 3020) and point normals (e.g., computed at step 3025) represent, form, or otherwise define the point cloud. As stated above, each point normal includes a vector extending outwardly from the points of the point cloud. The vector may extend outwardly from the points of the point cloud orthogonally from the surface of the digital model. Each point of the point cloud may include a corresponding point normal.

In some implementations, the point normals are surface normals. The surface normals may be or include a vector which extends orthogonally from a geometric face corresponding to a point of the point cloud. Each point may correspond to a vertex for a geometric face. The geometric face extends along a plane. The model manager 2102 is configured to compute the surface normal for the plane along which the geometric face extends. The model manager 2102 is configured to apply, use, or define the point normal for the points corresponding to the vertices of a given geometric face as the computed normal for the plane corresponding to the geometric face.

In some implementations, the point normals are vertex normals. The vertex normals may be or include a vector which extends perpendicular to two vectors. The two vectors may be two adjacent edges of the geometric face (e.g., which connect to form a vertex). In other words, a vertex normal for a vertex of a geometric face is defined as a vector extending perpendicular to the two edges which form the vertex of the geometric face. The model manager 2102 is configured to compute the vertex normal for each of the points. The model manager 2102 may compute the vertex normal by identifying the edges of each geometric face which form the vertex. The model manager 2102 may compute the vertex normal by computing a cross-product of the edges which form the vertex.

At step 3030, the computing device 2000 computes a translation matrix. In some implementations, the model manager 2102 computes the translation matrix using the first point cloud and the second point cloud (e.g., generated at step 3010). The translation matrix may be a matrix comprising a shift of each of the points of one of the point clouds to align the first point cloud and second point cloud. The translation matrix may be a shift of the first point cloud relative to the second point cloud (or vice versa). In some implementations, the translation matrix may be computed using algorithms which implement a combination of rough (or global) alignment and fine (or local) alignment. As one example, the model manager 2102 may compute the translation matrix using RANdom Sample Consensus (RANSAC) for global alignment of the first and second point cloud, and Iterative Closest Point (ICP) for local alignment. In some implementations, the model manager 2102 first computes the translation matrix using RANSAC then refines, modifies, or otherwise adjusts the translation matrix using ICP.

At step 3035, the computing device 2000 shifts the first or the second point cloud based on the translation matrix (e.g., computed at step 3030). In some implementations, the model manager 2102 shifts the points of the first or second point cloud by the shifts specified in the translation matrix to align the first and second point cloud. Each point may be shifted according to the translation matrix. The model manager 2102 shifts the points of the first or second point cloud to minimize the distance between two corresponding points of the point clouds. In some implementations, the model manager 2102 may iteratively perform steps 3030 and 3035 (e.g., computation of the translation matrix and shifting the first or second point cloud). The model manager 2102 may iteratively perform steps 3030 and 3035 to minimize the distance between the points so as to more closely align the first and second point clouds. As the first point cloud and second point cloud are generated based on separate digital models, the first and second point clouds may not necessarily be perfectly aligned. However, the model manager 2102 may iteratively perform steps 3030 and 3035 so as to align the first and second model without regard to differences between the first and second model (e.g., to best align the first and second model).

The model manager 2102 may iteratively perform steps 3030 and 3035 to best align the first and second point cloud. The model manager 2102 may perform steps 3030 and 3035 a predetermined number iterations. The predetermined number may be selected automatically based on an average number of iterations for the point clouds being sufficiently aligned according to one or more metrics, such as a Root Mean Square (RMS) error. For instance, the predetermined number may be 1 iteration, 2 iterations, 5 iterations, 10 iterations, 20 iterations, 100 iterations, etc. The predetermined number may be selected by a user, such as an operator or IT manager of the computing device 2000 based on a balance between computing requirements and accuracy. In some implementations, the model manager 2102 performs steps 3030 and 3035 until the RMS error for corresponding points of the point cloud satisfies a threshold (e.g., an RMS error of 0.5 mm, 0.55 mm, 0.6 mm, 0.65 mm, 0.7 mm, 0.75 mm, 0.8 mm, 0.85 mm, 0.9 mm, 0.95 mm, etc.). The model manager 2102 may shift the points of the point cloud(s), and compute an RMS error for corresponding points of the point clouds. The model manager 2102 may compute the RMS error for each of the points, a subset of the points, etc.

Once the model manager 2102 aligns the first and second point cloud, the computing device 2000 generates a merged model (e.g., a model which includes at least some portions of the first and second point cloud). In some implementations, prior to generating the merged model, the computing device 2000 may convert the aligned point clouds into STL files. The computing device 2000 may use the aligned point clouds or aligned STL files for generating the merged model. The computing device may generate the merged model as described in greater detail above (e.g., starting at step 2308 of FIG. 23, for instance).

Through automating alignment of the models, the systems and methods described herein provide numerous advantages and improvements over other systems and methods for merging models. For example, by generating point clouds and automatically aligning those point clouds to generate a merged model, the aligned point clouds, and thus the models, are more accurately aligned than could otherwise be achieved if relying on user inputs, which require a user to manually select common points on the models to be merged. Manually selecting common points on different models for alignment is not as accurate the automatic alignment of point clouds disclosed herein, as manual inputs are prone to human error and other inaccuracies. Automated alignment of the point clouds, and thus the models, also eliminates delays caused by waiting for manual inputs, which improves upon prior systems and method by increasing the speed at which models can be merged, thereby also decreasing the overall time needed to prepare dental models for manufacturing dental aligners. Through improving the accuracy of the alignment of the models, the merged model generated by the systems and methods described herein are a more accurate representation of a user's dentition as compared to merged models that rely on a user selection of common points of the models to be merged. Using a more accurate merged model to manufacture dental aligners results in creating dental aligners that better fit a user's dentition, thereby resulting in dental aligners that are more comfortable to wear and that result in more accurate treatment outcomes. By increasing the accuracy of treatment outcomes, the need to retreat a user is reduced or eliminated.

Figure 31:
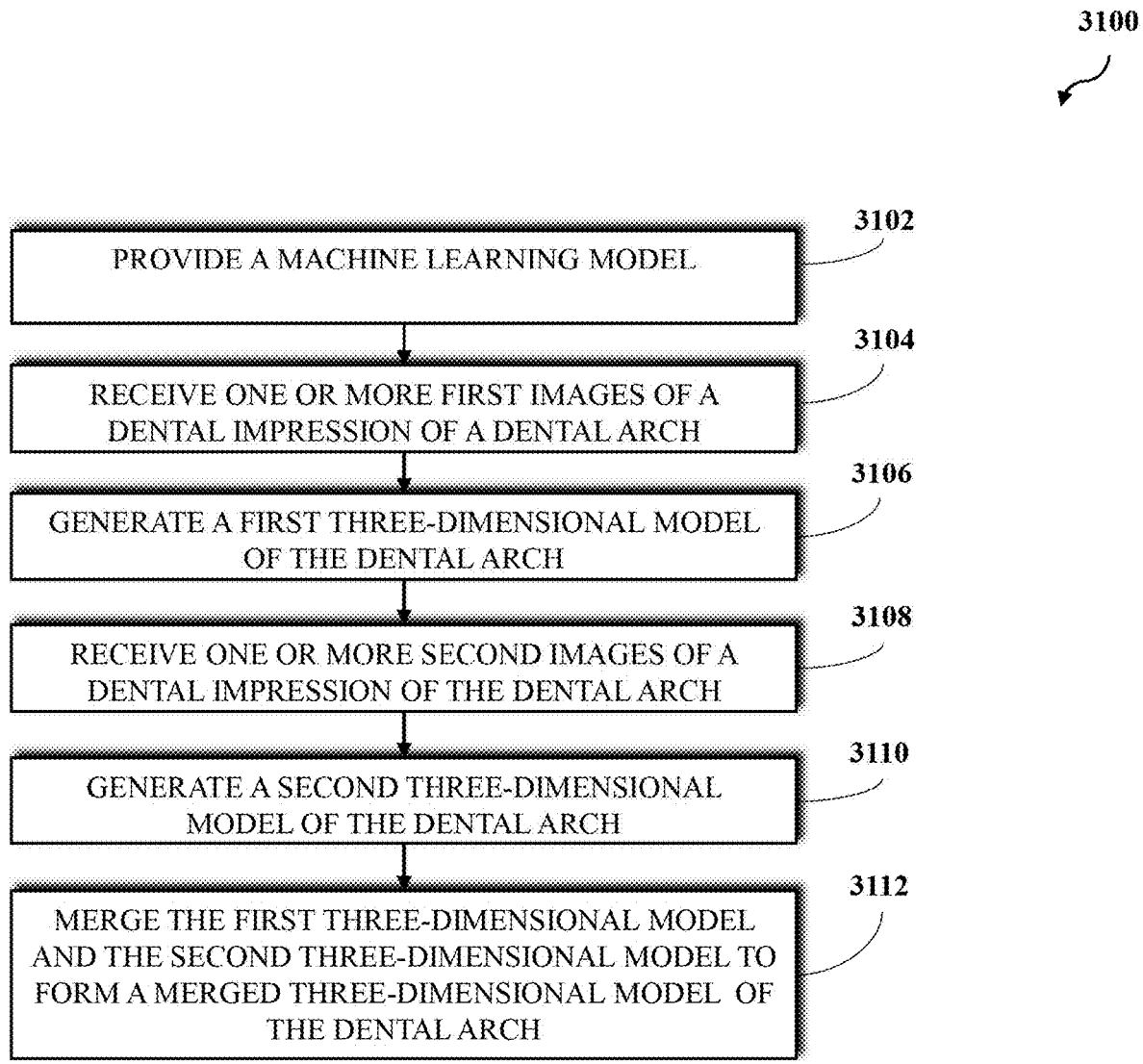
FIG. 31 is a flow diagram of at least one embodiment of a method of generating a 3D model from one or more images of a dental impression, according to an illustrative embodiment.

Referring now to FIG. 31, depicted is a flowchart of method 3100 of generating a 3D model from 2D images of dental impressions, according to an illustrative embodiment. The method 3100 may be implemented, performed, or otherwise executed by the components described above with respect to FIG. 1-FIG. 30. As a brief overview, at step 3102, a model training system (such as model training system 902) may provide a machine learning model. At step 3104, a model generation system (such as model generation system 102, or model generation system 924) may receive one or more first images of a dental impression of a dental arch. At step 3106, the model generation system may generate a first three-dimensional (3D) model of the dental arch. At step 3108, the model generation system may receive one or more second images of a dental impression of the dental arch. At step 3110, the model generation system may generate a second 3D model of the dental arch. At step 3112, a model merging system (such as model merging system 104) merges the first 3D model (e.g., generated at step 3106) and the second 3D model (e.g., generated at step 3110) to form a merged 3D model of the dental arch.

At step 3102, a model training system (such as model training system 902) may provide a machine learning model. In some embodiments, the model training system 902 may provide a machine learning model 922 using one or more training images 904 of a dental impression of a respective dental arch and a three-dimensional (3D) training model 906 of the respective dental arch. For example, the model training system 902 may receive a plurality of data packets 914 of a training set 912. The data packets 914 may include data corresponding to training images 904 of a dental impression of a respective dental arch and a 3D training model 906 of the respective dental arch. The model training system 902 may identify a plurality of correlation points 916 for each data packet 914 of the plurality of data packets 914 of the training set 912. The correlation points may be between the one or more training images 904 and the 3D training model 906 of the respective dental arch. The model training system 902 may generate the machine learning model 922 using the one or more training images 904, the 3D training model 906, and the plurality of correlation points 916 between the one or more training images 904 and the 3D training model 906 for each data packet 914 of the plurality of data packets 914 of the training set 912. Various details of the model training system 902 are described above with reference to FIG. 2-FIG. 19.

At step 3104, a model generation system (such as model generation system 102, or model generation system 924) may receive one or more first images 106 of a dental impression of a dental arch. In some embodiments, the model generation system 102, 924 receives one or more first images 106 of a first dental impression of a dental arch of a user. The model generation system 102, 924 may receive the images 106 from a user device of the user, or from a user device associated with the user. For example, a user may capture the images 106 of the dental impression using their user device, and upload the images 106 to a portal or website corresponding to the model generation system 102, email the images 106 to an email address corresponding to the model generation system 102, etc. In some embodiments, another person (such as a dentist, orthodontist, other dental professional, or a non-dentist/orthodontist/dental professional) may administer the dental impressions to the dental arch of the user, capture the images 106 of the dental impressions, and provide the images 106 to the model generation system 102. In these and other embodiments, the model generation system 102, 924 may receive the images 106 of a first dental impression of a dental arch.

At step 3106, the model generation system 102, 924 may generate a first three-dimensional (3D) model 108 of the dental arch. In some embodiments, the model generation system 102, 924 may generate the first 3D model 108 of the dental arch of the user by applying the one or more first images 106 to the machine learning model 922 (e.g., provided at step 3102). The machine learning model 922 may receive the images 106 as an input. The machine learning model 922 may be trained to generate, e.g., as an output, the 3D model 108 of the dental arch of the user. For example, the machine learning model 922 may be a neural network (such as neural network 500 shown in FIG. 5) which is trained to generate 3D models 108 from 2D images 106 of dental impressions. Various details of the model generation system 102, 924 generating 3D models 108 from 2D images 106 are described above with reference to FIG. 2-FIG. 19.

At step 3108, the model generation system may receive one or more second images 106 of a dental impression of the dental arch. At step 3110, the model generation system may generate a second 3D model of the dental arch. Step 3108 and step 3110 may be similar to step 3104 and step 3106 described above. In some embodiments, the images 106 received at step 3104 and the images received at step 3108 may be of the same dental impression (e.g., the images 106 may be representative of the same dental impression from different perspectives, for instance). In some embodiments, the images 106 received at step 3104 and the images received at step 3108 may be of separate dental impressions of the same dental arch (e.g., the images 106 received at step 3104 may be of a first dental impression of a dental arch and the images 106 received at step 3108 may be of a second dental impression of the same dental arch). In either embodiment, the 3D models 108 generated at step 3106 and at step 3110 are of the same dental arch.

At step 3112, a model merging system (such as model merging system 104) merges the first 3D model 108 (e.g., generated at step 3106) and the second 3D model 108 (e.g., generated at step 3110) to form a merged 3D model 110 of the dental arch. In some embodiments, the model merging system 104 merges the first 3D model 108 and second 3D model by generating a first point cloud of the first 3D model 108 and a second point cloud of the second 3D model 108. The model merging system 104 may align the first point cloud and the second point cloud. The model merging system 104 may merge the first 3D model 108 and the second 3D model to generate the merged model 110 based on the alignment of the first point cloud and the second point cloud. Various details regarding the model merging system 104 are described above with respect to FIG. 20-FIG. 30. For instance, the model merging system 104 may include the components of the environment 2100 shown in FIG. 21.

In some embodiments, the method 3100 further includes manufacturing a dental aligner based on the merged 3D model 110. The dental aligner may be specific to the user and configured to reposition one or more teeth of the user. Manufacturing the dental aligner may be similar in some respects to step 2222 of FIG. 22. As such, dental aligners may be manufactured for a user's dental arch without having to physically receive dental impressions of the user's dental arch, which may expedite treatment and delivery of remote/at-home orthodontic treatment.

In some embodiments, the method 3100 further includes generating, using the merged 3D model 110 of the dental arch of the user, a user interface for rendering at a user device that includes the generated 3D model. For example, the user interface may be similar in some respects to the user interface described above. The user interface may include a visual representation of the merged 3D model 110. The method 3100 may further include transmitting the generated user interface to the user device for rendering to the user. Such embodiments may provide a user interface for quickly reviewing 3D models 110 of a user or patient's teeth, without a need for purchasing 3D scanning equipment. Additionally, such implementations and embodiments may supplement 3D scanning equipment by providing a quick and efficient 3D model of a patient's teeth from an impression.

In some embodiments, the method 3100 further includes tracking, based on the merged 3D model 110 of the dental arch of the user, a progress of repositioning one or more teeth of the user by one or more dental aligners from a first position to a second position by comparing the 3D model representing a current position of the one or more teeth with a treatment planning model representing an expected position of the one or more teeth. Tracking the progress described herein may be similar in some regards to progress-tracking described above with respect to FIG. 2-FIG. 19.

In some embodiments, the system and processes described above can be used to generate a merged intermediate mesh created by merging a first 3D model created from one or more 2D images of a first dental impression of a dental arch of a user and one or more of a second 3D model created from one or more 2D images of a second dental impression of the same dental arch of the user and a third 3D model created from one or more 2D images of the same dental arch of the user. The merged intermediate model can be used to manufacture one or more dental aligners for the user' to being dental aligner treatment. A final merged mesh can then be created of the user's teeth using at least one of the merged intermediate mesh, a treatment plan developed based on the merged intermediate mesh, additional 2D images of the user's teeth, additional 2D images of the first dental impression, additional 2D images of the second dental impression, additional 2D images of additional dental impressions of the same dental arch, a 3D scan of the first dental impression, and a 3D scan of the second dental impression. The final merged mesh can be used to manufacture additional dental aligners for the user to continue and conclude their dental aligner treatment according to a treatment plan. As such, the merged intermediate mesh may be of a lesser quality or less accurate representation of the user's teeth as compared to the final merged mesh, but the quality and accuracy of the intermediate merged mesh is sufficient for the user to at least begin a dental aligner treatment plan. For example, based on 2D images that a user captures of a first dental impression and a second dental impression of the same dental arch (e.g., both captured of the user's upper dental arch), an intermediate mesh is generated and one to six dental aligners are manufactured for the user, with each dental aligner being intended to be worn for a duration of one week. Upon receiving the first dental impression and the second dental impression from the user, the systems and processes described above can be used to conduct 3D scans of the dental impressions to generate new 3D models of the dental impressions, merge the new 3D models to form a final merged mesh, and manufacture twenty or more dental aligners for the user based on the final merged mesh. Using an intermediate merged mesh and a final merged mesh beneficially enables the user to begin dental aligner treatment without delay while additional dental aligners are produced for later stages of the user's treatment plan.

In some embodiments, the system and processes described above can be used to generate a 3D model of a dental impression of a dental arch based on one or more 2D images of the dental impression. For example, the machine learning model generated or otherwise provided by the model training system may be trained to generate 3D models of dental impressions based on 2D images of dental impressions. The machine learning model may be configured to generate 3D models of dental impressions based on 2D images of the dental impressions (e.g., received as an input). The machine learning model may be trained in a manner similar to training described above for generating 3D models of dental arches from 2D images of dental impressions (or 2D images of a mouth of a user). In some embodiments, the model generation system may be configured to generate a 3D model of a dental arch of a user based on the 3D model of a dental impression, which in turn is generated based on 2D image(s) of the dental impression. For example, the model generation system may be configured to generate a 3D model of the dental arch using an inversion operation, a subtraction operation, or other Boolean operation. As such, the systems and methods described herein may be used for generating 3D models of dental arches through an intermediate 3D model of a dental impression, which in turn is generated based on 2D images of the dental impression.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be X, Y, or Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the figures. It should be noted that the orientation of various elements may differ according to other exemplary embodiments, and that such variations are intended to be encompassed by the present disclosure.

The hardware and data processing components used to implement the various processes, operations, illustrative logics, logical blocks, modules, and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, flash memory, hard disk storage) for storing data and/or computer code for completing or facilitating the various processes, layers and circuits described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data, which cause a general-purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the systems and methods shown in the various exemplary embodiments are illustrative only. Additionally, any element disclosed in one embodiment may be incorporated or utilized with any other embodiment disclosed herein.

What is claimed is:

1. A system comprising:
    a model training system configured to:
        receive a plurality of data packets of a training set, each data packet of the plurality of data packets including data corresponding to one or more training images of a dental impression of a respective dental arch and a three-dimensional (3D) training model of the respective dental arch;
        identify, for each data packet of the plurality of data packets of the training set, a plurality of correlation points between the one or more training images and the 3D training model of the respective dental arch; and
        generate a machine learning model using the one or more training images, the 3D training model, and the plurality of correlation points between the one or more training images and the 3D training model of each data packet of the plurality of data packets of the training set; and
    a model generation system configured to:
        receive one or more images of a dental impression of a dental arch of a user; and
        generate a 3D model of the dental arch of the user by applying the one or more images of the dental impression to the machine learning model.

2. The system of claim 1, wherein the one or more images of the dental impression are one or more first images of a first dental impression of the dental arch of the user, wherein the 3D model is a first 3D model, and wherein the model generation system is further configured to:
    receive one or more second images of a second dental impression of the dental arch of the user; and
    generate a second 3D model of the dental arch of the user by applying the one or more second images of the second dental impression to the machine learning model.

3. The system of claim 2, further comprising:
    a model merging system configured to:
        align one or more points corresponding to the first 3D model with one or more points corresponding to the second 3D model; and
        merge the first 3D model and the second 3D model to generate a merged model, wherein merging the first 3D model and the second 3D model is based on the alignment of the one or more points.

4. The system of claim 1, wherein the one or more images comprise a first image of the dental impression and a second image of the same dental impression or of another dental impression of the same dental arch as the dental impression, wherein the 3D model comprises a first 3D model corresponding to the first image and a second 3D model corresponding to the second image.

5. The system of claim 4, further comprising:
    a model merging system configured to:
        align one or more points corresponding to the first 3D model with one or more points corresponding to the second 3D model; and
        merge the first 3D model and the second 3D model to generate a merged model, wherein merging the first 3D model and the second 3D model is based on the alignment of the one or more points.

6. The system of claim 1, further comprising a manufacturing system configured to manufacture a dental aligner based on the 3D model, the dental aligner being specific to the user and configured to reposition one or more teeth of the user.

7. The system of claim 1, wherein the model generation system is further configured to:
    generate, using the generated 3D model of the dental arch of the user, a user interface for rendering at a user device that includes the generated 3D model; and
    transmit, to the user device, the generated user interface for rendering to the user.

8. A method comprising:
    receiving, by one or more processors, a plurality of data packets of a training set, each data packet of the plurality of data packets including data corresponding to one or more training images of a dental impression of a respective dental arch and a three-dimensional (3D) training model of the respective dental arch;
    identifying, by the one or more processors, for each data packet of the plurality of data packets of the training set, a plurality of correlation points between the one or more training images and the 3D training model of the respective dental arch;
    generating, by the one or more processors, a machine learning model using the one or more training images, the 3D training model, and the plurality of correlation points between the one or more training images and the 3D training model of each data packet of the plurality of data packets of the training set; and
    receiving, by the one or more processors, one or more images of a dental impression of a dental arch of a user; and
    generating, by the one or more processors, a 3D model of the dental arch of the user by applying the one or more images of the dental impression to the machine learning model.

9. The method of claim 8, wherein the one or more images of the dental impression are one or more first images of a first dental impression of the dental arch of the user, wherein the 3D model is a first 3D model, and wherein the method further comprises:
    receiving, by the one or more processors, one or more second images of a second dental impression of the dental arch of the user; and
    generating, by the one or more processors, a second 3D model of the dental arch of the user by applying the one or more second images of the second dental impression to the machine learning model.

10. The method of claim 9, further comprising:
    aligning, by the one or more processors, one or more points corresponding to the first 3D model with one or more points corresponding to the second 3D model; and
    merging, by the one or more processors, the first 3D model and the second 3D model to generate a merged model, wherein merging the first 3D model and the second 3D model is based on the alignment of the one or more points.

11. The method of claim 8, wherein the one or more images comprise a first image of the dental impression and a second image of the same dental impression or of another dental impression of the same dental arch as the dental impression, wherein the 3D model comprises a first 3D model corresponding to the first image and a second 3D model corresponding to the second image.

12. The method of claim 11, further comprising:
aligning, by the one or more processors, one or more points corresponding to the first 3D model with one or more points corresponding to the second 3D model; and
merging, by the one or more processors, the first 3D model and the second 3D model to generate a merged model, wherein merging the first 3D model and the second 3D model is based on the alignment of the one or more points.

13. The method of claim 8, further comprising manufacturing, by a manufacturing system, a dental aligner based on the 3D model, the dental aligner being specific to the user and configured to reposition one or more teeth of the user.

14. The method of claim 8, further comprising:
generating, by the one or more processors using the generated 3D model of the dental arch of the user, a user interface for rendering at a user device that includes the generated 3D model; and
transmitting, by the one or more processors to the user device, the generated user interface for rendering to the user.

15. A method comprising:
receiving, by one or more processors, one or more images of a dental impression of a dental arch of a user;
generating, by the one or more processors, a three-dimensional (3D) model of the dental arch of the user by applying the one or more images to a machine learning model to generate the 3D model, the machine learning model trained based on correlations between one or more training images of dental impressions of respective dental arches and three-dimensional (3D) training models of the respective dental arches; and
outputting, by the one or more processors, the 3D model of the dental arch to one or more computing devices.

16. The method of claim 15, wherein the 3D model is a first 3D model, and wherein the method further comprises generating, by the one or more processors, a second 3D model of the dental arch of the user based on the first 3D model of the dental arch of the user.

17. The method of claim 16, further comprising training, by the one or more processors, the machine learning model using the one or more training images and the 3D training models.

18. The method of claim 15, wherein the 3D model of the dental arch is a first 3D model, the method further comprising merging the first 3D model with a second 3D model.

19. The method of claim 18, wherein the second 3D model is a second 3D model of the dental arch.

20. The method of claim 18, wherein merging the first 3D model with the second 3D model comprises generating a merged model comprising a portion of the first 3D model and a portion of the second 3D model.

\* \* \* \* \*